(12) United States Patent
Schnappauf et al.

(10) Patent No.: US 12,288,291 B2
(45) Date of Patent: Apr. 29, 2025

(54) METHOD AND SYSTEM FOR GENERATION OF A MODEL FOR USE IN A VIRTUAL EXTRACTION PROCEDURE OF A TARGETED EXTRACTION OBJECT IN A PATIENT

(71) Applicant: Institut Straumann AG, Basel (CH)

(72) Inventors: Albrecht Schnappauf, Witzschdorf (DE); Benjamin Jaehn, Chemnitz (DE); Theo Uwimana Perrod, Basel (CH)

(73) Assignee: Institut Straumann AG, Basel (CH)

( * ) Notice: Subject to any disclaimer, the term of this patent is extended or adjusted under 35 U.S.C. 154(b) by 0 days.

(21) Appl. No.: 18/602,433

(22) Filed: Mar. 12, 2024

(65) Prior Publication Data

US 2024/0312132 A1    Sep. 19, 2024

(30) Foreign Application Priority Data

Mar. 13, 2023  (DE) .................... 10 2023 106 238.7

(51) Int. Cl.
    G06T 19/00    (2011.01)
    A61C 13/00    (2006.01)
    (Continued)

(52) U.S. Cl.
    CPC .......... *G06T 17/00* (2013.01); *A61C 13/0004* (2013.01); *A61C 13/34* (2013.01);
    (Continued)

(58) Field of Classification Search
    None
    See application file for complete search history.

(56) References Cited

U.S. PATENT DOCUMENTS

2009/0042167 A1 *  2/2009  Van Der Zel ........ A61C 9/0053
                                              433/172
2010/0260405 A1 * 10/2010  Cinader, Jr. ............. A61C 7/00
                                              382/128
(Continued)

FOREIGN PATENT DOCUMENTS

EP            2644156 A1     10/2013

OTHER PUBLICATIONS

DE102023106238.7, "Examination Report", Dec. 15, 2023, 10 pages.
JP2024-039377 , "Office Action", Aug. 6, 2024, 2 pages.
KR10-2024-0033916, "Office Action", Oct. 22, 2024, 2 pages.

*Primary Examiner* — Martin Mushambo
(74) *Attorney, Agent, or Firm* — Kilpatrick Townsend & Stockton LLP

(57) ABSTRACT

A method for generating a virtual model of an object in a patient's anatomy. The method employs a surface scan of an anatomical region of the patient's oral cavity and a volumetric density scan of the anatomical region. The method includes receiving a first dataset of labeled surface scan segments, receiving a second dataset of labeled volumetric density scan segments, cross-mounting in a coordinate system, labeled surface scan segments from the first dataset to labeled volumetric density scan segments from the second dataset, receiving identification of the targeted extraction object, identifying the 3D volumetric density model and the 3D surface model associated with the volumetric density scan segment label, and generating a third dataset comprising and 3D model of a socket, a 3D model of portions of a tooth crown, a 3D model of portions of a target extraction tooth, and/or a 3D model of the extraction contour.

35 Claims, 46 Drawing Sheets

(51) Int. Cl.
    *A61C 13/34*     (2006.01)
    *G06T 3/4007*     (2024.01)
    *G06T 15/04*     (2011.01)
    *G06T 17/00*     (2006.01)
    *G06T 19/20*     (2011.01)

(52) U.S. Cl.
    CPC ............ G06T 3/4007 (2013.01); G06T 15/04 (2013.01); G06T 19/20 (2013.01); *G06T 2219/2004* (2013.01)

(56) References Cited

U.S. PATENT DOCUMENTS

| | | | |
|---|---|---|---|
| 2015/0145864 A1* | 5/2015 | Buyanovskiy | G06T 15/08 345/426 |
| 2018/0028065 A1* | 2/2018 | Elbaz | A61B 5/7435 |
| 2018/0153646 A1 | 6/2018 | Sachdeva et al. | |
| 2018/0344894 A1 | 12/2018 | Kay et al. | |
| 2019/0282331 A1 | 9/2019 | Rubbert et al. | |
| 2020/0030065 A1 | 1/2020 | Touati et al. | |
| 2020/0113656 A1 | 4/2020 | Jo | |
| 2020/0306010 A1* | 10/2020 | Aamodt | A61C 7/002 |
| 2020/0405455 A1* | 12/2020 | Nikolskiy | A61C 13/0004 |
| 2021/0059787 A1 | 3/2021 | Levin | |

\* cited by examiner

FIG. 9B

METHOD AND SYSTEM FOR GENERATION OF A MODEL FOR USE IN A VIRTUAL EXTRACTION PROCEDURE OF A TARGETED EXTRACTION OBJECT IN A PATIENT

CROSS-REFERENCES TO RELATED APPLICATIONS

This application is related to Germany Patent Application No. 10 2023 106 238.7, filed Mar. 13, 2023, the entire contents of which are hereby incorporated in their entirety for all purposes.

BACKGROUND

Digital software tools for anatomical treatment planning and/or prosthetic restoration design rely on accurate scan data of anatomical objects of interest together with neighboring anatomical structures such as bone, tissue, nerve tracts, organs and other anatomical structures/objects/features, as well as artificial structures such as surgical implants, abutments, other anchoring systems, artificial analogues of natural structures, among other natural and artificially placed anatomical structures. In the field of digital dental technology, scan data of anatomical structures are generally determined optically or radiologically.

BRIEF SUMMARY

Digital software tools for anatomical treatment planning and/or prosthetic restoration design rely on accurate scan data of anatomical objects of interest together with neighboring anatomical structures such as bone, tissue, nerve tracts, organs and other anatomical structures/objects/features, as well as artificial structures such as surgical implants, abutments, other anchoring systems, artificial analogues of natural structures, among other natural and artificially placed anatomical structures.

In the field of digital dental technology, scan data of anatomical structures are generally determined optically or radiologically. Optical scanners for three-dimensional measurement directly from intra-oral surface structures, or from extra-oral impressions of oral surface structures, are widespread and economical. Usually, surface data is represented by a surface mesh comprising triangular elements, which are routinely saved and exchanged between systems in STL or similar surface definition formats.

Radiological scanners such as digital volume tomographs (DVT) or computer tomographs (CT) use X-rays to generate volume datasets of anatomical structures. Surface representations can also be determined from these datasets by applying thresholding methods in which the intensity values (measured in Hounsfield units) of the individual scan elements (voxels) are analyzed to determine whether they exceed or fall below certain thresholds. Radiologically dense structures (hereinafter "volumetric density" structures or objects) such as teeth can be identified in this way and the boundary surface of the identified volumetric density scan structures can be modeled as triangulated surface data (e.g. a triangular surface mesh) and again be saved and exchanged between systems in STL or similar sur-face definition formats.

Computations with MR scan data are more complex, in which contour analysis methods are preferably applied, which work on the basis of the gradients of adjacent scan elements. However, also in these cases, volumetric structures or objects such as gum, gingiva, and other tissue, predominantly soft tissue, can be identified and its boundary surface modeled as triangulated surface data for further processing.

With the analysis methods described, triangulated surface data of desired surfaces, such as, for ex-ample, visible surfaces, or boundary surfaces, such as, for example, inter object surfaces or other in-visible surfaces between anatomical objects and/or structures in the scan data can be obtained for all modalities (imaging devices). In the context of the present disclosuredispenser , the volumetric density scan data can, for example, comprise all of the above mentioned types of data, regardless of how they have been obtained, but also other algorithmic and/or interactively determined structures such as preparation lines, segmentation lines and anatomical landmarks as well as desired contact points for us in virtual extraction procedures, virtual tooth restoration procedures, virtual prosthetics design and placement procedures, etc.

Optical surface scan data is typically preferred for the evaluation or computation of virtual tooth restorations due to the ability to achieve high precision without exposing a patient to high-level dose of radiation.

In the context of the present disclosure, the term tooth restoration parts includes every type of object that can be made for the treatment of dental aesthetics and/or defects. Examples are inlays, onlays, partial crowns, crowns, telescopic crowns, bridges, veneers, implant abutments, partial pros- theses and prostheses. Also, in the context of the present disclosure, for the sake of simplicity, tooth replacement parts are also covered by the term tooth restoration parts. The term virtual tooth restoration (referred to more briefly as tooth restoration in the following) is to be understood to include appropriate electronic representations of tooth restorations, i.e. digital three-dimensional representations, preferably surface representations, of such tooth restoration parts of sufficient accuracy. For example, to manufacture a tooth restoration part, a CAD/CAM data set of the corresponding virtual tooth restoration can be forwarded to a manufacturing machine.

When treating a dental defect, a preparation of the teeth usually takes place, i.e. caries, old filling material or defective tooth parts are removed. What remains for each tooth is the remaining tooth structure, whose surface is divided into a prepared part (cavity) and an unprepared part. The boundary line between unprepared tooth surface and prepared tooth surface is referred to as the preparation line. In addition to the preparation lines, present only in the case of prepared teeth, each tooth also has at least one segmentation line that separates a tooth from extra-dental structures such as gum and/or bone and/or adjacent teeth. It follows from these definitions that segmentation lines and/or preparation lines delimit unprepared tooth surfaces. In the context of the present disclosure, these boundary lines could be placed in the scan data, predominantly interactively, by use of a graphical user interface, whereby algorithmic assistance, based on the analysis of surface curvatures of the scan data, is usually used in their determination.

Because of the complex structure of the scan data and the multitude of functional-aesthetic criteria that must be fulfilled—adjustment to opposing dentition, possibly under consideration of jaw movement, adjustment to adjacent teeth under consideration of contact points, adjustment to the preparation lines in order to obtain an optimal margin fit, compliance with minimum material strengths in order to obtain a satisfactory mechanical stability, consideration of desired tooth shapes in the anterior tooth region, etc.—the process of designing a custom tooth restoration, even with the assistance of an interactive computer-aided design tool, requires a human with the knowledge and experience of both dental restoration design as well as training in using such tools.

To add to the complexity of designing customer prosthetics, prosthetics are often designed to re-place an anatomical object that was removed from the existing oral situation. For example, the de-signer may be tasked with designing a temporary or permanent prosthetic to be placed on an abutment attached to an implant that is placed in a socket of an extracted object. A designer can achieve better accuracy by basing the design of the prosthetic on the patient's actual anatomical contours in the socket left where the extracted object was previously seated. Thus, often, after extraction of the anatomical object, the area had to be optically re-scanned prior to sending the surface model to the designer.

There is an increasing demand for more immediacy in dental treatments. In particular, for procedures that can be completed in one or fewer office visits than would have been possible in the past, novel ways to shorten dental treatment pre-planning are being sought.

In the situation where an anatomical object is targeted for extraction, methodologies are being sought to pre-plan the design of prosthetics such that they can be ready to install in position immediately in place of the extracted anatomical objects in the patient's oral cavity. For example, it may be desired to pre-plan placement of an implant and pre-plan the design of a temporary abutment such that immediately upon tooth extraction (i.e., during the same office visit), an implant can be placed, and a custom temporary abutment installed. It would also be desirable for the abutment to be designed and manufactured, such as, by additive or subtractive manufacturing, e.g. 3D printing or milling, respectively, and installed in the patient's mouth within the same office visit to accommodate immediacy situations as much as possible.

Ideally, a prosthetic should be designed to fit within and conform to the contours of the socket created upon extraction of the anatomical object. However, modern prosthesis design tools such as CAD/CAM systems receive only surface data (represented as a 3D triangular mesh, typically in STL format) and thus miss information of any hidden structures, such as bone or other internal structures and contours. Accordingly, there is no information available in the prosthesis design tools regarding the socket profile of the extracted anatomical object(s) but designers typically estimate the socket profile of the extracted anatomical object when designing the prosthetic to fit in its place.

This can lead to poor-fitting or misalignment of the so designed prosthetics when placed into the patent's oral cavity and can in turn lead to patient discomfort or other treatment-related troubles.

It is an object of the present disclosure to help alleviate at least some of the disadvantages of known dental restoration or prosthetics design and placement procedures. In particular, it is an object of the present disclosure to help provide methods and systems helping to improve the pre-planning of dental restoration or prosthetics procedures using CAD/CAM tools.

The object is solved by a computer implemented method for automatically generating a 3-dimensional model for use in a virtual extraction of a targeted extraction object of a patient according to independent claim 1 as well as a system for automatically generating a 3-dimensional model for use in a virtual extraction of a targeted extraction object of a patient according to independent claim 14.

Dependent claims 2 to 13 represent embodiments of the present disclosure.

According to the a first aspect, a computer implemented method automatically generates, by one or more computer processors, a 3-dimensional model for use in a virtual extraction of a targeted ex-traction object of a patient, the targeted extraction object comprising an object in a patient's anatomy. The method is based on a surface scan of an anatomical region of the patient's oral cavity as well as a volumetric density scan of the same or similar anatomical region, wherein the anatomical region includes at least the targeted extraction object. The method comprises: receiving a first dataset of labeled surface scan segments, each surface scan segment comprising a 3-dimensional (3D) surface model of a corresponding object recognized and segmented from surface scan data of the surface scan, and each surface scan segment having an associated label identifying the surface scan segment, and receiving a second dataset of labeled volumetric density scan segments, each volumetric density scan segment comprising a 3-dimensional (3D) volumetric density model of a boundary surface of a corresponding object recognized and segmented from volumetric density scan data of the volumetric density scan, and each volumetric density scan segment having an associated label identifying the volumetric density scan segment.

The recognizing and segmenting of objects in the surface scan data of the surface scan and/or the volumetric density scan data of the volumetric density scan can be based on or assisted by automatic data analysis, such as, for example, analysis by a suitably trained neural network able to distinguish anatomical objects and structures from one another in the surface scan data and/or the volumetric density scan data.

In an embodiment, the associated labels of each surface scan segment and/or each volumetric density scan segment identifies the respective surface scan segments and the respective volumetric density scan segments as corresponding to a tooth, a portion of a tooth, a prosthetic tooth, a portion of gum tissue, a portion of bone, an implant, or another object or structure present in the patient's oral cavity and/or the anatomical region.

Labeled surface scan segments from the first dataset are cross mounted in a common 3D coordinate system to labeled volumetric density scan segments from the second dataset. In an embodiment, the cross-mounting may be implemented by using correspondingly labeled surface scan segments and volumetric density scan segments. Alternatively, or in addition to this, the cross mounting may be implemented by determining surface scan segments and volumetric density scan segments of similar shape and volume.

In an embodiment, the cross-mounting may include scaling, translatory and rotatory transformations applied to the surface scan segments and/or volumetric density scan segments in order to achieve the best possible registration of the surface scan segments and volumetric density scan segments in the common 3D coordinate system. In an embodiment, cross-mounting parameters, such as, scaling factors, translatory and/or rotational transformation parameters for up to 3 spatial dimensions may be stored and used for the purposes of "overlaying" separately maintained labeled surface scan segments and labeled volumetric density scan segments or portions thereof, where necessary in the following procedure.

In an embodiment, the cross-mounting includes generating a fifth dataset of labeled segments, each segment comprising a combined 3-dimensional (3D) model representing an anatomical object, wherein the combined 3-dimensional (3D) model includes labeled segments of both labeled surface scan segments and labeled volumetric density scan segments. In some applications, portions of the labeled surface scan segments and/or the labeled volumetric density scan segments may, however, be removed from the combined 3-dimensional (3D) model representing an anatomical object.

For the purpose of the following disclosure, where portions co-represented in the identified 3D volumetric density model and the identified 3D surface model are being determined, this determination may be based on the operation of cross-mounting labeled surface scan segments from the first dataset and labeled volumetric density scan segments from the second dataset, whereby an association of the labeled surface scan segments from the first dataset and labeled volumetric density scan segments from the second dataset may be established and the association information stored in a transitory or non-transitory storage component. Alternatively, determining portions co-represented in the identified 3D volumetric density model and the identified 3D surface model may also be determined in a separate operation where association of correspondingly labeled surface scan segments from the first dataset and volumetric density scan segments from the second dataset with one another is established, and, optionally, the association information stored in a transitory or non-transitory storage component.

The one or more computer processors receives the targeted extraction object. This includes receiving a selection of a targeted extraction object which may be manually selected, or the selection assisted by a suitably trained neural network able to identify objects likely targeted for extraction, such as, for example, damaged or modified objects, anatomical location or orientation of objects, or unhealthy objects, in the surface scan data and/or the volumetric density scan data.

In an embodiment, the targeted extraction object is a tooth or a portion of a tooth, such as, for example, the tooth's root.

Both the 3D volumetric density model associated with the volumetric density scan segment label as well as the 3D surface model associated with the surface scan segment label which correspond to the identified targeted extraction object are identified.

The method of the first aspect may include generating a third dataset comprising a model comprising a 3D model of a socket being an equivalent of the identified 3D volumetric density model less portions of the identified 3D volumetric density model co-represented in the identified 3D surface model. In an embodiment, the 3D model of a socket (socket model) comprises a 3-dimensional model of a patient's tooth socket which seats the target extraction object.

For the purpose of the present disclosure, it is assumed that the 3D model of a socket substantially corresponds to portions of the identified 3D volumetric density model.

In an embodiment, the 3D model of a socket is generated by determining portions of the identified 3D volumetric density model not co-represented in the identified 3D surface model. This means that, in a case where the targeted extraction object is a tooth, the socket model is derived by determining those parts of the identified 3D volumetric density model that have no co-represented identified 3D surface model, which would generally include at least a part of the tooth's root.

In an alternative embodiment, the 3D model of a socket is generated by determining portions of the identified 3D volumetric density model co-represented in the identified 3D surface model, and determining a difference between the determined co-represented portions and the 3D volumetric density model by removing the determined co-represented portions from the 3D volumetric density model.

In an embodiment, the determined portions of the identified 3D volumetric density model are stored in a computer-readable data storage component, which may be a transitory or non-transitory storage component, including network storage components.

The method of the first aspect may further include generating a third dataset comprising a model comprising at least a portion of the identified 3D volumetric density model co-represented in the identified 3D surface model and/or at least a portion of the identified 3D surface model co-represented in the identified 3D volumetric density model. The third dataset will thus include a representation of at least parts of the visible portions of the targeted extraction object, such as, for example, a tooth's crown or a prosthesis.

The method of the first aspect may further include generating a third dataset comprising a model comprising at least a portion of the identified 3D volumetric density model less portions of the identified 3D volumetric density model co-represented in the identified 3D surface model. The third dataset will thus include a representation of at least parts of the invisible portions of the targeted extraction object, such as, for example, a tooth's root, an implant and/or an abutment.

The method of the first aspect may further include generating a third dataset comprising a model comprising at least a subset of the first dataset less portions of the identified 3D surface model co-represented in the identified 3D volumetric density model.

In an embodiment, the method may include the generation of a fourth dataset by removing portions of the identified 3D surface model co-represented in the identified 3D volumetric density model from a copy of at least a subset of the first dataset. The third dataset will thus include a representation of the visible portions of at least a part of the patient's oral cavity sans the visible portions of the targeted extraction object as defined by the identified 3D surface model.

The third dataset generated by the method of the first aspect thus includes a representation of at least parts of the anatomical region of the patient including or excluding a representation of the targeted extraction object. This helps to improve the preplanning of dental restoration or prosthetics procedures using CAD/CAM tools as use by the designer of the prosthesis and can result in an improved fitting and alignment of the prosthesis within the patent's oral cavity. Additionally, the information provided in the third dataset is suitable to improve prosthesis design such that it may be ready to install in position immediately in place of the extracted anatomical objects in the patient's oral cavity, by potentially having an implant placed, a custom temporary or permanent abutment installed and a prosthesis fitted during one and the same office visit.

In an embodiment, the method comprises determining a boundary of the identified 3D surface model and generating a cut-line from the determined boundary. This may include smoothing, straightening or averaging of the identified 3D surface model boundary. It may also include determining an intersection curve between the surface definition of the identified 3D surface model and the boundary surface of the 3D volumetric density model. The so-defined cut-line is then projected onto the identified 3D volumetric density model and may be used for generating sixth dataset comprising the identified 3D surface model and/or the identified 3D volumetric density model on the side of the cut-line that includes substantially all portions of the identified 3D volumetric density model that are co-represented in the identified 3D surface model. The sixth dataset may thus include a representation of at least parts of the visible portions of the targeted extraction object having an improved boundary representing essentially the demarcation line between the visible portion of the targeted extraction object in the patient and the invisible portions thereof.

In an embodiment, the method further comprises augmenting any one of the first, second, third, fourth, fifth and/or sixth dataset, or the identified 3D surface model and/or the identified 3D volumetric density model when having a void in a surface defined by the dataset or model, respectively, and thus filling such void with generated surface information. The generated surface information may be generated by interpolating the boundaries of the void and/or based, at least in part, on standard anatomical modeling, which may be determined by a suitably trained neural network able to generate corresponding sections of anatomical objects and structures. The generated surface information may thus provide for a steadily continuous progression of the existing surface information in the dataset(s) or model(s), respectively, and, in the best case, represents an authentic representation of the surfaces or boundary surfaces of the patient's anatomical objects or structures at the positions where the dataset(s) or model(s) are incomplete.

In an embodiment, the method comprises storing any of the third, fourth, fifth, sixth and/or seventh datasets and/or merged or cross-mounted versions thereof, in a computer-readable data storage component, which may be a transitory or non-transitory storage component, including a networked storage component. The information may be stored in data exchange formats or surface definition formats like STL for import into and use by the CAD/CAM system in the process of designing a prosthesis.

The present disclosure also refers to a system for automatically generating a 3-dimensional model for use in a virtual extraction of a targeted extraction object of a patient, where the system comprises one or more computer processing units configured to load and execute computer-readable instructions which, when executed configure the one or more computer processing units to implement the method of the first aspect and its embodiments as described heretofore.

In an embodiment of the system of the present disclosure, the system includes an imaging application and an electronic display apparatus for displaying graphical representations of at least any one or more of the first, second, third, fourth, fifth, sixth and/or seventh dataset and/or merged or cross-mounted versions thereof, or the identified 3D surface model and/or the identified 3D volumetric density model to the user for viewing and modification.

The imaging application, in conjunction with the electronic display apparatus, is configured to automatically update the display of the graphical representations of the first, second, third, fourth, fifth, sixth and/or seventh dataset and/or merged or cross-mounted versions thereof, or the identified 3D surface model and/or the identified 3D volumetric density model whenever these datasets and/or models are updated and information added or removed from them.

In addition to the display of the graphical representations of the first, second, third, fourth, fifth, sixth and/or seventh dataset and/or merged or cross-mounted versions thereof, or the identified 3D surface model and/or the identified 3D volumetric density model, the imaging application also provides display controls responsive to user input to modify the display of the graphical representation of the graphical representations of the first, second, third, fourth, fifth, sixth and/or seventh dataset and/or merged or cross-mounted versions thereof, or the identified 3D surface model and/or the identified 3D volumetric density model, such as, for example, to allow modification of the viewing angle, rotation or pitch of the information displayed.

Further to the display controls, the imaging application also provides selection controls which, upon activation, allow user selection of at least one of objects graphically represented on the display. The imaging application is enabled, following receiving a selection operation using the selection controls by the user of the imaging application, to highlight labeled surface scan image segments and/or volumetric density scan image segments in the graphical representation the first, second, third, fourth, fifth, sixth and/or seventh dataset and/or merged or cross-mounted versions thereof, or the identified 3D surface model and/or the identified 3D volumetric density model, corresponding to the user's selection on the electronic display apparatus.

The imaging application further provides a virtual extraction control, which, upon activation, performing for each graphically represented object selected by the user using the selection controls the possibility to remove the targeted extraction object's graphical representation from the graphical representation displayed on the electronic display apparatus and supplement it by the graphical representation of the socket model.

The present disclosure also refers to a computer readable medium including computer readable instructions which, when executed by one or more computer processing units configure the one or more computer processing units to implement at least a component of a system for automatically generating a 3-dimensional model for use in a virtual extraction of a targeted extraction object of a patient.

The present disclosure also refers to a computer program, said computer program embodying computer readable instructions which, when executed by one or more computer processing units configure the one or more computer processing units to implement at least a component of a system for automatically generating a 3-dimensional model for use in a virtual extraction of a targeted extraction object of a patient.

The present disclosure also refers to the use of use of the third, fourth, fifth, sixth and/or seventh dataset and/or merged or cross-mounted versions thereof, in a virtual extraction procedure of a targeted extraction object of a patient.

The present disclosure also refers to the third, fourth, fifth, sixth and/or seventh dataset and/or merged or cross-mounted versions thereof, in a prosthetic design CAD/CAM software tool to generate a prosthetic design which anatomically represents the targeted extraction object of a patient. Such use may be before and/or during an office visit, preferably a single office visit, of a patient in whom an actual extraction procedure of the targeted extraction object is performed.

These uses allow to reduce the number of patient visits, potentially, from many to as few as a single visit by providing the ability to conduct accurate preplanning of the extraction procedure as well as designing and manufacturing anatomically correct prosthetics and, as the case may be, abutments either before or during the procedure. At the time of the extraction of the targeted extraction object from the patient's anatomy, the installation of the abutment/prosthesis can be conducted in situ and immediately following the extraction of the targeted extraction object.

The disclosure provides devices, systems, graphical user interfaces, computer-enabled tools, methods and processes to generate, display, export/save and use anatomically accurate virtual 3D model(s) of an anatomical cavity or socket (hereinafter, "socket") configured to conformingly seat an object (such as a tooth or implant) in an oral cavity of a mammal (human or other, hereinafter referred to as "patient").

A virtual 3D model, as used in the context of the disclosure, is a 3-dimensional digital representation of a physical object (or socket). Virtual 3D models are often represented as point clouds or triangular (or other polygonal) meshes, as commonly known and used in the computer graphics field. A virtual 3D model of a socket (or simply "socket model") implemented in accordance with the described embodiments is a virtual 3D model that sufficiently accurately represents the anatomy of an actual socket of a patient that seats an associated object, and is determined and generated based on each of a surface scan of an anatomical region of the patient's anatomy (such as the oral cavity) and a volumetric density scan of the anatomical region.

In both the surface scan and the volumetric density scan, the scanned anatomical region includes at least the object seated in the actual socket. In some use cases, a purpose behind generating the socket model is that the actual object seated in the actual socket of the patient is targeted for extraction (herein, "targeted extraction object"). For example, the object may comprise a tooth (herein, "targeted extraction tooth") or an implant (herein, "targeted extraction implant") targeted for extraction.

Having access to, and corresponding insight from, a virtual socket model specific to the patient's situation, can improve patient treatment planning, and in particular diagnosing and planning treatment related to a patient's anatomy. It can improve, for example, dental treatment planning including planning for treatment that involves extraction of a tooth, placement of an implant, an abutment and/or a prosthesis, such as, an artificial crown. It further can improve the treatment workflow by reducing the number of steps and patient visits needed to design an anatomically accurate prosthesis, such as, for example, a temporary healing abutment or a permanent abutment.

Each socket model generated as described herein substantially conforms to the contours of the outer surface of the actual object that it seats in the patient's anatomy. For example, a tooth socket model in accordance with embodiments of the present disclosure is generated to conform to the contours of a patient's actual tooth's root based volumetric density scan data (via CBCT scan, for example) of the anatomical region (including the tooth of interest) of interest.

Aspects and embodiments of the present disclosure are further described by way of the following detailed description in conjunction with the drawing. In the following detailed description, like reference numerals denote like elements except where indicated otherwise.

While the following detailed description describes certain embodiments of aspects of the present disclosure in greater detail, it is noted that features described in context with only one of the embodiments are nevertheless intended to be available also in the context of or in combination with any other embodiment of the aspects of the present disclosure whether described or not in the detailed description, except where such a combination of features would lead to non-meaningful results. In no way is the following detailed description meant to be limiting to the specific embodiments and combinations of features therein; rather, the extent and scope is exclusively limited and defined by the attached claims.

BRIEF DESCRIPTION OF THE DRAWINGS

FIGS. 7A-7J depict a second exemplary graphical user interface implementation of various aspects of the present disclosure;

DETAILED DESCRIPTION

An aspect of the present disclosure is the generation of a virtual 3-dimensional socket model which sufficiently accurately models an anatomical socket seating an object in an anatomical region in the region of the patient's oral cavity. An embodiment comprises a method for generating such socket model.

Figure 1:
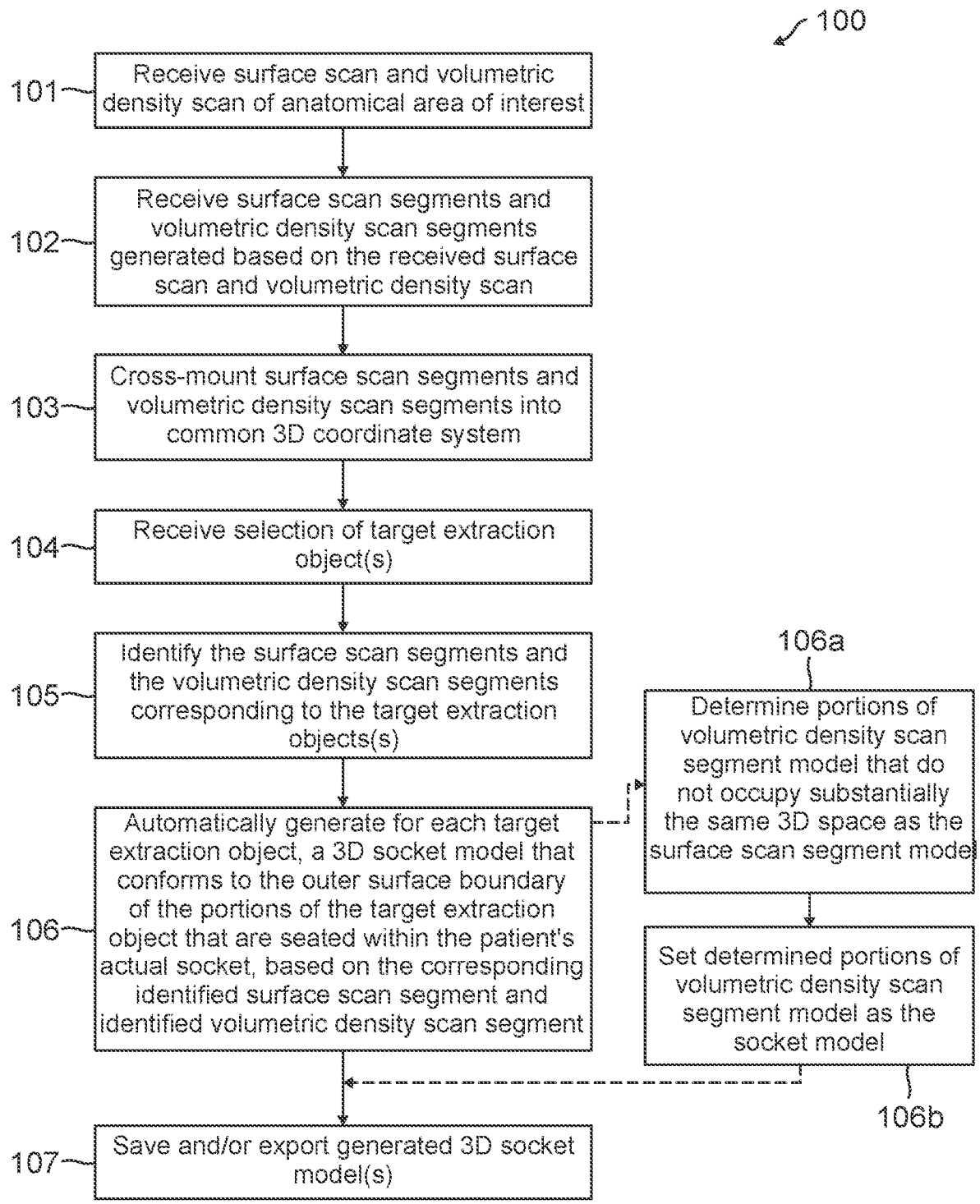
FIG. 1 represents a flow diagram outlining a first aspect of the method according to an embodiment of the present disclosure.
Figure 2:
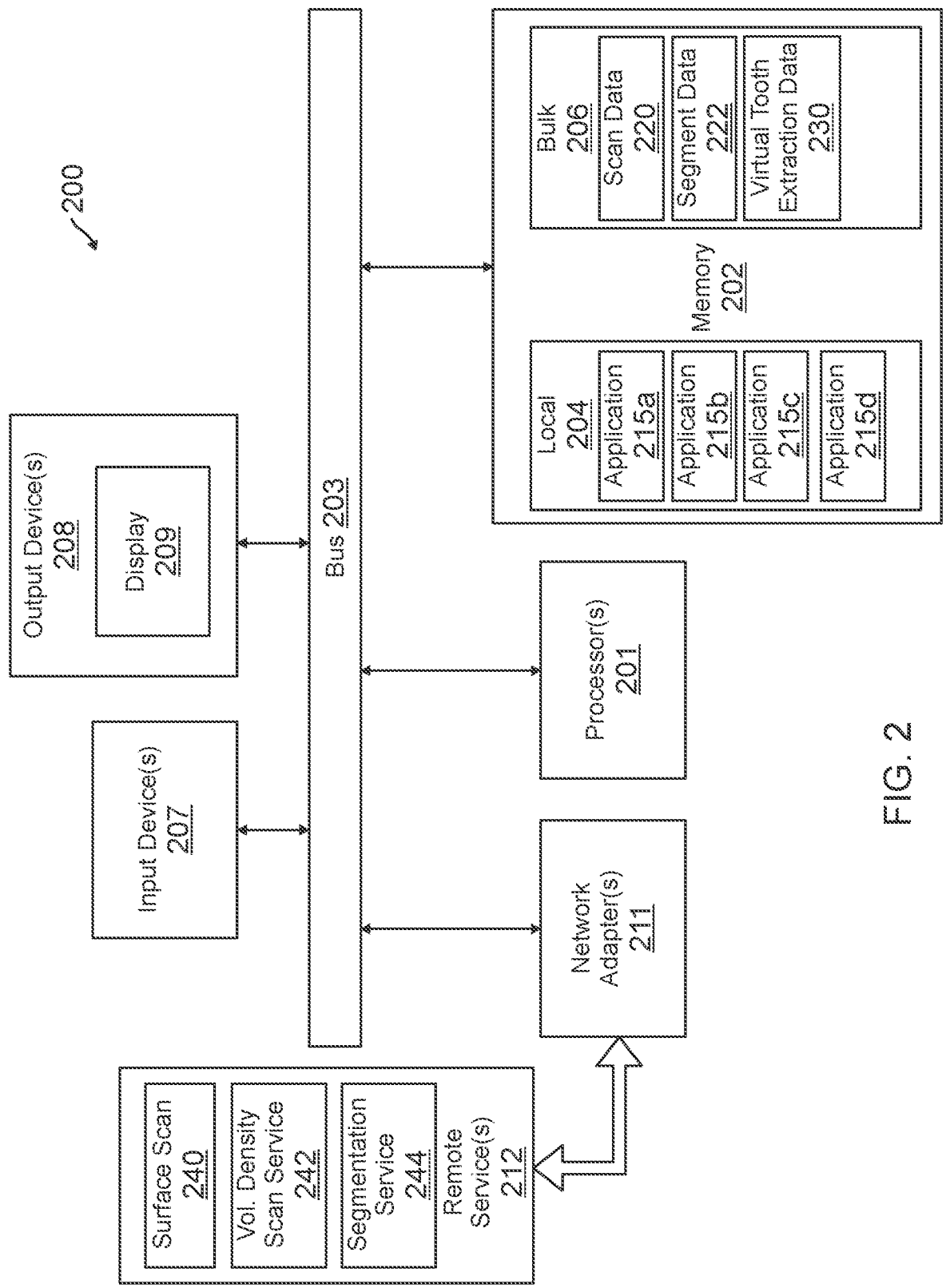
FIG. 2 represents an architectural diagram of the system according to an embodiment of the present disclosure.

FIG. 1 is a flowchart of a method 100, executing in a computer-enabled device such as system 200 of FIG. 2, for generating a 3D socket model that accurately represents the anatomy of an actual socket of in the patient's anatomy that seats an associated object, such as a tooth. The method 100 includes a step 101 of receiving each of a surface scan and a volumetric density scan (both stored in scan data 220 of system 200) of an anatomical area of the patient's oral cavity, where the scanned anatomical region includes at least the targeted object, in this example in the form of at least a portion of the actual object seated in the actual socket of the patient.

Method 100 further includes a step 102 of receiving a first dataset of labeled surface scan segment(s) and a second dataset of labeled volumetric density scan segment(s) (both stored in segment data 222), comprising individual segments corresponding to objects and/or features recognized, via image recognition and segmentation processing in the surface scan and the volumetric density scan of the anatomical region of interest. Steps 101 and 102 may occur outside of the execution of the application 215*a*, for example by a remote service 212.

For example, the surface scan data 220 may be generated by a remote surface scan service 240. A surface scan service 240 may do any one or any combination of the following: collection of surface scan data collected from a surface scanner (such as an optical scanner or camera), converting the surface scan data into a 3-dimensional model which can be accessed and read by the processor(s) 201 of the system 200, manipulated or converted into another format, if necessary, to ready it for display on an electronic display 209, and saved in a computer-readable file that may be received by the system 200 and stored in local memory 220 reserved for scan data.

As another example of a remote service, volumetric density scan data 220 may be generated by a remote volumetric density scan service 240. A volumetric density scan service 240 may do any one or any combination of the following: collection of volumetric density scan data collected from a volumetric density scanner (using volumetric scanning equipment such as cone-beam computer tomography (CBCT) scanner), converting the volumetric density scan data into a 3-dimensional model which can be accessed and read by the processor(s) 201 of the system 200, manipulated or converted into another format, if necessary, to ready it for display on an electronic display 209, and saved in a computer-readable file that may be received by the system 200 and stored in local memory 220 reserved for scan data.

Another remote service 212 may include a segmentation service 244. Segmentation service receives scan data (surface (IOS) or volumetric density (CBCT or CT) scan data) and uses image processing, extraction and classification to segment received scan images containing the anatomical area of interest into various identified objects and associating a classification tag to each of the segment. The segmentation service 244 may provide the segments in the form of individual virtual 3D segment models, where each individual virtual 3D segment model (herein also referred to as simply "segment model") is a digital 3D representation of the actual anatomical part or feature of the patient's anatomy. In an embodiment, the segmentation service 244 provides each segment as an individual digital 3D model, preferably (but not limited to) in STL format as a triangular mesh or a point cloud.

Each of the remote services 212 returns data to the system 200 via the network adapter(s), where it is stored in appropriate bulk memory 206 (scan data 200 or segment data 222).

Either or both of steps 101 and 102 may be performed outside of the execution of the application 215a, for example by another process or application stored in local memory 204 and executed by the local processor(s) 201 of the system 200. In other embodiments, Either or both of steps 101 and 102 may alternatively or also be performed as an integral execution process within the application 215a.

Because the received surface scan segments and volumetric density scan segments are generally obtained using different modalities (and therefore different (and usually independent) scanning machines/equipment), the scan data produced by each scan modality is collected and saved according to a 3D coordinate system native to the particular scanning machine/equipment that collected the data. In these situations, it becomes important to align the resulting scan data from each scanner into a common 3D coordinate system such that like objects from each scan are matched up and are displayed as occupying the same space (which they should, since they each represent the same object).

The (labeled) surface scan segments and (labeled) volumetric density scan segments are cross-mounted into a common 3D coordinate system (step 103). The result of the cross-mounting into a common 3D coordinate system is that for each pair of surface scan and volumetric density scan segments that corresponds to the same patient object from the scanned anatomical area of interest, there should exist one or a plurality of respective points that "match" (i.e., the points from each segment in the segment pair should substantially or exactly coincide) in the 3D space of the common 3D coordinate system. These matching points correspond to a corresponding point on the actual object/feature of the patient's actual anatomy. Matching points will only be present for areas of the patient's anatomy that the particular scan modality was able to capture.

Accordingly, since the surface scan data 220 only includes surface visible image data and the volumetric scan data 220 includes both surface and subsurface image data, point matching can only occur for points of the volumetric density scan segment(s) that correspond to surface-visible points of the scanned object (since the surface scan segment(s) contain no subsurface data points). It will be noted that although ideally the points of each corresponding (or co-represented) pair of surface scan segment and associated volumetric density scan segment should exactly match up in the common 3D coordinate system, the points may only "substantially match", that is coincide within a margin of error, owing to differences in accuracy between the scan modalities as well as differences in resolution and generation accuracy of the 3D scan segment models generated for each scan modality.

Nonetheless, the cross-mounting should result in the surface scan segments corresponding to (or co-represented in) scanned objects occupying nearly identical space in the 3D coordinate system as like regions of the associated object as represented by corresponding volumetric density scan segments.

In a step 104, a selection indicating one or more targeted extraction objects is received.

The method further includes a step 106 of generating, for each targeted extraction object, a 3D model of a socket that conforms to the outer surface boundary of the portion of the targeted extraction object that is seated within the patient's actual socket. This involves identifying the 3D volumetric density model associated with the volumetric density scan segment label corresponding to the identified targeted extraction object, and identifying the 3D surface model associated with the surface scan segment label corresponding to the identified targeted extraction object, then generating—for each respective targeted extraction object—a 3D model of the socket based on the corresponding (or co-represented) identified surface scan segment model and identified volumetric density scan segment model.

In an embodiment, the step 106 is implemented by a step 106a of determining co-represented portions of the identified volumetric density model that do not occupy substantially the same 3D space as the identified surface model, and a step 106b of setting the portions determined in step 106a as the 3D model of the socket. In a step 107, the generated socket model(s) may then be saved in a file and/or exported to a save file for later use or distribution.

With reference to FIG. 2, the method 100 executes in a computer-enabled system 200 and comprises computer readable instructions stored in computer-readable memory 202 that, when executed by a computer processor 201, performs the steps of the method. In embodiments, the method is implemented within a computer-implemented application 215a (or "tool") as computer-executable instructions stored in memory 202 of the system 200, or is accessible via a remote service, through a device-enabled network adapter 211 of the system 200.

The application 215a includes computer readable instructions that, when executed by a local or remote computer processor (not shown, but executing services 112), performs the steps of the method 100. The application 215a may operate in connection with an electronic display 209. In an embodiment, the application 215a includes a graphical user interface (GUI) which is displayed and presented on the electronic display 209.

The GUI may include a 3D model view pane for displaying a 3-dimensional model of the patient's anatomical area of interest. The model shown in the view pane is based on a surface scan and a volumetric density scan of the patient's area of interest. The GUI includes various user controls to allow the user to direct the application to perform various operations, such as but not limited to: selecting and loading a patient's scan records, selecting and manipulating display views, selecting content for display in the GUI, selecting objects of interest and/or identifiers of objects of interest that may be included in a patient's scan data, selecting and viewing identifiers, descriptions and images of implants, prosthetics, materials, etc. in connection with planning dental treatment for a patient, and so on.

One or more of such controls comprise an object selection tool that allows a user to select an object that is present in the patient scan data as a targeted extraction object. One or more of such controls comprise a socket model generation tool which generates an independent 3D model of the socket in which the targeted extraction object is seated. Alternatively, or in addition, one or more of such controls comprises a virtual tooth extraction tool which when activated by a user operates to extract the selected object from the area of interest.

Alternatively, or in addition, one or more of such controls comprises an extraction tool that generates a dataset comprising a model of at least a portion of an exposed object (such as the crown of a tooth) based on at least a portion of an identified 3D volumetric density model co-represented in an identified 3D surface model and/or at least a portion of an identified 3D surface model co-represented in an identified 3D volumetric density model.

Alternatively, or in addition, one or more of such controls comprises another extraction tool that generates a dataset comprising a model of at least a portion of a concealed object (such as the root of a tooth) based on at least a portion of an identified 3D volumetric density model less portions of the identified 3D volumetric density model co-represented in an identified 3D surface model.

Alternatively, or in addition, one or more of such controls comprises a tool that generates a dataset comprising a model of at least a subset of the surface scan less portions of an identified 3D surface model co-represented in an identified 3D volumetric density model.

Figure 3A:
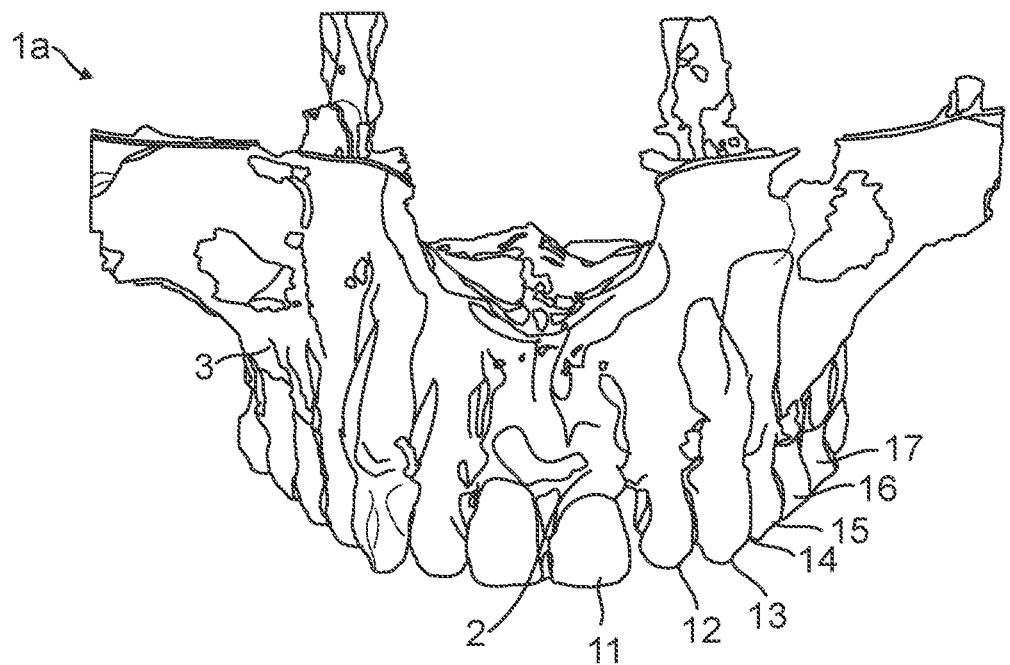
FIGS. 3A-3N illustrate an exemplary embodiment according to the present disclosure of the method of generating a socket model according to the present disclosure.
Figure 3B:
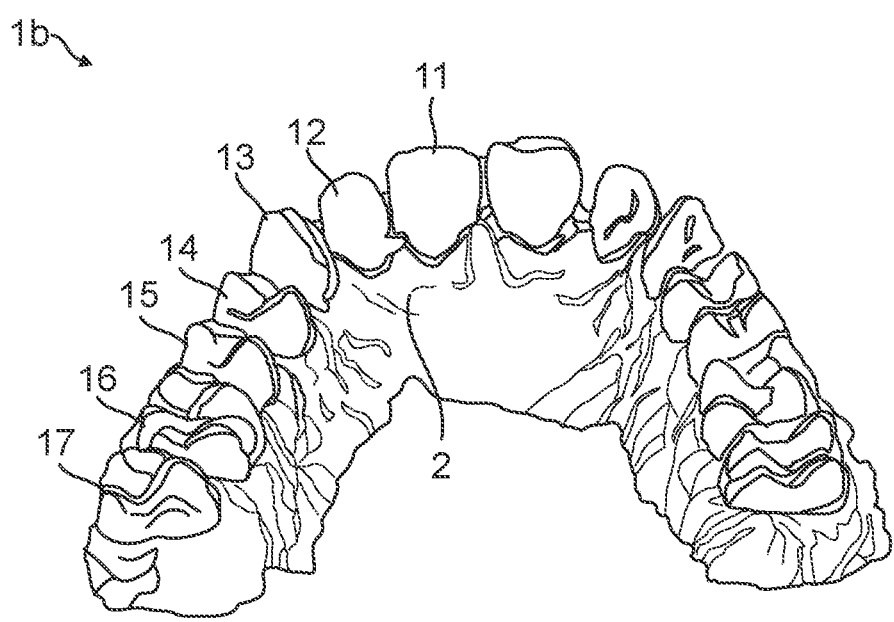
Figure 3C:
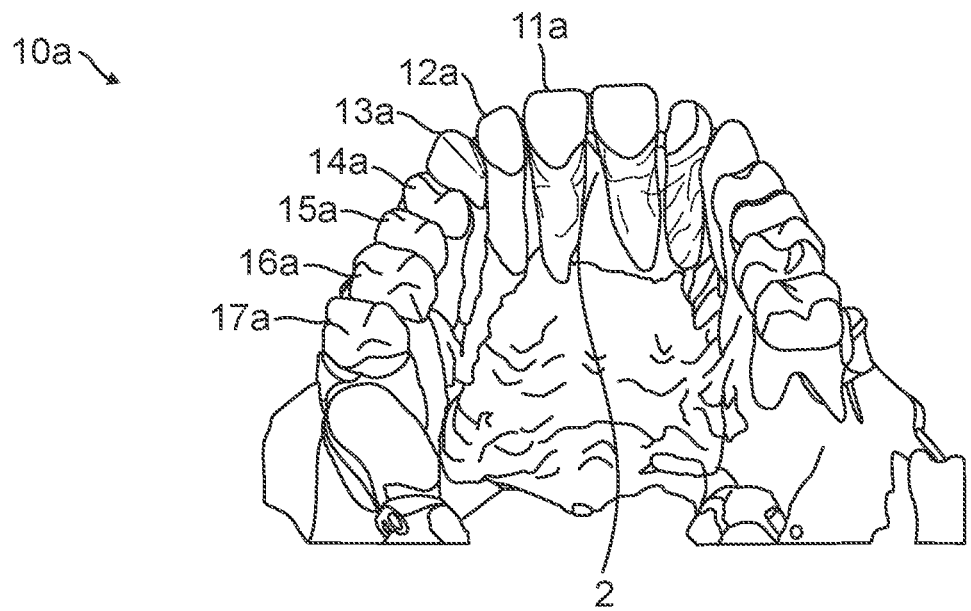
Figure 3D:
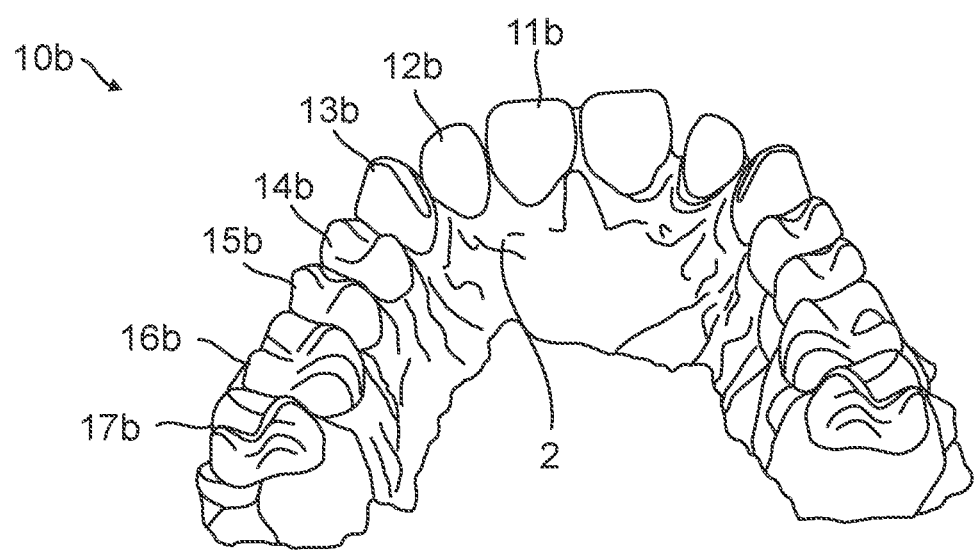
Figure 3E:
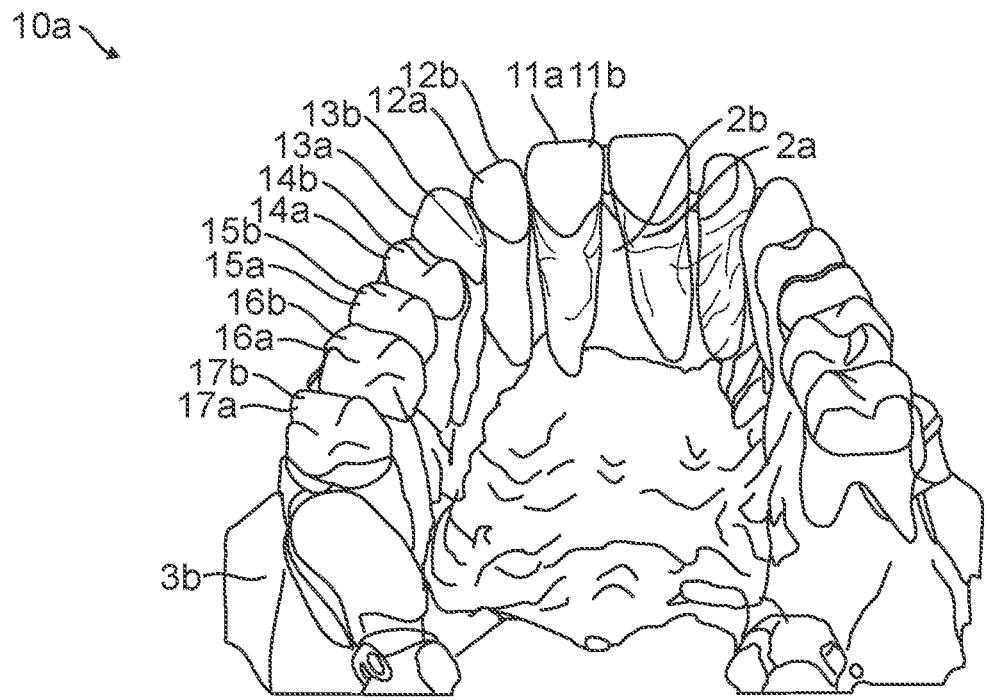
Figure 3F:
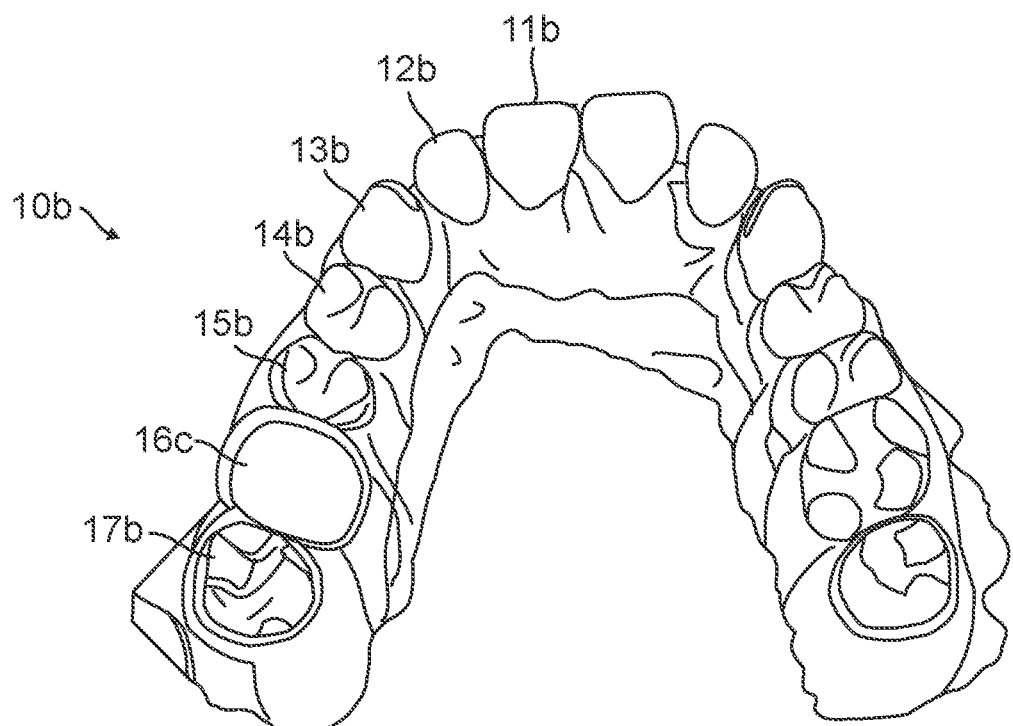
Figure 3G:
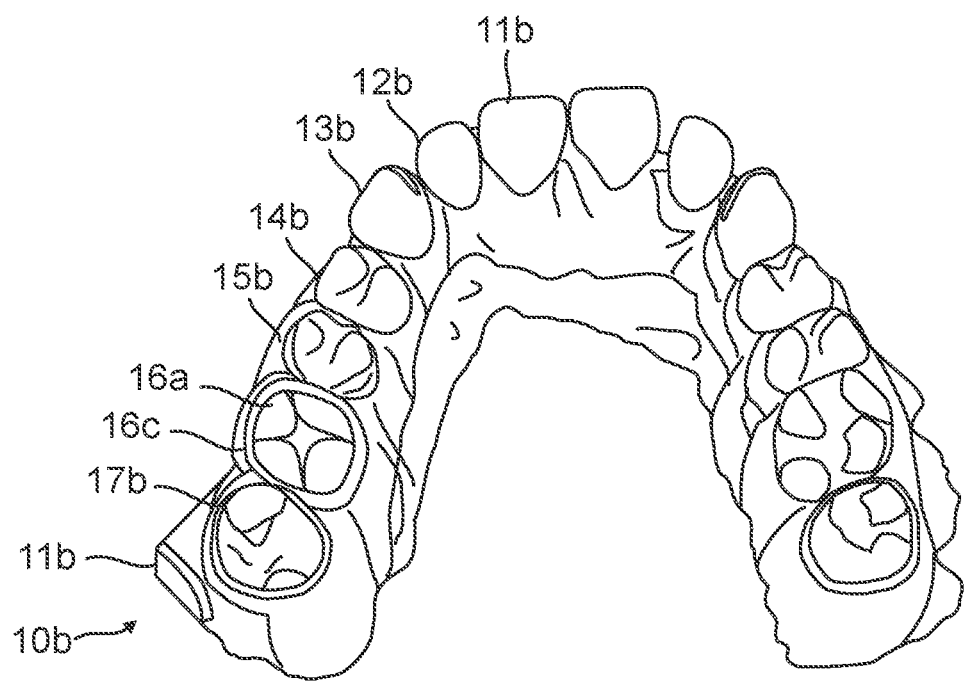
Figure 3H:
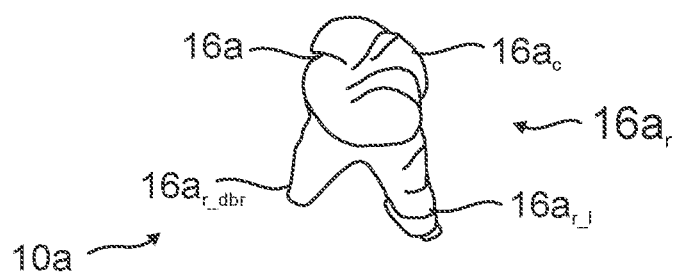
Figure 3I:
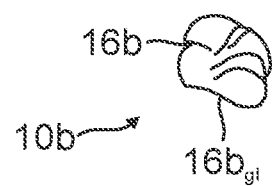
Figure 3J:
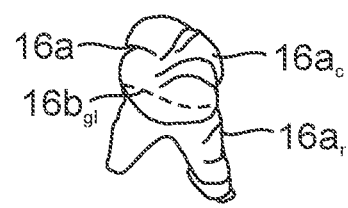
Figure 3K:
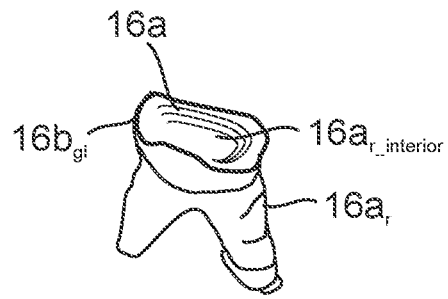
Figure 3L:
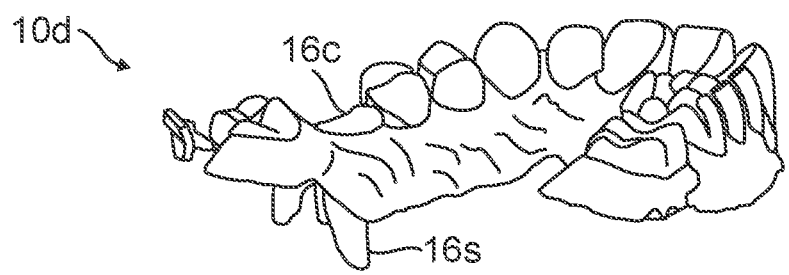
Figure 3M:
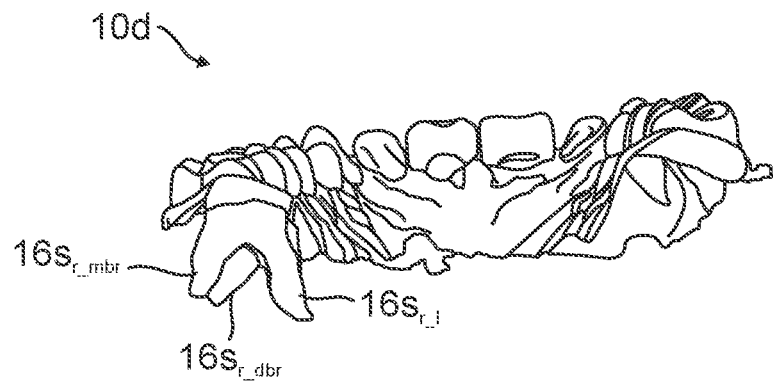
Figure 3N:
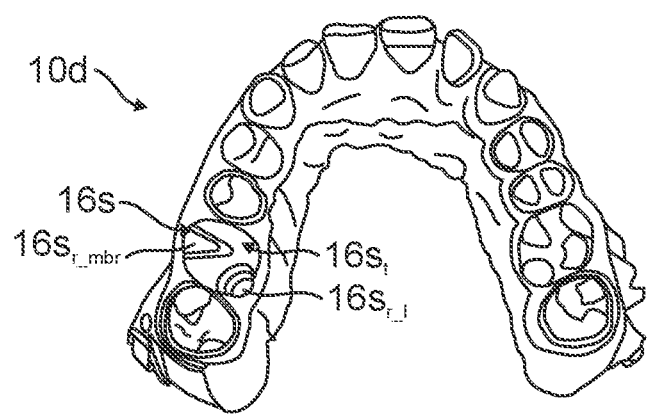

FIGS. 3A-3N illustrate an exemplary embodiment of an aspect of the present present disclosure according to which a 3-dimensional socket model is generated from the 3-dimensional surface scan segments (the 3D surface model of a corresponding object recognized and segmented from surface scan data of the surface scan) and volumetric density scan segments (the 3D volumetric density mode of a boundary surface of a corresponding object recognized and segmented from volumetric density scan data of the volumetric density scan) associated with an object. In the illustrated embodiment, the object is a tooth and the generated socket model is a tooth socket that is equivalent to the portion of the outer shape of the portion of the tooth that lies below the gumline, i.e. the tooth's root.

FIG. 3A shows an example of a 3D surface boundary model 1a generated based on a volumetric density scan. Individual structures in the model 1a correspond to actual structures of patient's oral situation. As shown, the 3D surface boundary model 1a embodies anatomical structure representations of a patient's actual gum tissue 2, bone 3, and teeth (shown labeled as 11, 12, 13, 14, 15, 16 and 17 according to Federation Dentair Internationale (FDI) notation (a commonly used teeth numbering system in the dental industry), among other individual teeth (not labeled). In an embodiment, surface boundary model 1a is generated from the 3D volumetric structures represented in the volumetric density scan and extracted through image recognition and segmentation techniques, such as, thresholding the intensity values (measured in Hounsfield units) of individual scan elements in the radiograph stack. In an embodiment, surface boundary model 1a comprises a point cloud, a triangular or other polygonal mesh, or other 3D digital model.

FIG. 3B shows an example of a 3D surface model 1b generated based on a surface scan of the same anatomical area as FIG. 3A. Individual structures in the model 1b correspond to actual structures of patient's oral situation. As shown, the 3D surface model 1b embodies anatomical structure representations of a patient's actual gum tissue 2, and teeth (shown labeled as 11, 12, 13, 14, 15, 16 and 17 according to FDI notation. Since the bone in the patient's oral cavity lies beneath the surfaces of the gum and teeth, typically no bone information would be present in the surface scan model 1b.

Because the surface scan and the volumetric density scan are obtained from scanning the same oral areas of interest, both models 1a and 1b include respective model anatomical structures that represent certain same anatomical structure(s) (e.g., teeth 11, 12, 13, 14, 14, 15, 16 and 17, and gums 2) of the patient. Model 1b comprises a point cloud, a triangular or other polygonal mesh, or other 3D digital model, generated from the 3D surface structures represented in the surface scan.

As noted in FIGS. 3A and 3B, both the volumetric density scan model 1a and the surface scan model 1b are surface models of the (generally same) anatomical area. The 3D surface models 1a and 1b do not include representations of the internal anatomy. This means that neither model contains information about the sockets or other structure underneath the visible exterior surfaces of the objects in the model. In the illustrative example, where the object is a tooth, this means that one cannot ascertain the anatomy of the tooth socket which seats the tooth because the socket is not visible in either the 3D volumetric density scan model (FIG. 3A) or the 3D surface scan model (FIG. 3B).

In both models 1a in FIGS. 3A and 1b in FIG. 3B, only the crown portions of the teeth are modeled; neither scan model includes the anatomy of the root or socket which seats the tooth. Although the surface detail is helpful when planning dental treatment for a patient, for planning surgical treatment and designing prosthetics for the patient, the lack of subsurface information available in the models 1a, 1b pertaining to the patient's anatomy beneath the visible surfaces of the patient's oral cavity can hinder accurate planning and design.

To facilitate an accurate 3D socket model generation, in an embodiment each of the respective volumetric density scan data and the surface scan data from which the respective 3D surface models 1a and 1b are generated is submitted to a segmentation application. The segmentation application may be a remote service 244, or may be a local application (stored in local memory 204 and executed by one or more processor(s) 201. A segmentation processor processes each of the received surface scan data and volumetric density scan data to automatically recognize (via an image recognition function), extract and categorize individual recognized objects into labeled categories or classes (via a segmentation function).

For example, in an embodiment where the object is a tooth in a patient's oral cavity, the segmentation processor receives each of the intraoral surface scan data and the CBCT or other volumetric density scan data, and processes each of the scan data sets to recognize and label recognized objects as the individually identified teeth, gum, bone, and potentially other objects such as fillings, implants, etc. that are recognized in the received scan data. The segmentation processor tags recognized objects with corresponding object type labels associated with the object type (or classification) of the recognized object.

For example, the segmentation processor may recognize an object in the 3D model or scan data that corresponds to a tooth type 16 and assign to the recognized object an object type label "16" (or any unique label that classifies the recognized object as being of the unique object type corresponding to that patient's actual tooth 16). The segmentation processor recognizes and classifies (i.e., "labels") recognized data segments in the scan data into a plurality of individual segments and corresponding to various recognized object types.

Preferably, the individual segments comprise a 3D surface model representing the actual scanned object (e.g., a scanned tooth, portion of gums, bone, implant, etc.). In an embodiment, each segment corresponds to an individual object in the patient's oral cavity, and is labeled as such with an associated label. Each segment comprises a 3D model standing on its own, represented as a 3-dimensional triangular (or other polygonal) mesh.

Referring to FIG. 3C, a segmentation processor may recognize representations of individual teeth 11, 12, 13, 14, 15, 16, and 17 in the volumetric density scan of the patient, and may segment each recognized representation of any of tooth 11, 12, 13, 14, 15, 16, and 17, gums 2, and bone 3, into corresponding independent segments 11a, 12a, 13a, 14a, 15a, 16a, 17a, 2a, and 3a, collectively forming a segmented volumetric density scan surface model 10a. Each segment is converted to an independent surface mesh, for example a 3D triangle mesh, and each segment may be independently selected (for example when presenting the segmented model in a graphical user interface (GUI) as discussed hereinafter.

Notably, because the segments 11a-17a, 2a, 3a were extracted from the volumetric scan data, each segment includes the full available information from the volumetric density scan. This means that objects (such as nerve canals) and portions of objects (such as the tooth roots) that cannot be imaged in a surface scan due to lying beneath the visible surfaces inside and outside of the patient's mouth, are still modeled in the volumetric density scan segments. Each volumetric density scan segment includes full object information (based on what is imaged in the volumetric scan data), even below the surfaces of the scanned anatomical area of the patient. Thus, each of teeth 11a-17a include the root information, which is clearly visible in the segmented model.

Similarly, referring to FIG. 3D, a segmentation processor may recognize representations of individual teeth 11, 12, 13, 14, 15, 16, and 17 in the surface scan of the patient, and may segment each recognized representation of any of tooth 11, 12, 13, 14, 15, 16, and 17 and gums 2 into a corresponding independently selectable segment 11b, 12b, 13b, 14b, 15b, 16b, and 17b and 2b, collectively forming a segmented surface scan surface model 10b. Each segment is converted to an independent surface mesh, for example a 3D triangle mesh.

While the segmented model 10a includes all of the segments of the scanned anatomical area of the patient, each segment is an independently selectable 3d model of the corresponding scanned object. Accordingly, each segment 11b-17b, and 2b may be viewed alone, for example as shown in FIG. 3H (which shows tooth segment 16b alone corresponding to the patient's tooth 16). Tooth segment 16b includes only the portion of the tooth 16 that is present in the surface scan. Thus, tooth segment 16b represents only the crown of tooth 16 since only the crown (the portion of the tooth 16 that is above the gumline) is visible during the surface scan.

FIG. 3E shows the segmented volumetric density scan surface model 10a and segmented surface scan surface model 10b cross-mounted in a common 3-dimensional coordinate system. Independent imaging systems are typically used to capture each of the surface scan data and volumetric density scan data. For example, an intra-oral scanner (IOS) may be used to capture the surface scan of the patient's oral area of interest, while a CBCT scanner may be used to capture the patient's volumetric density scan. Both scans are valuable in providing important information, and together supplement one another to provide a more complete image of the patient's actual oral situation. Surface scanners (such as optical scanners) can capture very high-resolution details of the visual topography of the patient's dentition but can only capture surface details and not internal details.

In contrast, volumetric density scans (such as CT or CBCT scans) can capture internal volumetric and density details of the patient's dentition, such as dimensions and density of the jaw, complete teeth (including roots), and nerve pathways. Together the surface scan and volumetric density scan can form the foundation of a dental treatment planning and prosthesis manufacturing process.

Because the independent imaging systems capture image data relative to the specific 3D coordinate system of the imaging system capturing the scan, to cross-mount the scans within a single view pane with having its own 3D coordinate system, both scans must be aligned with each other. This process is often referred to as scan matching or registration. Methods exist for aligning 3D meshes into a single 3D coordinate system.

In an embodiment, each of the surface scan data and the volumetric density scan data is segmented into 3D triangular mesh segments corresponding to individual teeth and jaws, followed by key point determination of corresponding tooth segments from each of the surface scan and volumetric density scan for each tooth, followed by alignment of the key points in a common 3D coordinate system. This process may be performed, for example, using CoDiagnostix™ dental implant planning software, offered by Dental Wings, Inc. (a Straumann Group company).

Notably in FIG. 3E, the positions of the respective segments (11a, 12a, 13a, 14a, 15a, 16a, 17a, 2a and 11b, 12b, 13b, 14b, 15b, 16b, and 17b and 2b) from respective segmented models 10a and 10b correspond to the same respective actual anatomical structures (11, 12, 13, 14, 15, 16, 17 and 2) in the patient's mouth. As can be seen, it is very important that the segments corresponding to portions of the same actual anatomical structure from each scan type (e.g., internal or surface) are mounted in the same 3-dimensional coordinate system. When they are properly cross-mounted, segments representing the same actual anatomical structure substantially coincide, as shown.

In an embodiment, a segmentation processor processes the scan data to identify and classify portions of the scan data into individual segments classified into anatomical structure types based on a set of labeled training data that includes multiple instances of each of the anatomical structure types. In an embodiment, the segmentation processor is a trained convolutional neural network (CNN) that has been trained on a large data set of scan images obtained from a large number of different people with different anatomical structure situations that include, or have missing, different teeth, gums, bone, and other natural and artificial (e.g., implants, prostheses, etc.) anatomical structures.

FIG. 3F illustrates the problem encountered when a tooth scan segment 16b (see FIG. 3D) is removed from the surface scan. As illustrated, removal of the tooth crown segment 16b results in a hole 16c in the model 10b where the crown 16b used to be. This is to be expected since the segmented surface scan 3D model 10b is generated based only on the surface scan data, which contains no bone or other beneath-the-surface information such as the root information of the teeth. Thus, when the tooth segment 16b is selected from the segmented surface scan model 10b (see FIG. 3D) and removed, there is no socket information available, and the surface scan model 10b has only a hole 16c where the tooth segment 16b was prior to removal.

FIG. 3G shows the segmented surface scan 3D model after tooth segment 16b has been removed and the tooth segment 16a from the segmented volumetric density scan 3D model (from FIG. 3C) is co-mounted in the same 3D coordinate system. FIG. 3H shows the tooth segment 16a, separate and apart from the other segments of the volumetric density scan model 10b. Tooth segment 16a includes a crown portion $16a_c$ and a root portion $16a_r$. Notably, the root portion $16a_r$ of tooth 16 includes a trunk $16a_t$ and three individual roots (a lingual root $16a_{r\_l}$, a mesio buccal root $16a_{r\_mbs}$ (not visible in FIG. 3H), and a distal buccal root $16a_{r\_dbr}$). While the tooth 16 may have 3 individual roots, other teeth may have only one root, or may have two or additional roots. For simplification, the trunk and individual roots of any given tooth may herein collectively be referred to as "the root" of the tooth. Only the crown $16a_c$ is visible above the gumline in a surface scan. The root portion $16a_r$ is not visible above the gumline with the naked eye or to the cameras in an intraoral scanner.

FIG. 3I shows the individual tooth segment 16b (from the segmented surface scan 3D model 10b of FIG. 3G). As noted, the tooth segment 16B represents only the crown of the tooth 16 since only the crowns of the teeth are visible to the surface scan cameras (because they are above the gumline and can be seen with both the naked eye and also camera lense(s).

Notably, since both the surface scan and the volumetric density scan image the same area of interest, both scans include surface information pertaining to the same actual corresponding anatomical structures (assuming each scan scanned the same areas). This means that for the visible surfaces such as the crowns of the teeth, both the surface scan and the volumetric density scan will each include surface information or surface boundary information, respectively, pertaining to the crowns of the teeth.

Surface scans using optical sensors tend to produce much higher resolution images, resulting in surface 3D models with high detail. Volumetric density scans typically use modalities that either cannot be as accurate, or would be medically unsafe to make as accurate as an optical scan. For example, volumetric density scans generated using x-ray technologies including CT or CBCT modalities are based on x-ray radiation, and while highly accurate images could be obtained using a high dose of x-rays, to do so would be medically unsafe for the patient. Accordingly, CT and CBCT modalities used on patients are required to be set at very low levels of x-ray radiation to make them safer for humans. The tradeoff is that the accuracy of the images is lower. Accordingly, the crown surface data from the surface scan will generally include higher detail than the crown surface data from the volumetric density scan.

In order to generate a 3D model of the patient's oral situation after removal of a tooth, the application retains the root portion $16a_r$ of the volumetric density scan tooth segment 16a and removes the crown portion $16a_c$. To do this, the application determines the gumline around the volumetric density scan tooth segment 16b based on the points along the lower edge of the surface scan tooth segment 16b.

FIG. 3J shows the surface scan tooth segment 16a and the volumetric density scan tooth segment 16b cross-mounted (both displayed within the same 3D coordinate system). As shown, the gumline $16B_{gl}$ is the set of points corresponding to the lower edge of the surface scan tooth segment 16b.

Since the application knows the position of the gumline $16b_{gl}$, it calculates the crown portion $16a_c$ as all points on the same side of the gumline (also called a cut-line) that the surface scan tooth segment 16b lies within the particular 3D coordinate system of the application.

Put simply, the application removes all points of the volumetric density scan tooth segment 16a that coincide or substantially fall within the same volume of the 3D coordinate system area as the surface scan tooth segment 16b (i.e., the crown) does, i.e. the corresponding portions of the volumetric density scan tooth segment and the surface scan tooth segment are co-represented. Put even more simply, the root portion $16a_r$ is obtained by subtracting 16b from 16a (and removing any outlier points, if necessary).

FIG. 3K illustrates the root $16a_r$ upon removal of the crown portion $16a_c$ from the volumetric density scan tooth segment 16a. Since this is a surface model, only the exterior points of the segment are present in the 3D model; hence, when the crown portion $16a_c$ is removed from segment 16a, the inside $16a_{r\_interior}$ is empty. The shape and form of the root portion $16a_r$ is defined only by points on the outer surface of the tooth root $16a_r$ as defined from the surface model of the individual segments obtained from the volumetric density scan.

Accordingly, the contours of the inside of the root follow the contours of the exterior surface of the tooth root itself. The remaining root $16a_r$ may thus be displayed together with the surface model 10a (with the crown segment 16a removed) of FIG. 3F to generate a surface 3D model 10d representing the patient's oral situation with tooth 16 extracted. This is shown in FIGS. 3L, 3M, and 3N. FIG. 3L presents the 3D model 10d substantially along the horizontal plane with a view of the lingual side to show the hole 16c and socket contour 16s (represented by 16br as extracted from 16b). FIG. 3M shows the model 10d from another orientation, along the same horizontal plane as in FIG. 3I, viewed from the posterior side of the model. The socket contour is more visible from this point of view. FIG. 3N shows yet another view of the model 10d looking into the socket where the tooth 16 was virtually extracted. The contours of the socket 16s are visible, showing where two of the three individual root prongs were seated prior to virtual extraction of tooth 16.

The socket 10S includes the contours where the trunk $16B_t$, and each of individual roots were seated prior to the virtual tooth extraction. As illustrated, the socket 16s follows the contours of extracted tooth's root, including a trunk socket portion $16a_t$ and three individual root sockets including lingual root socket $16s_{r\_l}$, mesio buccal root socket $16s_{r\_mbs}$, and distal buccal root socket $16s_{r\_dbr}$, corresponding to lingual root $16a_{r\_l}$, mesio buccal root $16a_{r\_mbs}$, and distal buccal root $16a_{r\_dbr}$, respectively.

Because the volumetric density scan segment model of the tooth includes only the outer (boundary) surfaces of the tooth object, it contains no information about the interior of the tooth itself. That is, for segmentation, the segmentation processor produces a 3D mesh of outer surfaces of the tooth without including any modeling of the inside of the tooth. For closed objects, such as a tooth, the 3D mesh model is also a closed triangular mesh (the number of edges and triangular shaped facets associated with any given vertex is equal). Thus, because the inside of the severed root segment $16a_r$ (i.e., segment 16 with the crown portion $16a_c$ removed) is empty, the inside surfaces of the root segment $16a_r$ follow the same contours as the outside surfaces of the root segment $16A_r$. That is, the inside surfaces are merely the same exterior walls of the root segment $16a_r$ but viewed from the inside of the walls.

Removal of the crown portion $16a_c$ from the volumetric density scan segment $16a$ produces an open mesh (i.e., there exists at least one vertex in the mesh where the number edges associated with the vertex exceeds the number of triangular shaped facets associated that vertex). An edge facet as used herein is a facet whose number of adjacent facets (which share an edge) does not equal the number of edges of the facet. In the context of the removal of the crown portion $16a_c$ of the volumetric density scan segment $16a$, the remaining portion of the volumetric density scan segment $16a$, i.e., the severed root segment $16a_r$, includes a set of edge facets along the margin line (where the crown meets the gumline), making it an open mesh. Since there is no information inside the severed root segment $16a_r$, the inside surface of the open mesh is identical to exterior surface of the severed root segment $16a_r$.

A second aspect of the present disclosure refers to a virtual object extraction tool which incorporates the methodology of the 3D socket model generation described heretofore (for example in connection with FIGS. 3A-3N). Such virtual object extraction tool may be implemented in various anatomical treatment planning and design software tools.

For example, without limitation, in various embodiments, the virtual object extraction tool is determined and generated in connection with any and all of a virtual tooth extraction tool in a dental treatment planning software tool, in an implant planning software tool, and/or in a dental prosthesis design and manufacturing planning (CADCAM) software tool. For example, in a dental tooth extraction operation, the novel devices, systems, graphical user interfaces, computer-enabled tools, methods and processes herein presented allow a virtual tooth extraction of a patient's tooth to be performed virtually on an electronic display prior to actual extraction of the tooth from the patient.

The virtual tooth extraction tool allows a dental professional to view a highly accurate model that precisely represents the contours of the actual socket that seats the object and that will remain and be exposed after removal of the object from the patient's mouth. The socket model may be generated and displayed (along with the surrounding area of the patient's oral cavity) after virtual removal of the targeted extraction tooth. The contours of the socket are accurately represented and the inside of the socket conforms to outer shape, below the gum line (i.e., margin line), of the exterior surface of the patient's actual tooth (including the root(s)).

The socket model may be used to perform a virtual object extraction, whereby a targeted extraction object (such as a tooth) may be removed from a 3D model of the anatomical area of interest and a virtual 3D socket model is added to the model (or made available for display with the model). Display of the 3D model with the object removed and the virtual socket made visible is in itself instructive for use in actual object extraction from a patient's anatomy. It is further useful in subsequent treatment planning, such as dental implant planning and prosthetic design planning, discussed hereinafter.

Figure 4:
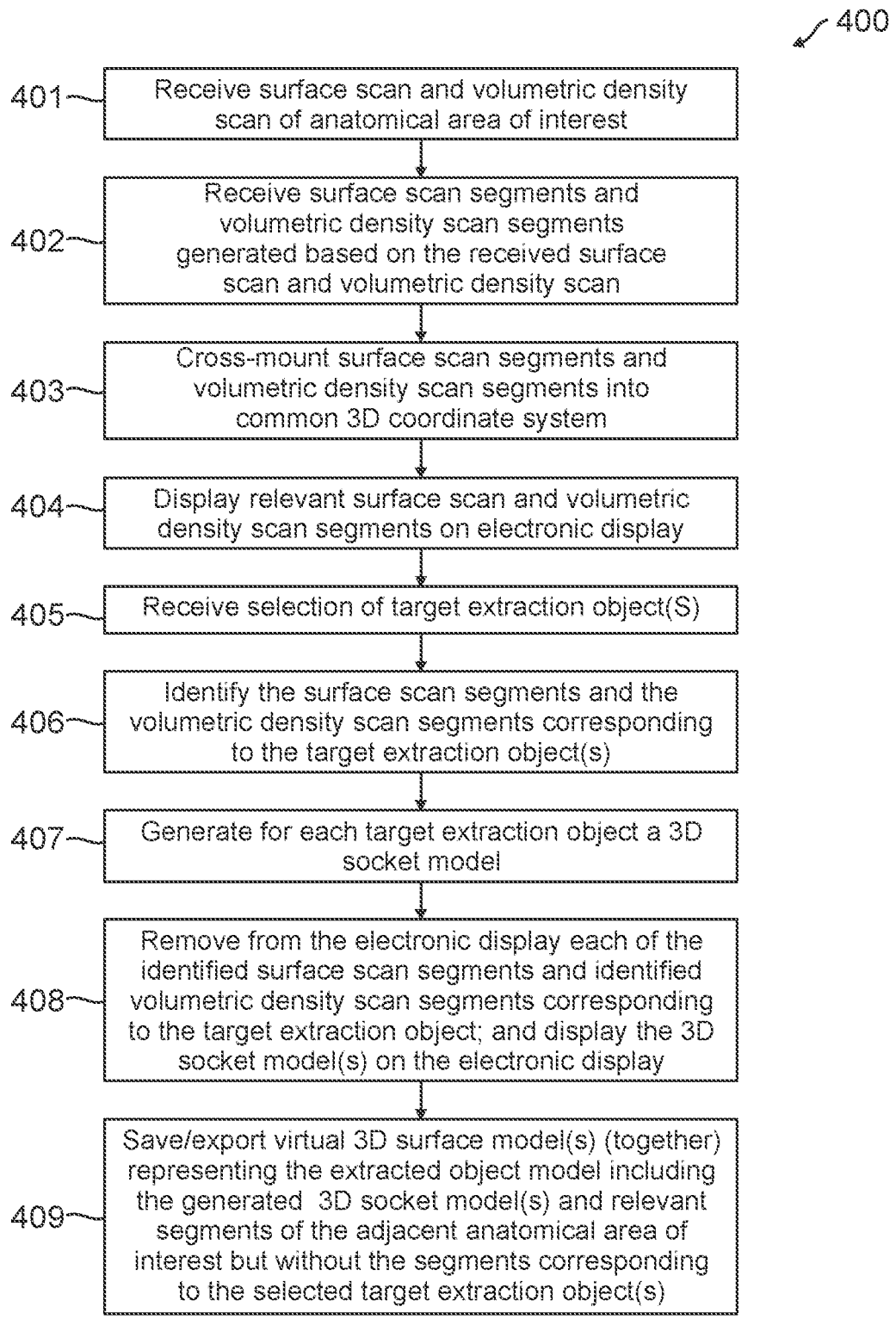
FIG. 4 represents a flow diagram outlining a second aspect of the method according to an embodiment of the present disclosure.

With reference to FIG. 4, a virtual object extraction method 400 may comprise a step 401 of receiving a surface scan and a volumetric density scan of an anatomical area of interest, and a step 402 of receiving surface scan segments and volumetric density scan segments corresponding to objects recognized in the surface scan and the volumetric density scan of the anatomical area of interest. Steps 401 and 402 may occur outside of the execution of the application, or may be an integral part of the application, similar to the discussion of steps 101 and 102 in connection with the method of FIG. 1.

The method 400 may further comprise a step 403 of cross-mounting the surface scan segments and the volumetric density scan segments into a common 3D coordinate system. In a step 404, the method comprises displaying on an electronic display at least the cross-mounted segments associated with the targeted extraction object and adjacent cross-mounted segments of interest. In a step 405, the method comprises receiving a selection of one or more target extraction object(s). In a step 406, the method comprises identifying the surface scan segments and the volumetric density scan segments associated with the selected objects of interest. In a step 407, the method comprises, for each selected target extraction object, generating a 3D socket model corresponding to the selected target extraction object.

Method 400 may further comprise a step 408 of removing from the display each of the identified surface scan segment(s) and volumetric density scan segment(s) corresponding to the selected target extraction object(s), and a step 409 of displaying the generated 3D socket model(s) on the electronic display. Method 400 may further comprise a step 409 of saving and/or exporting a 3D surface model representing the extracted tooth model including the generated 3D socket model(s) and relevant segments of the anatomical area of interest but without the segments corresponding to the selected target extraction object(s).

The functionality of any of steps 401, 401, 403, 405, 406 and 407 may be implemented as described in connection with respective steps 101, 102, 103, 104, 105 and 106 of FIG. 1, or may be implemented by a call to a 3D model generation tool (215a in FIG. 2) which performs the functionality of the relevant method steps of FIG. 1 and returns the generated 3D socket model(s) to the tool executing method 400.

Method 400 may be implemented as a computer-enabled virtual object extraction application 215b executing in a system such as system 200 of shown in FIG. 2. Various aspects of the virtual object extraction application 215b may be implemented as computer instructions which may be stored in local memory 204 of system 200 and which, when executed by the processor(s) 201, may implement features and aspects of method 400.

The computer instructions may include instructions implementing a graphical user interface (GUI), which may include a user-facing (or "front-end") graphical user interface environment and an underlying operational (or "back-end") GUI which executes the functionality to effect operations indicated by user input received via GUI environment controls. The front-end GUI includes input controls through which user control, input and data is received via input device(s) 207, and through which patient data may be loaded into the environment. The front-end GUI further includes output display areas, such as user control elements and view panes, where user controls, various views of scan data and models, and other information, are displayed and output via output device(s) 208, 209 based on GUI control settings and user input to such controls.

FIGS. 5A-5D illustrate an exemplary embodiment of a graphical user interface (GUI) display environment 500 during various steps in a dental treatment planning workflow. The GUI display environment may be displayed on an electronic display 209 of a system 200 which implements a dental treatment planning application 215b. The GUI display environment 500 includes control(s) 501 (not individually shown) to allow a user to select and load a patient's scan data 220 into bulk memory 206 of the system 200 or on an external memory device (not shown) accessible through the system 200 or which is accessible from a remote service 212 via network adapter(s) 211.

In the context of the described aspects of the present disclosure, scan data 220 includes surface scan data and volumetric density scan data of an anatomical area of interest of a patient. In an embodiment, both the surface scan and the volumetric density scan are obtained before the dental treatment planning application is activated; in other embodiments, one or both of the surface scan data and volumetric density scan data are obtained in conjunction with use of the application 215b.

For example, a remote service 212 may include an optical scanner application in communication with an optical scanner, and which communicates the optical scan data to the dental treatment planning application during or after completion of an intraoral scan of the areas of interest in the patient's oral situation. Similarly, a remote service 212 may include a volumetric density scanner application in communication with volumetric density scanner, and which communicates the volumetric density scan data to the application 215b during or after completion of an intraoral scan of the areas of interest in the patient's oral situation.

Application 215a manages the display of the graphical content in the GUI display environment 500, including monitoring user input to the graphical controls received through user input device(s), such as a mouse, keyboard, joystick, voice recognition, etc. User input may correspond to actions to be taken, such as invoking various application functions specific to the substantive features of the application or GUI functions for changing the layout or content of the features displayed on the display. More particularly, the front-end GUI displays user input controls and monitors user input associated with the functional controls. Upon receipt of user input associated with a user input control, the GUI invokes an appropriate function corresponding to the particular user input control and type and content of the user input. The GUI is also responsive to the backend process(es) which communicate with the back-end GUI, which in turn communicates with the front-end GUI to display, remove from display, and/or modify display of, information on the electronic display.

Such user selected functions may result in, without limitation, displaying, removing from display, and modifying display of: models, views, segments, and/or annotations, and displaying, removing from display, and updating the look of, various user controls and information displayed in the GUI display environment 500, and receiving and returning information to facilitate substantive functional features of the application 215b, including but not limited to: substantive treatment evaluation, substantive treatment planning, virtual performance of treatment or operations (such as tooth extraction, implant placement, prosthetic design and placement, etc.

Figure 5A:
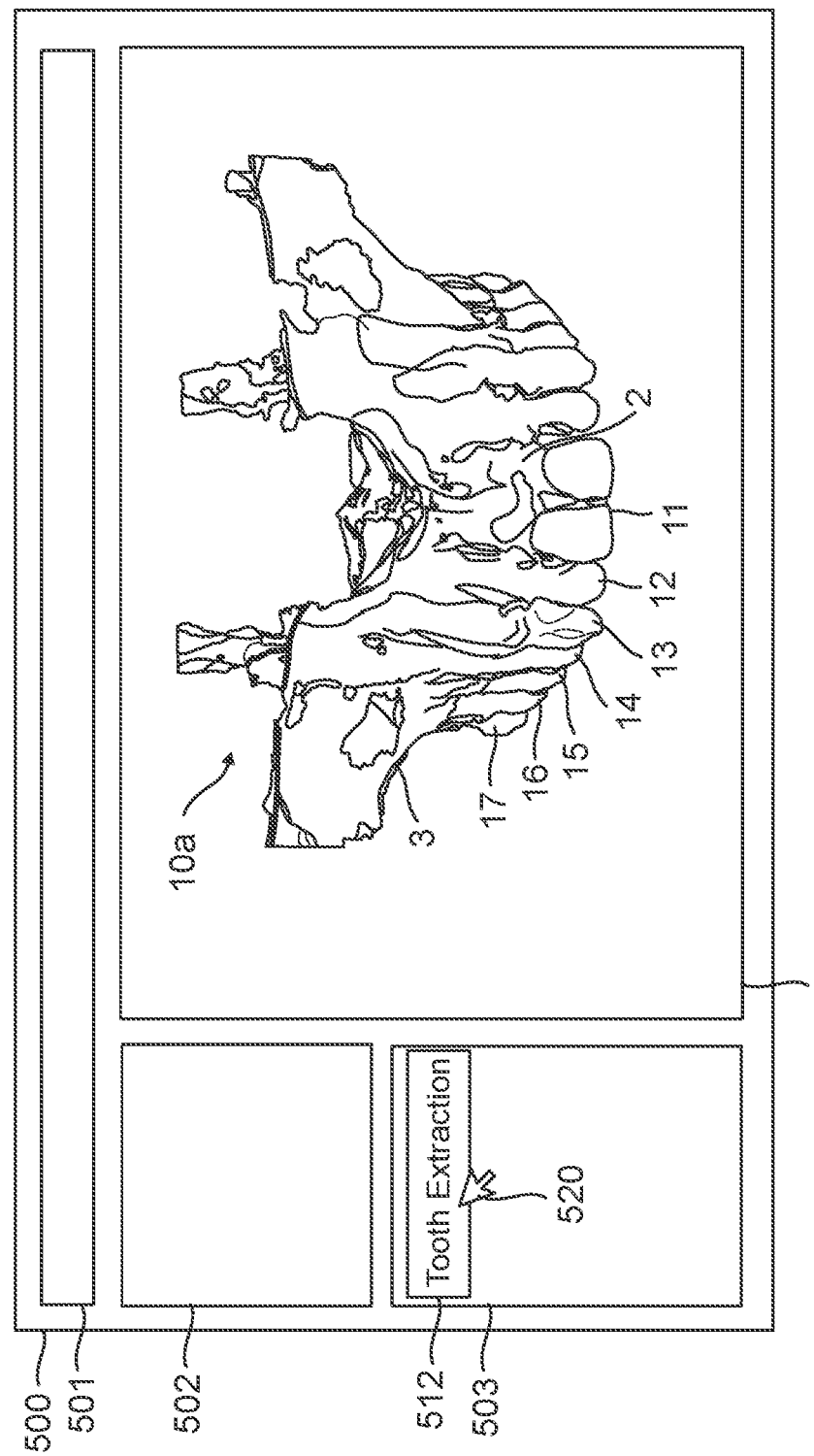
FIGS. 5A-5D depict a first exemplary graphical user interface implementation of various aspects of the present disclosure.

Referring to FIG. 5A, the GUI display environment 500 includes global controls 501 such as file management, generic display controls, and other controls that are generic to the GUI display environment. For example, controls 501 may include file selection controls, file save/export controls, view pane format controls, etc. GUI display environment 500 also includes patient-data specific controls 502, such as arch and individual tooth model controls.

GUI display environment 500 includes functional controls 503, including a tooth extraction control 512. Tooth extraction control 512 is shown generically as a single control, but may comprises a plurality of controls such as guided dialog of pop-up display panels or other well-known GUI interactive techniques for displaying information and requests for information and for receiving user input. GUI 500 also includes and displays at least one view pane 503 for displaying therein a 3-dimensional model of a selected patient's 3D anatomical model of the patient's oral situation (or selected portions thereof), as obtained from the patient's scan data and as selected via selection controls in controls 502.

Controls 501 include one or more control(s) (not shown) which when selected, allows user selection of a patient's surface and volumetric density scan data 220 from local, bulk or remote memory into the bulk memory 206 of the system 200. In an embodiment, when patient scan data 220 is initially loaded, the GUI display environment 500 may display one or a plurality of view panes 503 (only one shown) in order to present on the display a visual overview of the patient's oral situation. In FIG. 5A, view pane 503 is shown displaying a 3D model 10A of the volumetric density scan. Environment 500 may also include various additional views of the patient's oral situation based on the volumetric density scan data. For example, environment 500 may include a panoramic view pane, an axial view pane, cross-sectional view panes, and a tangential view pane (not shown).

An important objective of virtual tooth extraction tool, accessible via control 512, is to virtually represent the patient's oral situation upon virtual removal of one or more teeth or other objects selected for extraction. For example, in a dental treatment application 215b when a tooth is virtually removed and displayed within the GUI display environment 500, the resulting displayed 3D model should include a representation of the tooth socket that become visible to the naked eye upon removal of the target extraction tooth.

Previously, dental treatment planning applications and dental prosthesis design software (such as dental CAD/CAM) software, were unable to provide a detailed accurate of a socket of a removed tooth because the object surface models generated from scan data did not include subsurface information. In contrast to prior art dental treatment planning and/or dental prosthetic computer aided design (CAD) and computer aided manufacture (CAM) tools, the virtual tooth extraction tool extracts information from both a surface scan and an volumetric density scan of the patient's dentition, and utilizes the information corresponding to the same targeted tooth from both scan types to automatically determine and provide a highly accurate anatomically-based representation of the socket left behind upon removal of the tooth. The application 215b provides a virtual tooth extraction tool (activated via control 512) that automatically determines the contours of the socket of the selected tooth that is targeted for removal and generates a virtual 3D model of the socket for display, saving, and/or extraction.

Figure 5B:
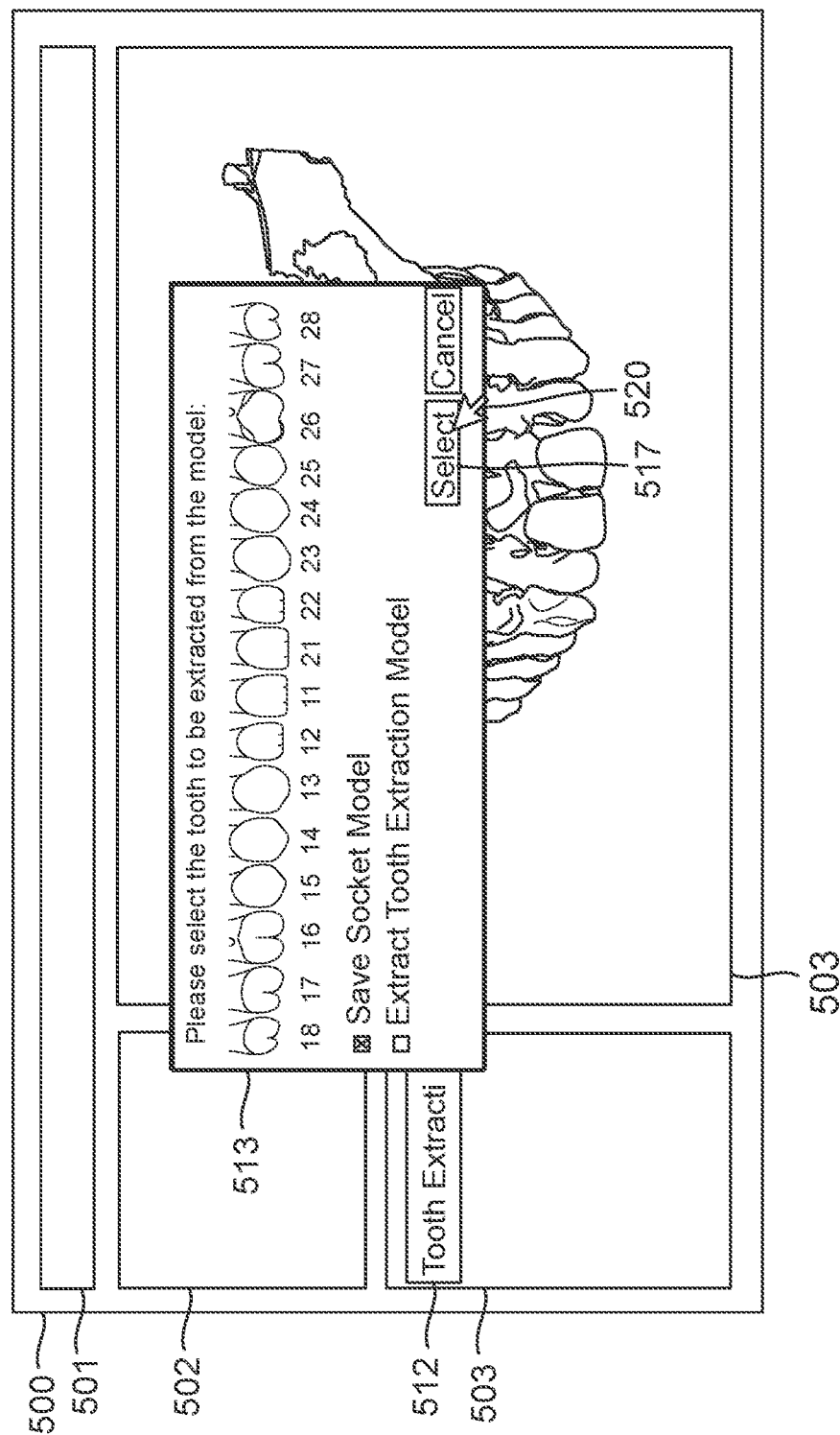

As shown in FIG. 5A, a user can activate the virtual tooth extraction tool by selecting the tooth extraction control 512 by moving, via a mouse (not shown), a graphical cursor 520 over the control 512 and mouse-clicking on the control 512. FIG. 5B shows an embodiment of a popup dialog 513 that is displayed in the GUI environment 500 when the Tooth Extraction control 512 is activated. As illustrated, the dialog may include a tooth selection map that allows a user of the application 215b to select one or more individual teeth for virtual tooth extraction.

In an embodiment, the user may click on the individual teeth in the chart to select such teeth as a target extraction tooth. The user can optionally select, by selecting a respective selection click-box or radio button or other such selection feature, an instruction to save the socket model generated by the tool upon generation of the socket and/or an instruction to extract the tooth extraction model (which contains the model in the view pane 503 less the target extraction tooth/teeth plus the generated socket models for such target extraction tooth/theeth. When the user is done selection the target extraction tooth/teeth and save/extraction options, the user can click on the Select button 517 to invoke the tooth extraction tool.

Figure 5C:
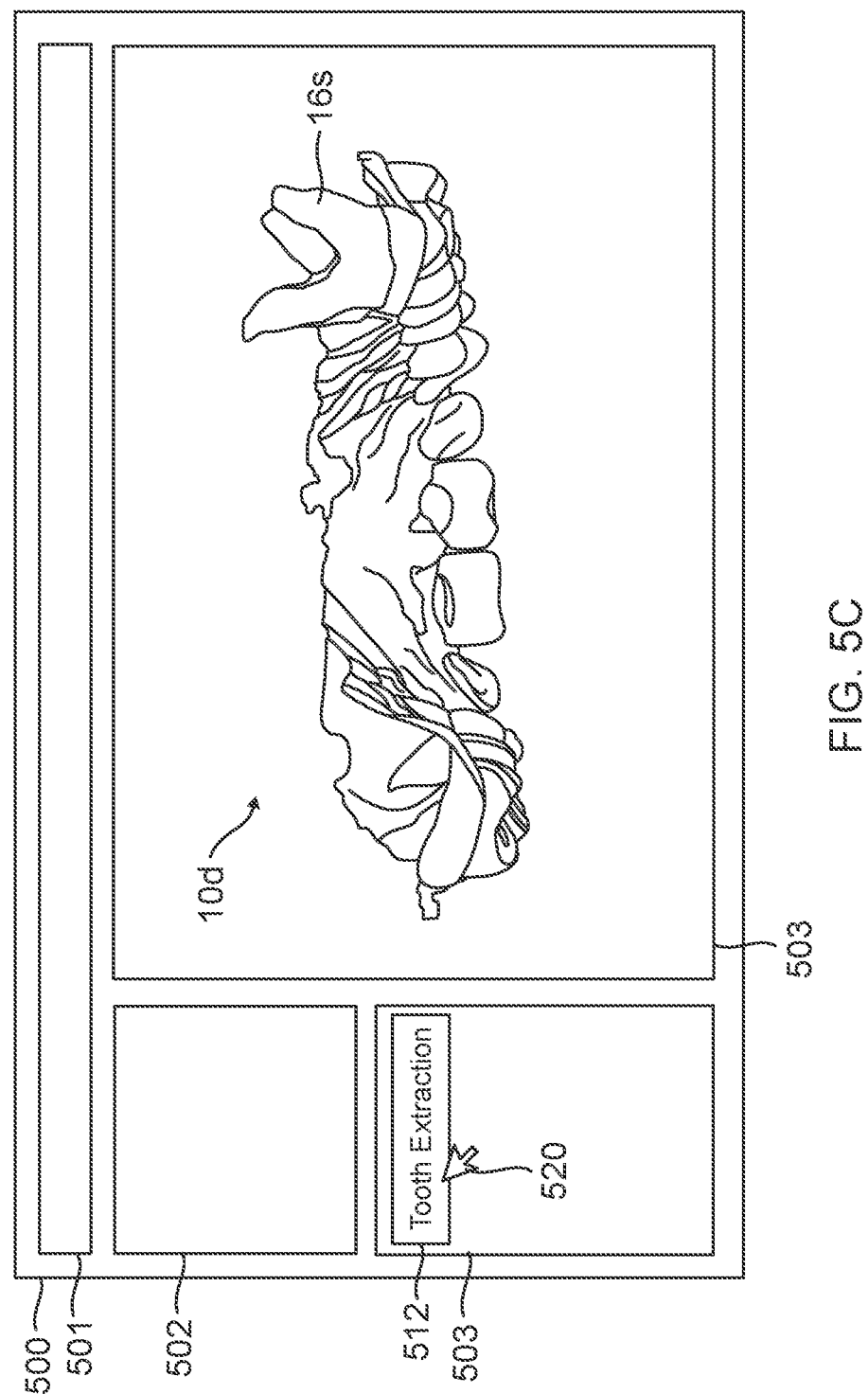
Figure 5D:
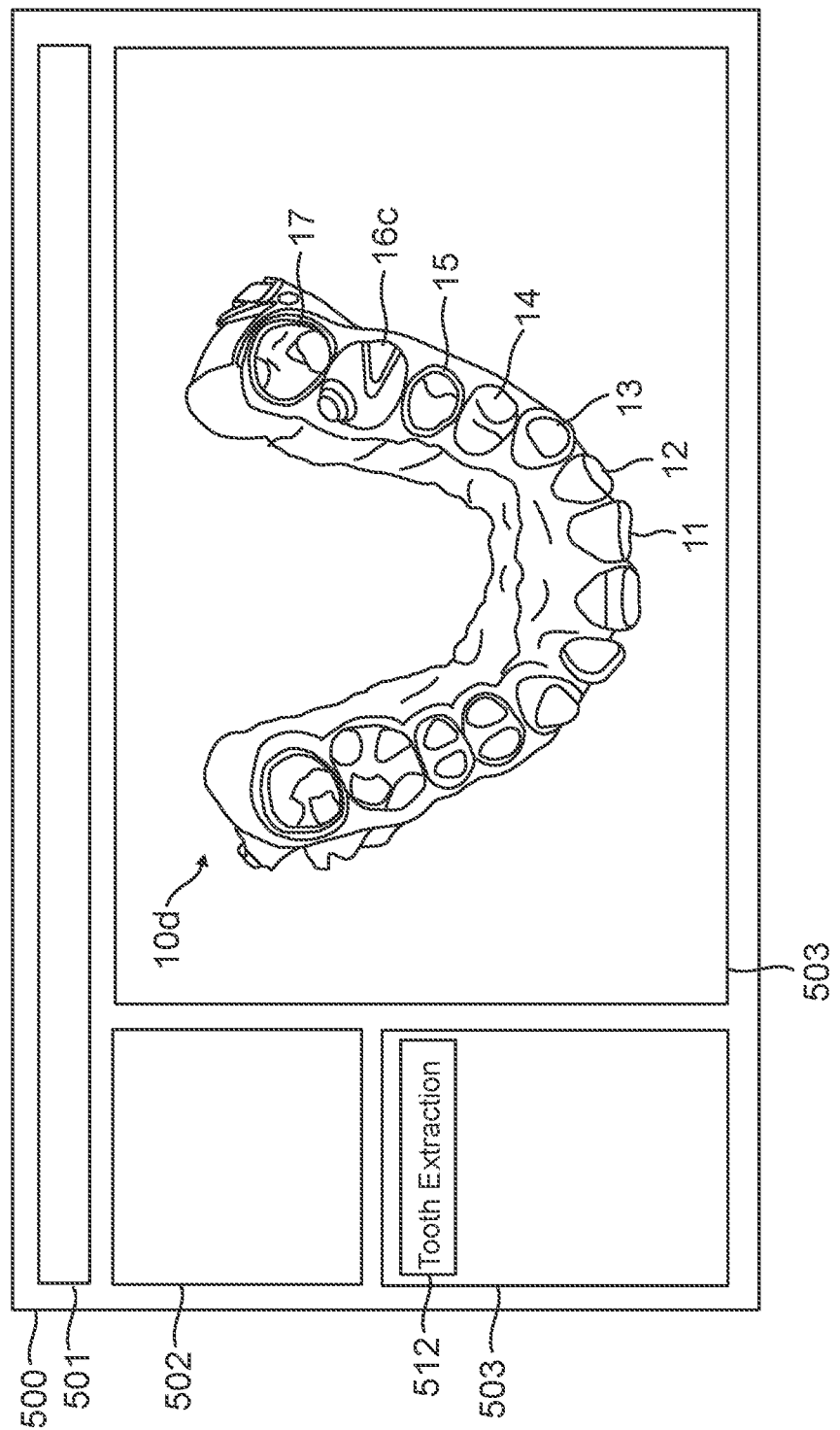

FIG. 5C presents a posterior view (looking at the maxilla arch from the back towards the front of the patient) of the 3D tooth extraction model 10D, which more conveniently shows the 3D socket model 16S corresponding to the socket from which the tooth 16 is extracted. The socket model 16S is displayed together with the 3D surface scan model with the tooth 16 extracted. FIG. 5D shows the same model 10D from the inferior view (from the bottom looking up toward the maxilla). As illustrated, the tooth 16 is missing, but the interior 16c of the socket 16S is visible and it follows the contours of the root(s) of the extracted tooth 16.

Figure 6:
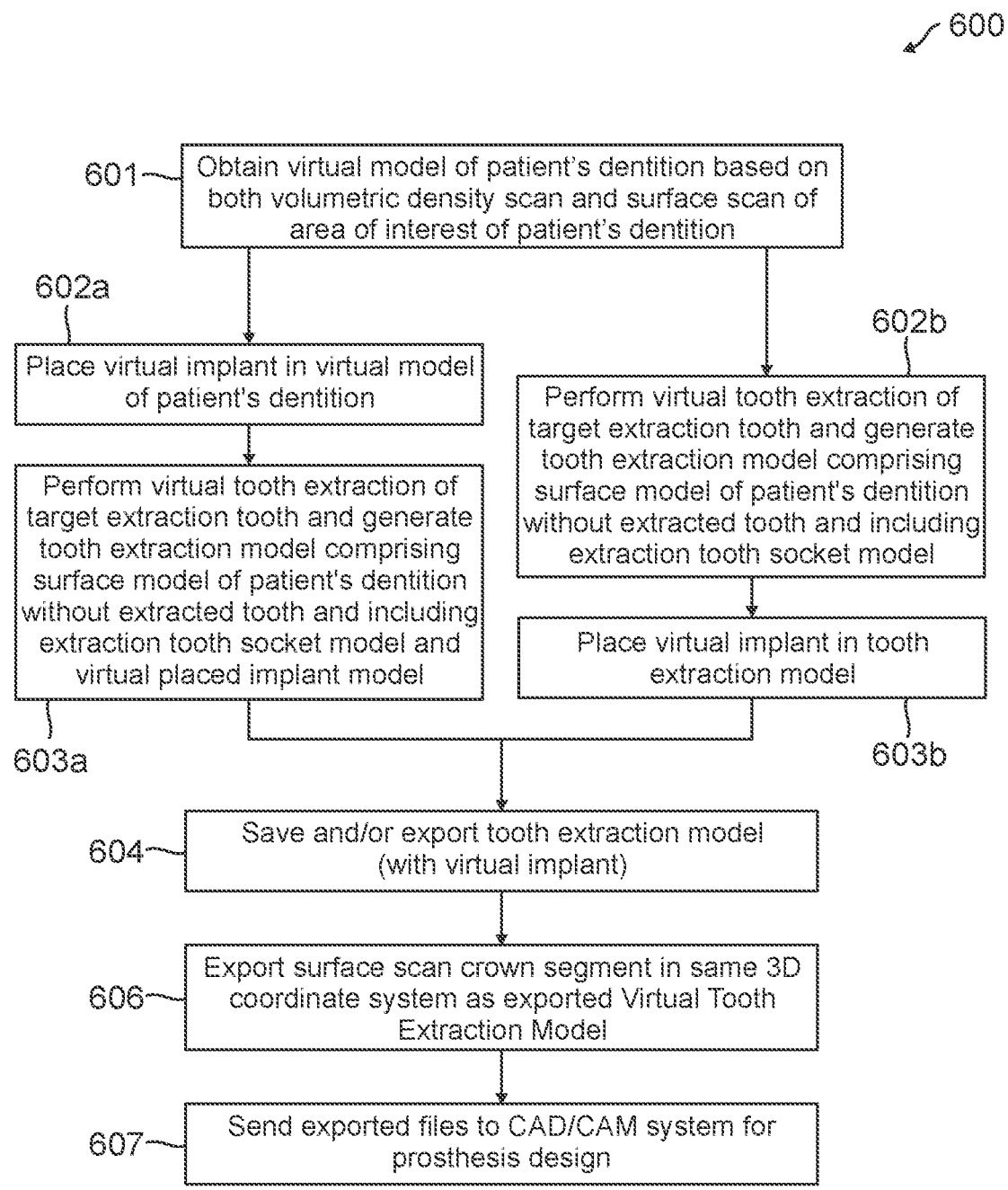
FIG. 6 represents a flow diagram outlining a third aspect of the method according to an embodiment of the present disclosure.

Virtual tooth extraction is often a precursor to the placement of a dental implant. FIG. 6 is thus shows a flowchart of an exemplary method 600 of a third aspect of the present disclosure, namely for generating a surface model with a tooth extraction model with an implant placed in the socket of the virtually extracted tooth. In accordance with the method 600, in a step 601 a dental implant planning application, such as an application 215c executing in a system 200 of FIG. 2, obtains a virtual model of a patient's dentition based on both volumetric density scan and surface scan of area of interest of patient's dentition.

In an embodiment, in a step 602a the dental implant planning application 215c places, under control of user input received through GUI controls, a virtual implant in the virtual model of the patient's dentition. In a step 603a, the dental implant planning application 215c performs, upon activation by a user of a tooth extraction control, a virtual tooth extraction of the tooth targeted for replacement by the implant, resulting in generation of an extraction tooth socket model, and a tooth extraction model wherein the target extraction tooth is removed from the virtual model of the patient's dentition and replaced with the generated extraction tooth socket model. Since the virtual implant is already in the virtual model of the patient's dentition, the tooth extraction model includes both the extraction tooth socket model and the virtually placed implant model.

In an alternative embodiment, steps 602a and 603a are reversed. In this alternative embodiment, in a step 602b the tooth extraction is performed first to generate the tooth extraction model. In a step 603b, the virtual implant is placed in the tooth extraction model. The virtual tooth extraction model may then be saved and/or exported to a file (step 604). Optionally, a surface scan crown segment is exported in the same 3D coordinate system as the exported tooth extraction model (step 605).

Optionally, in a step 606 the exported tooth extraction model and tooth crown segment file(s) may be sent to a prosthesis design tool for importation and design of an implant prosthesis.

Implant placement planning is often performed by pre-planning the selection of, and virtual placement of an implant in a virtual model of the patient's dentition. Virtual implant planning and placement may be performed using a dental implant planning tool, several of which exist in the market. An example is CoDiagnostix® Dental Implant Planning Software, offered by Dental Wings, Inc. (a Straumann Group company). Such dental implant planning software includes software-implemented tools, including a graphical user interface for importation and display of a patient's internal and surface scans, selection of dental implants, and placement of selected dental implant(s) in a model of the patient's dentition generated based on the imported scan(s).

Figure 7A:
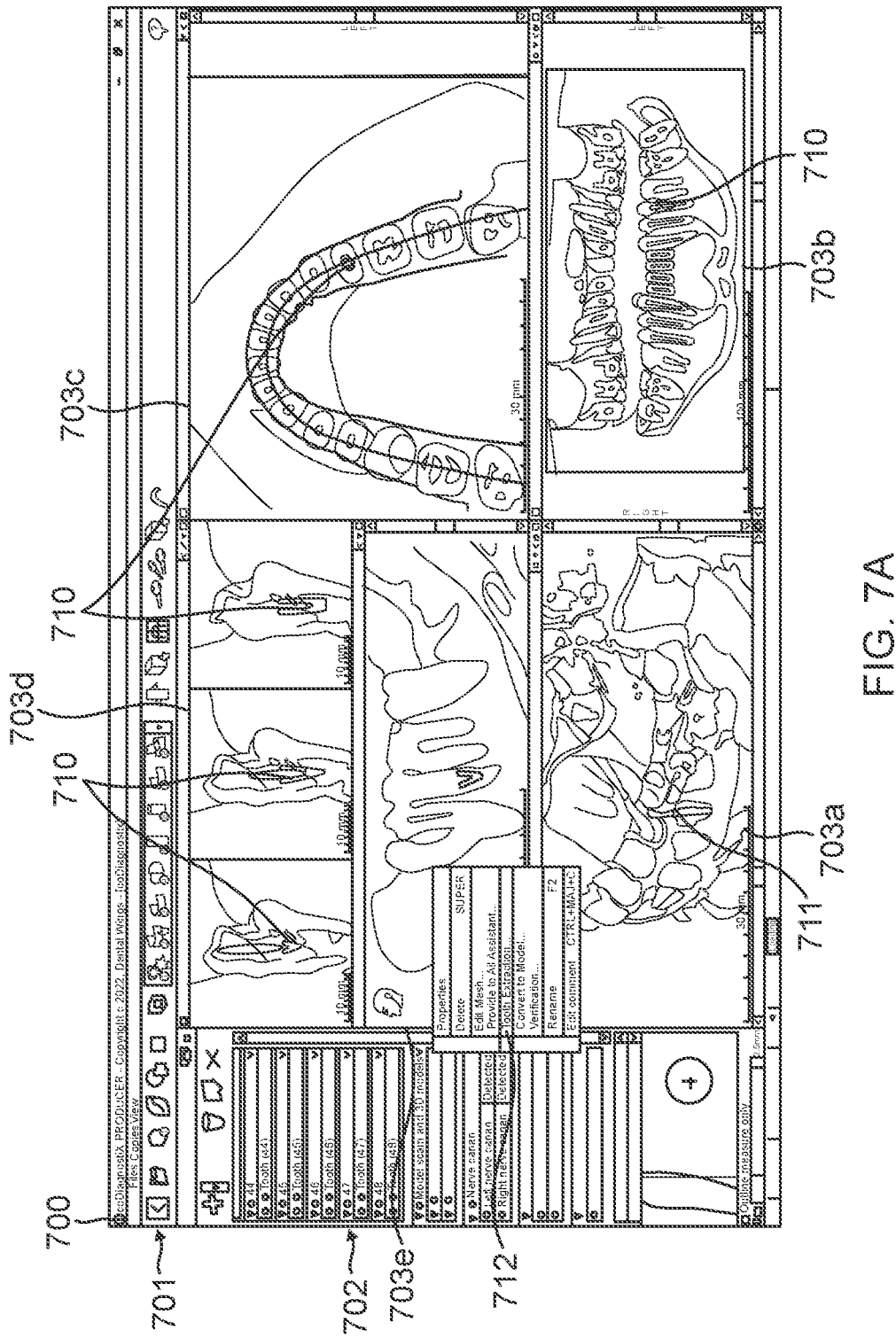

For example, FIG. 7A depicts a GUI display environment 700 generated by an application (such as application 215c in FIG. 2) in which a patient's surface and volumetric density scans have been imported and loaded into memory 206 of the system 200. FIG. 7A depicts the patient's dental situation after a dental professional has selected and virtually placed an implant. Techniques for virtually placing the implant in a virtual model of a patient's dentition are already known in the art, for example according to the use of CoDiagnostix® Dental Implant Planning Software. In FIG. 7A, a virtual implant post 710 has been placed and is shown in various types of views in corresponding view panes of the graphical environment 700. In the example shown, implant post 710 is shown virtually placed in a cross-sectional view (view pane 703d, an axial view (view pane 703c), a panoramic view (view pane 703b), a tangential view (view pane 703e), and a 3D view (view pane 703a).

As shown in the various views in panes 703a through 703e, the placement of the implant is represented by the placement of an implant post or screw 710, which is the base portion of the full implant. A full implant includes an implant post 710, an abutment (not shown) that attaches to the implant post 710, and an abutment for a prosthesis or tooth restoration (also not shown), which may be a crown, bridge, or denture.

At the initial planning stage, only the implant post 710 need be virtually placed. The implant planning software application provides virtual implant placement guide(s) 711, which do not correspond to a physical component-they are visual indicators only that assist the dental professional in placing the implant at the correct angle. In FIG. 7A, the virtual guides 711 appear in the 3D view pane 703a as a long cylindrical rod with a central axis coincident with the central axis of the implant post 710 and having a diameter corresponding to the diameter of the abutment attachment socket inside the implant post. Preferably, the cylinder of the virtual implant placement guide 711 extends along the central axis above the occlusal plane of the teeth, such that the cylinder length is much longer than the cylinder diameter. Preferably, the guide 711 is displayed in a contrasting color to the colors used in the 3D model and other view panes so that the application user can immediately see the guide relative to the content in each view pane.

GUI display environment 700 includes a tooth extraction control 712, accessed in the exemplary embodiment by selecting a control from the view pane display controls 702 which corresponds to the portion of the patient's dentition in which the implant under consideration is placed. In the embodiment shown, the dental professional selects the lower arch control, right clicks on it to pull up a context menu and selects a tooth extraction control 712 from the context menu. The tooth extraction control may be selected to instruct the dental treatment planning application to automatically perform a virtual tooth extraction (using the principles described hereinabove). There exist many ways to implement the control that invokes the automated virtual tooth extraction tool—the key is to provide one or more controls that allow the user to invoke the tooth extraction workflow.

Figure 7B:
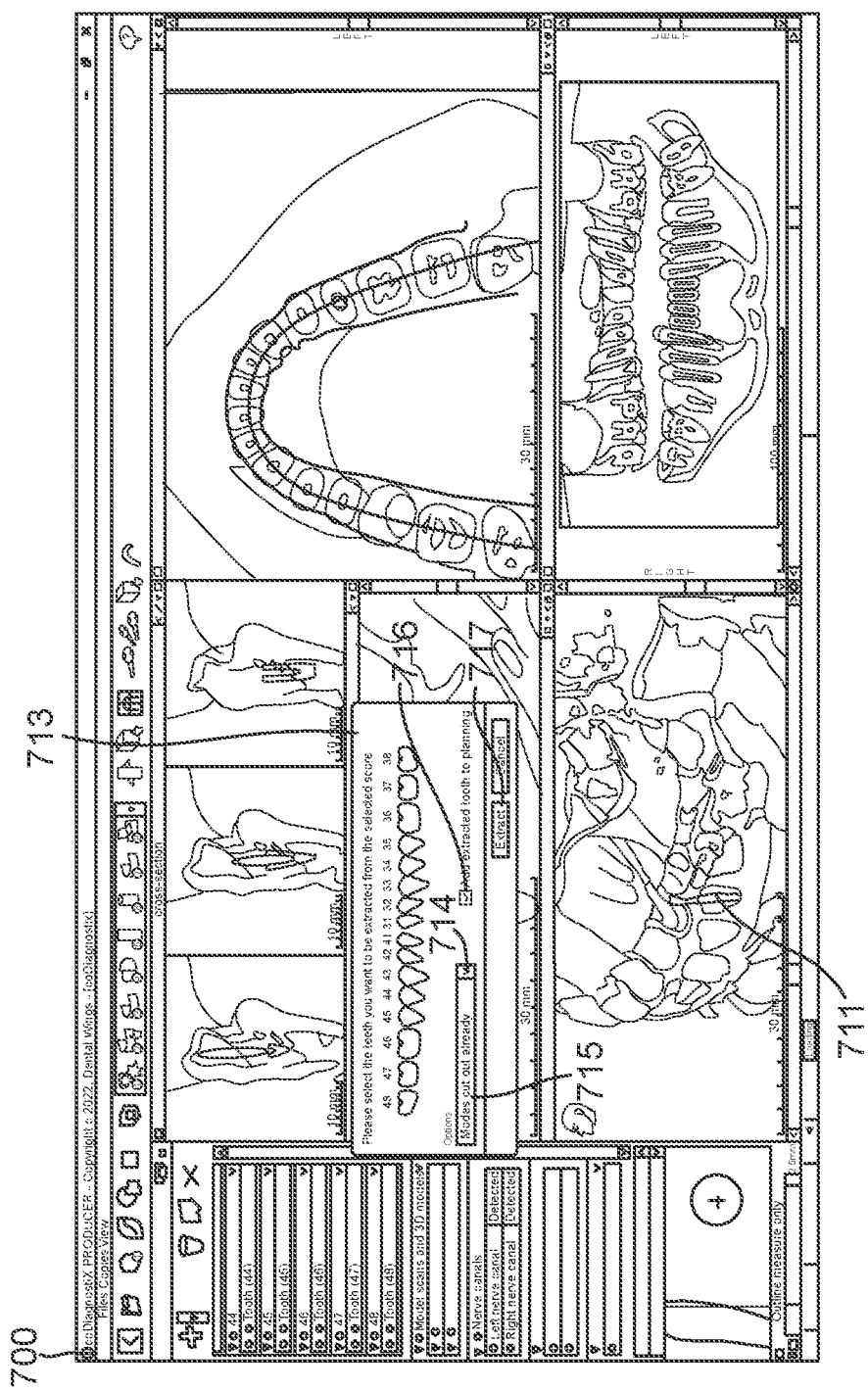

FIG. 7B illustrates a popup window 713 that appears in the GUI display environment 700 when the user selects the Tooth Extraction control 712. The popup window presents several options and user input controls for obtaining the inputs required by the virtual tooth extraction tool, including a tooth selection control 718, a mode control 714. In the embodiment shown in FIG. 7B, the tooth selection control 718 displays a set of selectable teeth icons corresponding to teeth in the selection portion of the patient's dentition as selected by the user in FIG. 7A. The user (i.e., the dental professional), may select the tooth corresponding to the tooth with the virtual implant post 710 is placed. In the example, the user selects tooth 35 corresponding to the tooth on the lower arch left side where the virtual implant post 710 is placed. For the mode, the user selects the "Mode: Cut out alveolus" 715 from the Options drop down menu 714, checks the check box control 716 to indicate that the extracted tooth should be saved as a separate file for future planning, and invokes the virtual tooth extraction tool by clicking on the Extract control 717.

Figure 7C:
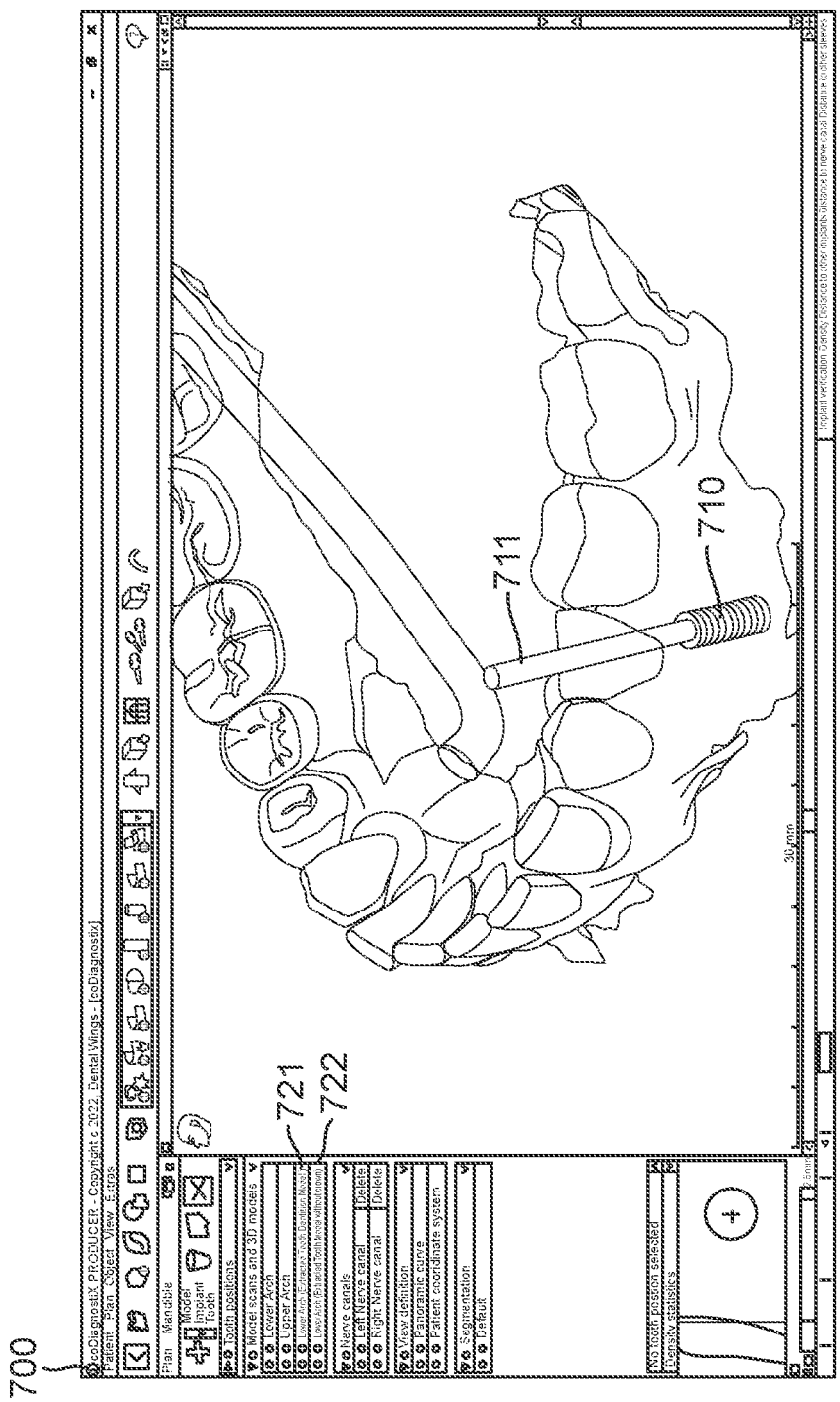

FIG. 7C shows a 3D surface model of the patient's dentition in view pane 703a. Upon completion, the virtual tooth extraction tool adds two 3D model files to the list of available model scans and 3D models in the controls section 702 of the GUI display environment 700. The user can select these files to display them in the pane 403a. One file is an extracted tooth dentition model (indicated at 721 in the file list). The extracted tooth model is created by the virtual tooth extraction tool according to the techniques described in connection with FIGS. 1 and 4, the extracted tooth model is a 3D surface model of the patient's dentition (including the previously placed implant post 310) with the selected tooth 35 removed from the model and a socket generated and included in the model in its place.

The second file is an extracted tooth model (indicated at 722) in the files list, and is a model of the tooth 35, where the crown has been removed from the root.

Figure 7D:
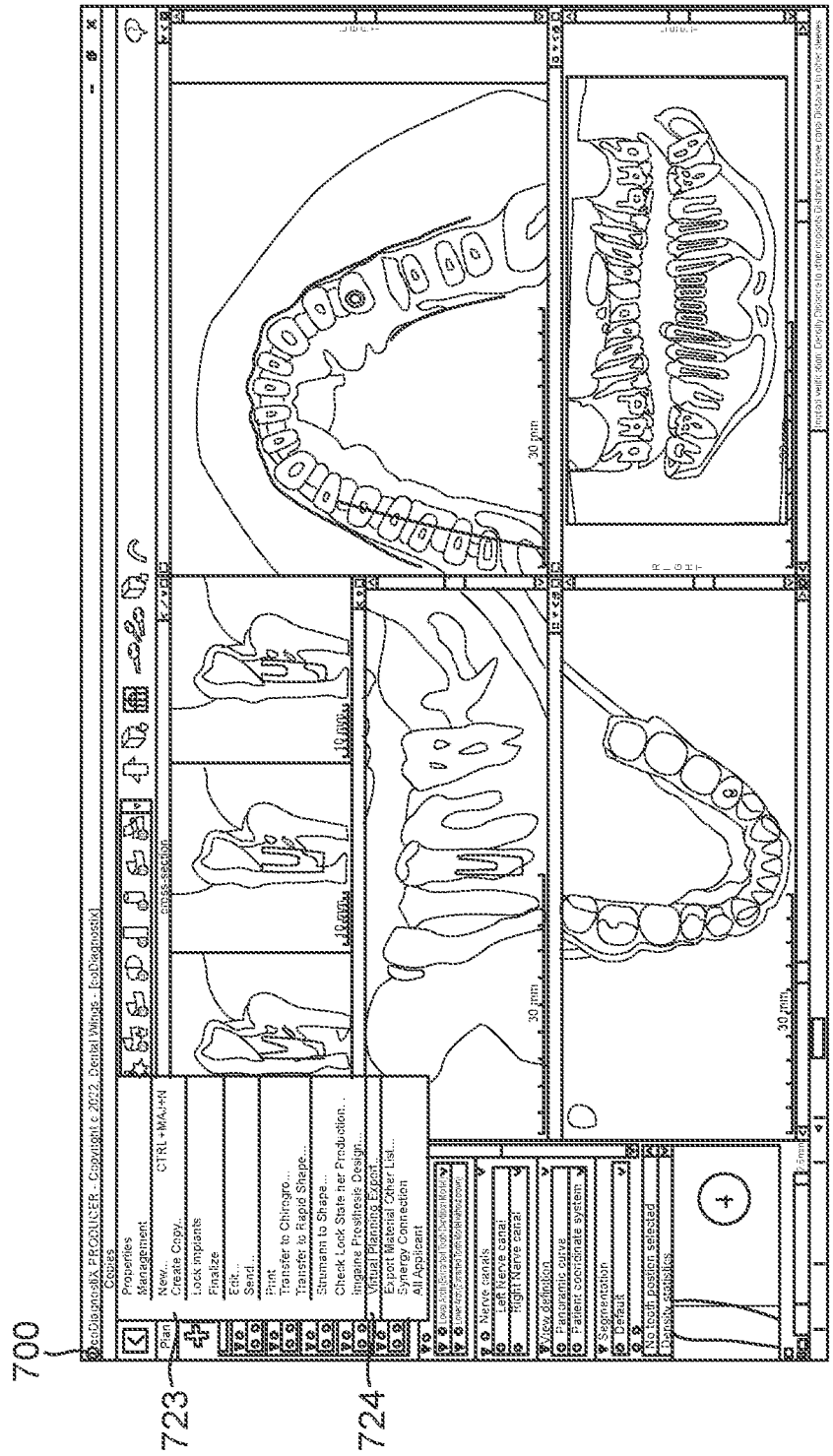
Figure 7E:
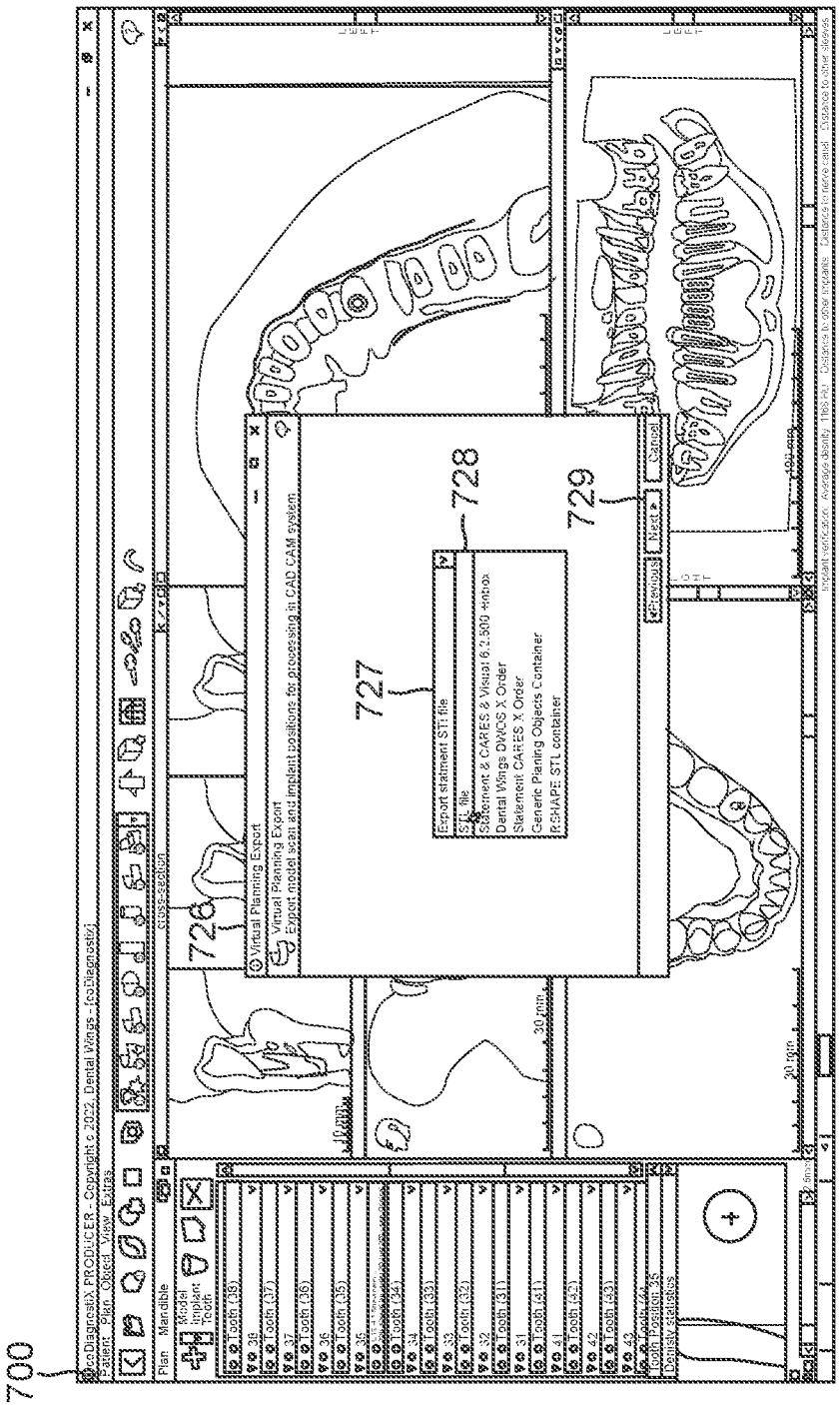
Figure 7F:
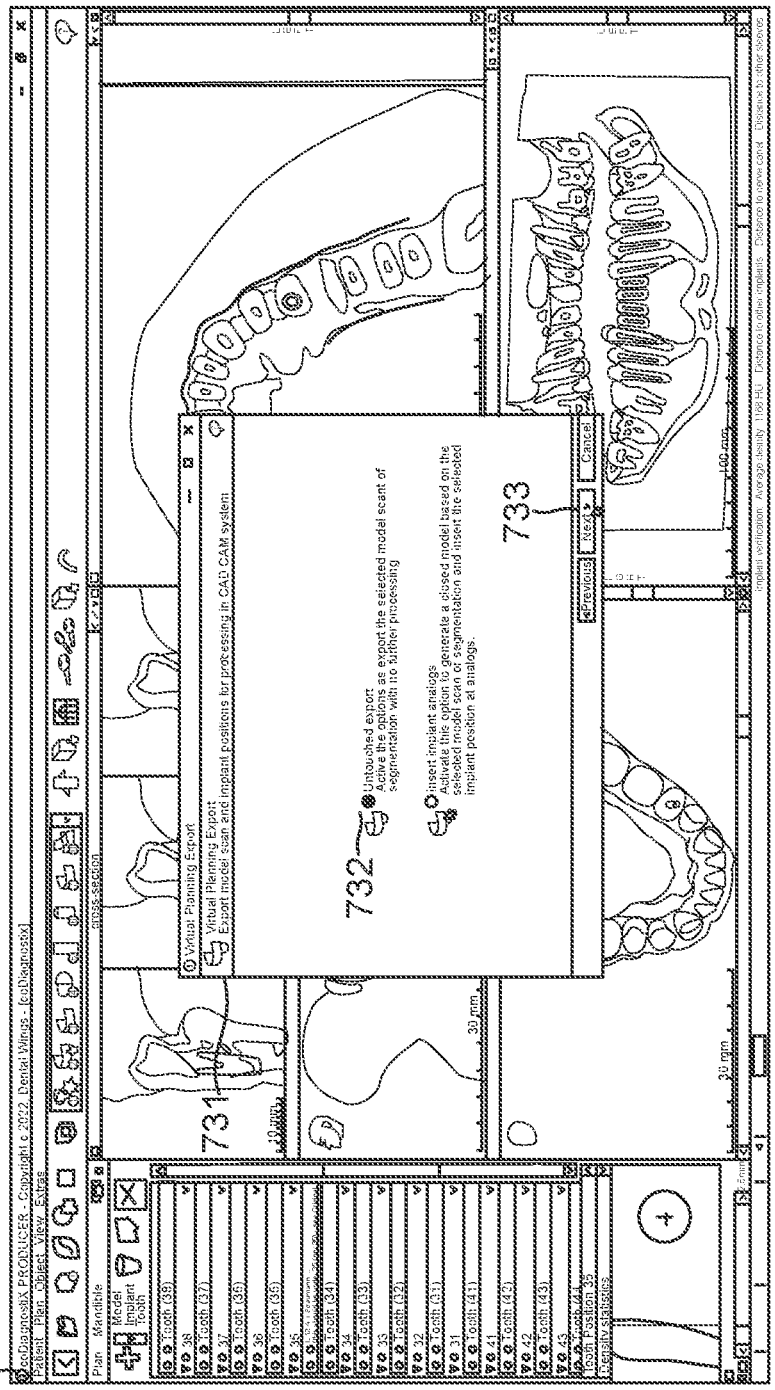
Figure 7G:
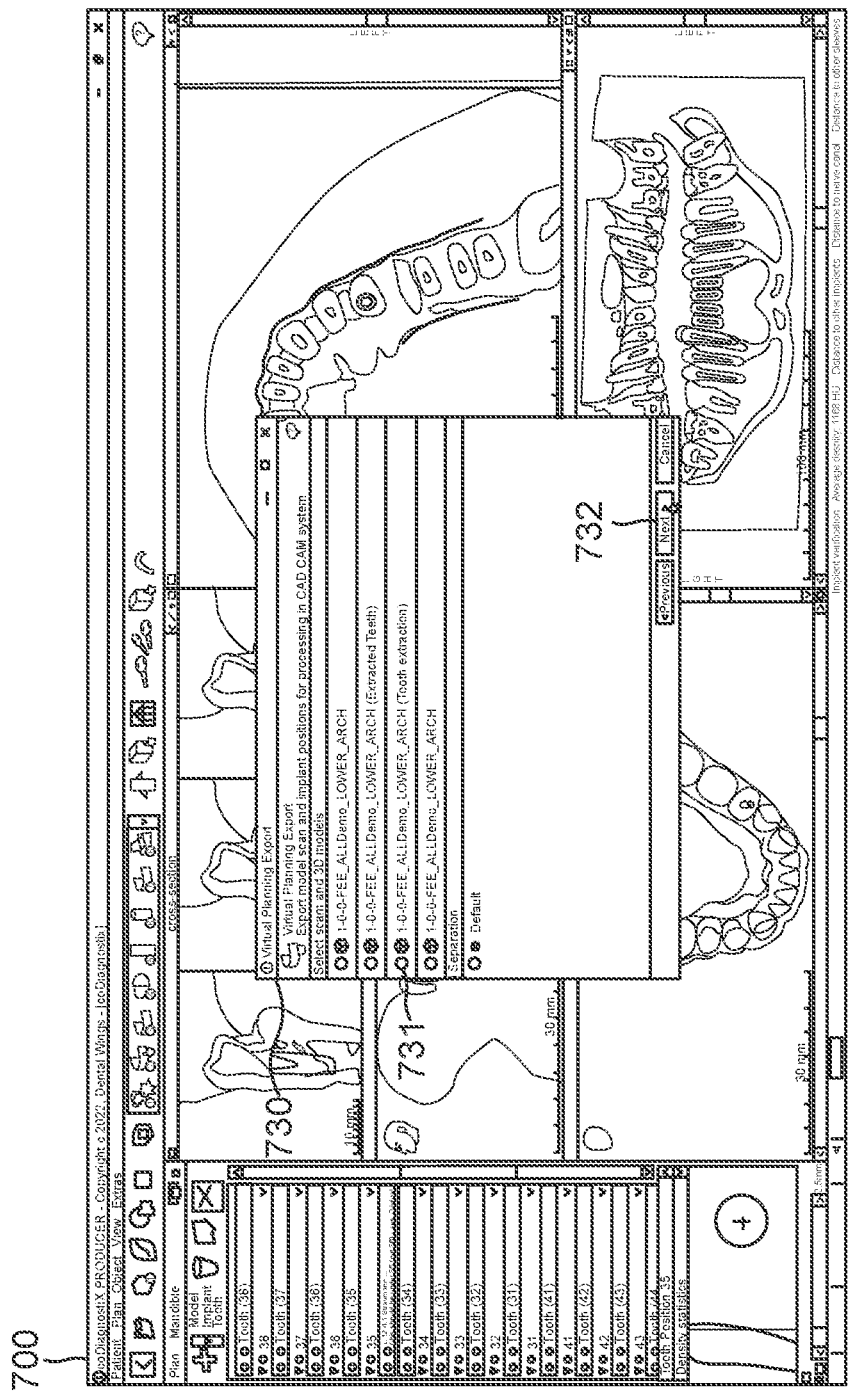
Figure 7H:
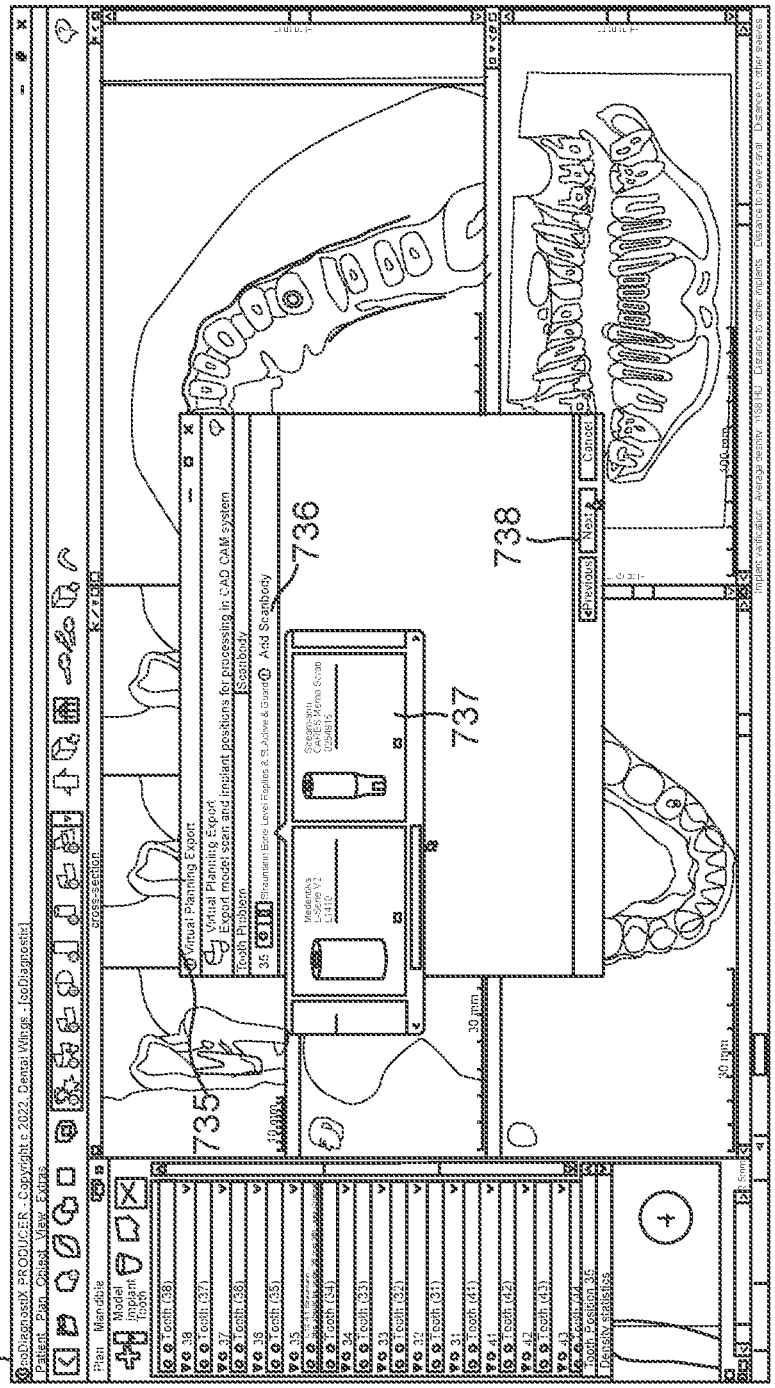
Figure 71:
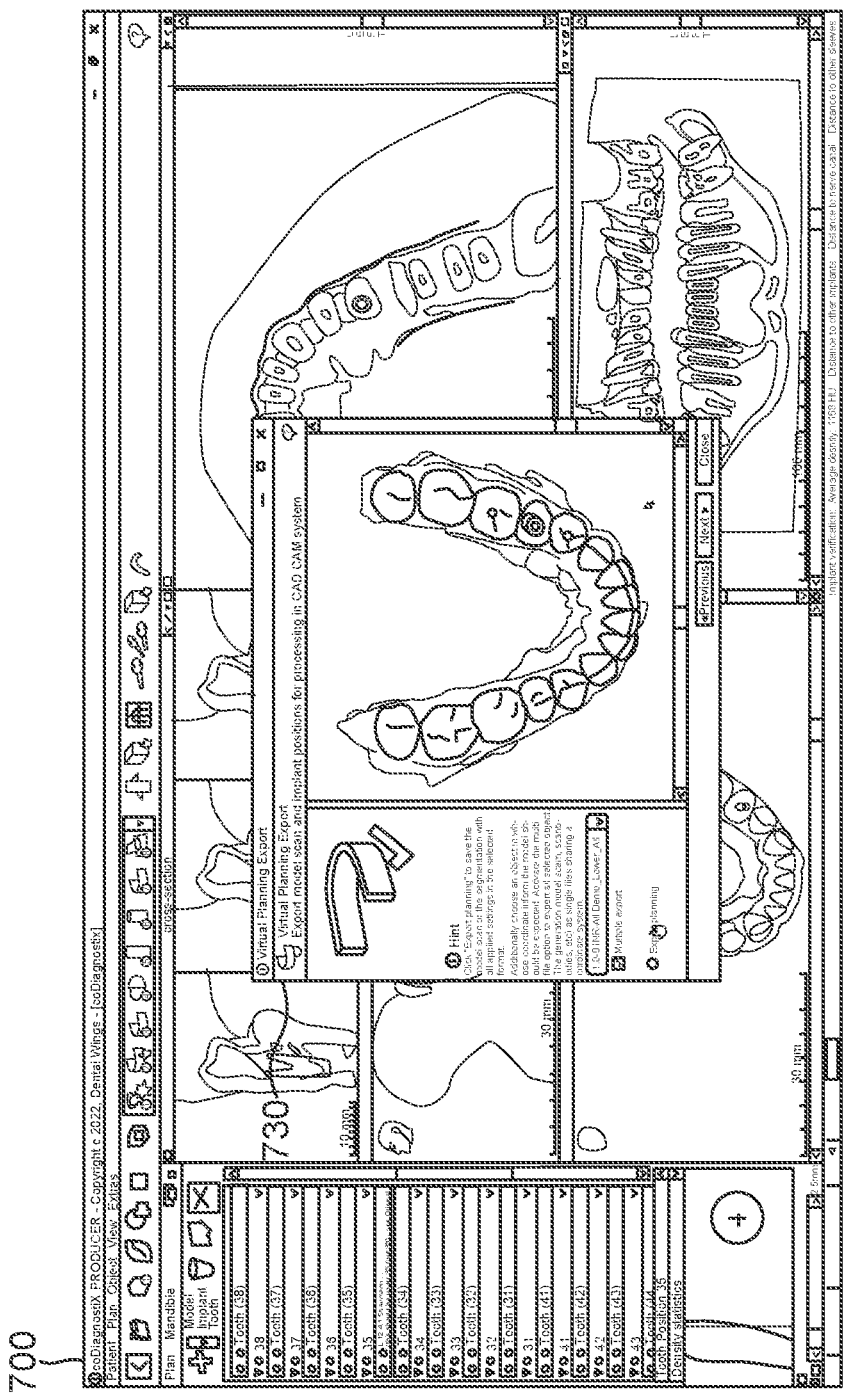

Once these files have been created, the user may click on the Plan menu 723 in the GUI display environment 700, as shown in FIG. 7D, and select a Virtual Planning Export control 724. In the next step, shown in FIG. 7E, the user can then select the format of the export file in a format selection control 727 of a popup window 726. In the example, the user selects an STL format option 728 and clicks on Next 729 to move to the next menu. In the next step shown in FIG. 7F, the user selects a button control 732 to activate an option to export the selected model scans or segmentations with no further processing. Clicking on the Next button 733, in FIG. 7G the tooth extraction file 731 is selected from the Export File selection popup window 730. Clicking on the Next button 732 brings up the implant selection popup window 735, shown in FIG. 7H, which offers a scan body selection control 736. The scan body selection control 736 includes a scan selection control 737 which displays and allows selection of a suitable scan body from a set of possible scan body types. The user can select a scan body from the menu of scan bodies to add the selected scan body to the model for export. The user then clicks the Next button 738. In FIG. 7I, the user can select additional options, such as selection of the 3D coordinate system the model should be exported to, and selection of whether the exported objects should be exported as individual files sharing a coordinate system. Clicking on the Export Planning line 741 invokes the export function based on the selected options and parameters as selected by the user in the previous screens. The export files are saved in a known location in computer readable memory.

Figure 7J:
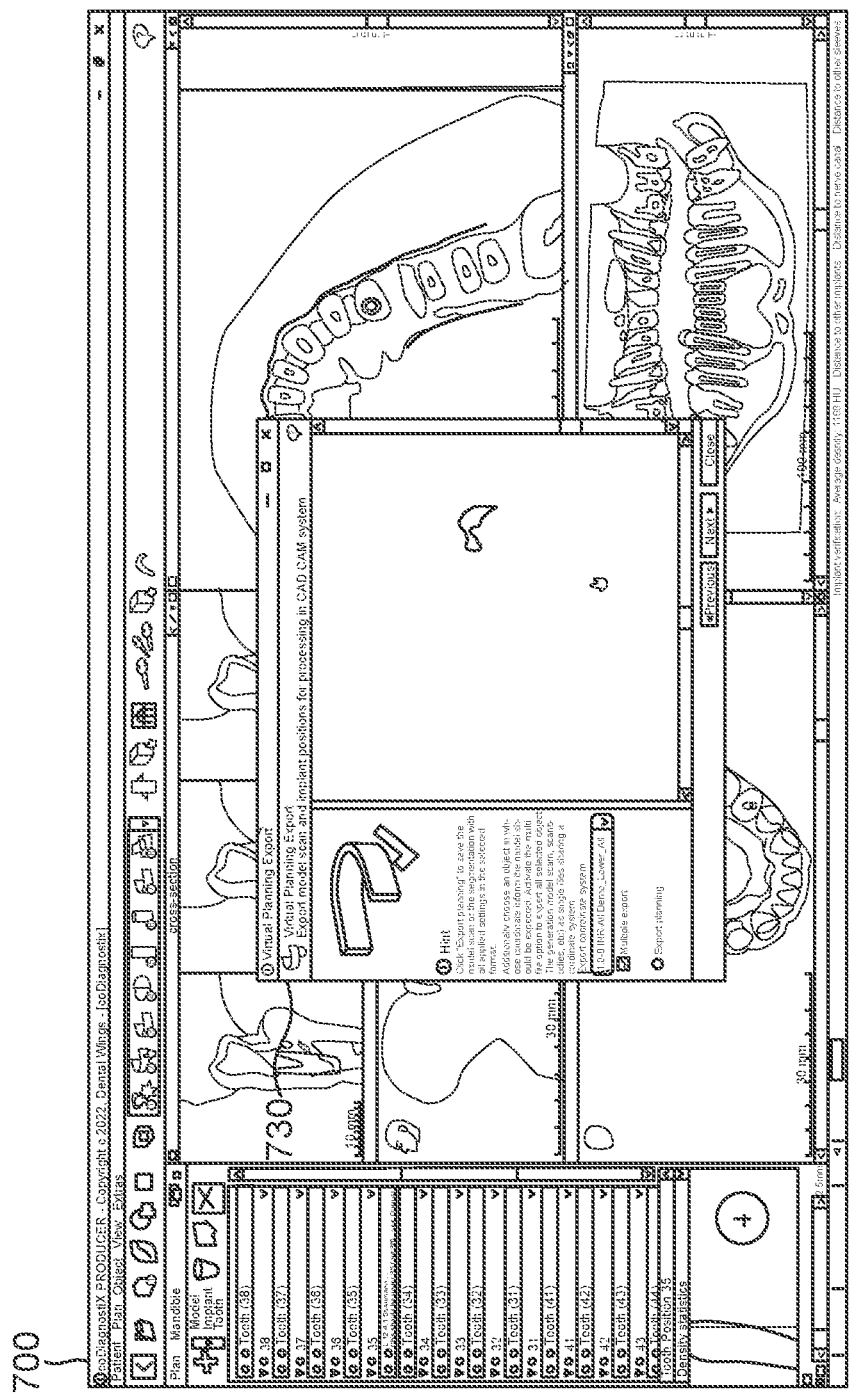

In FIG. 7J, the same process may be followed to export the surface scan crown segment of the virtually extracted tooth (and optionally the antagonist tooth crown segment that is, the crown segment from the tooth in the opposite jaw which meets the targeted extracted tooth in the occlusal plane when the jaws are closed). It is important to ensure that the surface scan teeth segments are exported in the same coordinate system as the exported virtual tooth extraction model.

The resulting exported files comprise a 3D model of the patient's dentition with a virtual tooth extraction of the tooth where the intended implant replacement is to be placed. In place of the extracted tooth is a virtual socket where the virtual tooth was once seated. Included in the model is the virtual implant post placed in the socket where the dental professional placed it during the implant planning process.

Figure 8:
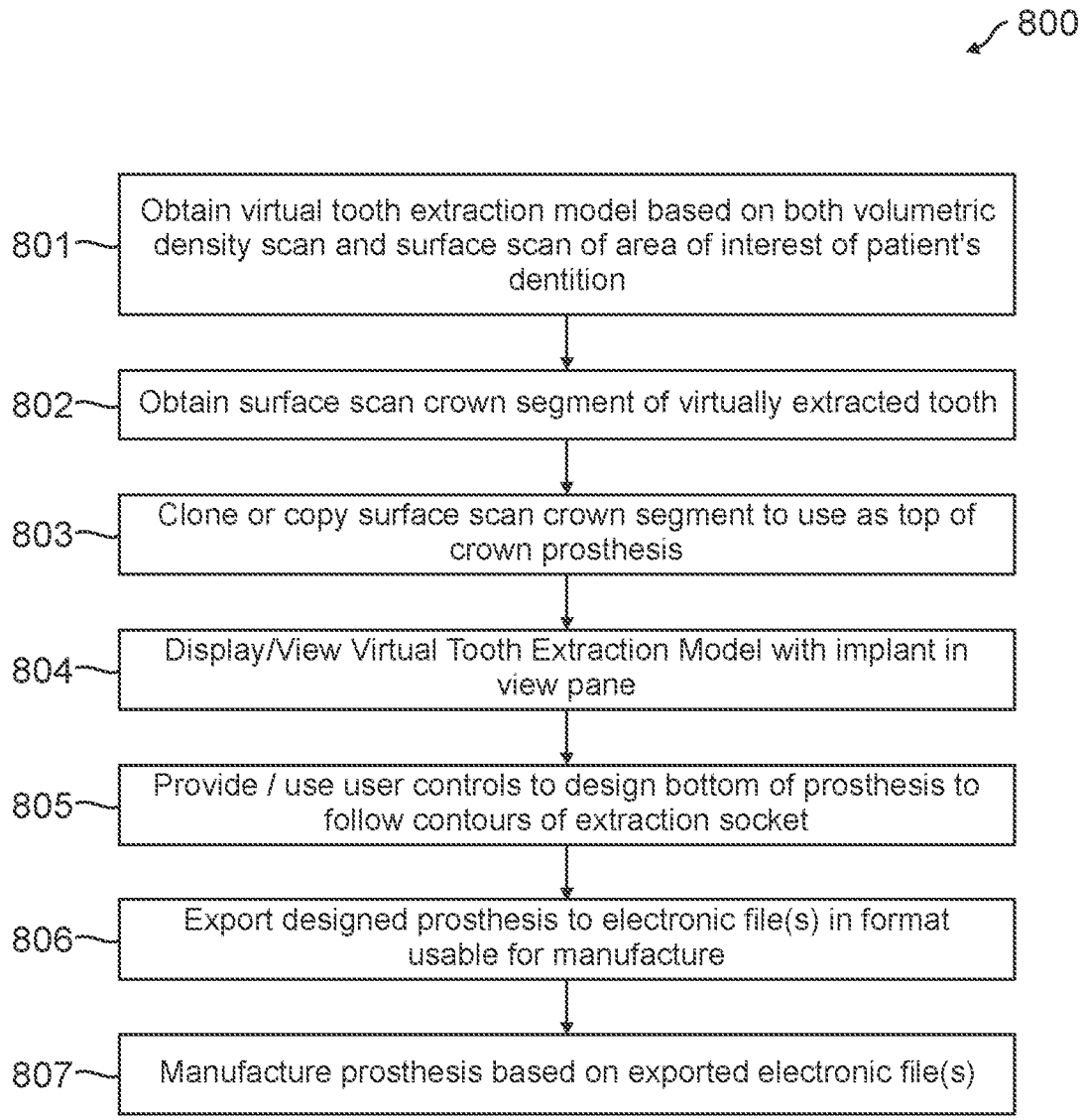
FIG. 8 represents a flow diagram outlining a fourth aspect of the method according to an embodiment of the present disclosure.

The next step in the implant planning process is the design of a prosthesis or tooth restoration, such as a temporary or permanent abutment, with a crown, a bridge or dentures. FIG. 8 is a flow illustrating an exemplary process for designing an anatomically correct prosthesis, which is especially useful for designing temporary abutments for placement in the patient's mouth while the tissue around the surgical site heals after implant placement.

According to aspects of this disclosure, design of temporary abutments based on a virtual tooth extraction as set forth above allows the design of a custom abutment (or other prosthesis) based on the patient's anatomy determined from the virtual tooth extraction. This means the temporary abutment (or other prosthesis) can be designed and manufactured even before the implant placement surgery so that it can be ready for placement immediately (or soon thereafter) upon placement of the implant post. Because the virtual tooth extraction generates an anatomically correct tooth socket specific to the patient's extracted tooth anatomy, there is no need to scan the patient's actual socket after the tooth is actually extracted in order to get the socket surface profile.

This saves significant time, since typically such a scan must be deferred until such time as some initial healing has taken place since bleeding at the surgical site can interfere with obtaining a highly accurate surface scan of the socket.

The process described in FIG. 8 includes obtaining a virtual tooth extraction model based on both a volumetric density scan and a surface scan of the area of interest of the patient's dentition (step 801) and obtaining a surface scan crown segment of the virtually extracted tooth (step 802). In an embodiment, the virtual tooth extraction model may be obtained according to the methods and systems described above. The obtained surface scan crown segment is imported into the model and used as the prosthesis crown (i.e., the portion of the prosthesis that will be visible above the gum line). In an embodiment, the design is electronically designed in a CAD/CAM tool that provides a clone function to clone a virtual wax up of the original tooth crown.

In a GUI of the prosthesis design tool, the virtual tooth extraction model with the virtual implant placed therein is displayed to allow a user to view the model (step 804). User controls are provided by the GUI to allow the user to design the bottom portion of the prosthesis such that for at least some portions, the design follows the contours of the inside of the extraction socket (step 805).

The final design is a prosthesis design having a top portion that substantially conforms to the surface scan crown segment and a bottom portion having an exterior surface that substantially conforms to the inner surface of the tooth extraction socket from the Virtual Tooth Extraction model. The prosthesis design may be exported to one or more electronic file(s) in a format usable for subsequent manufacturing (step 806). A physical prosthesis may then be manufactured (step 807) based on the electronic file(s). In an embodiment, the electronic files comprise, or are converted to, 3D printing instructions for printing by a 3D printer. In another embodiment, the electronic file(s) comprise an STL file.

Figure 9A:
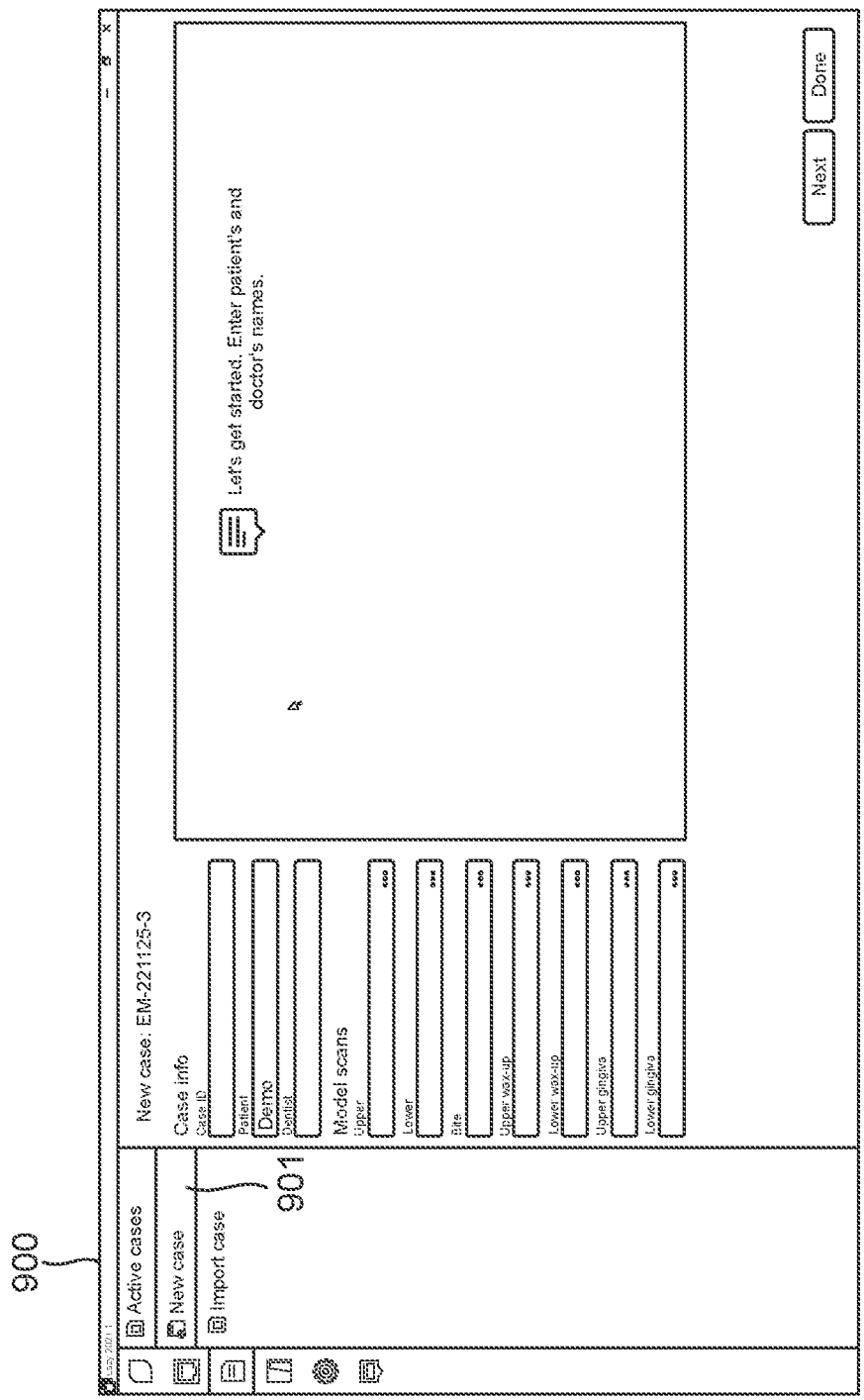
FIGS. 9A-9T depict a second exemplary graphical user interface implementation of various aspects of the present disclosure.
Figure 9B:
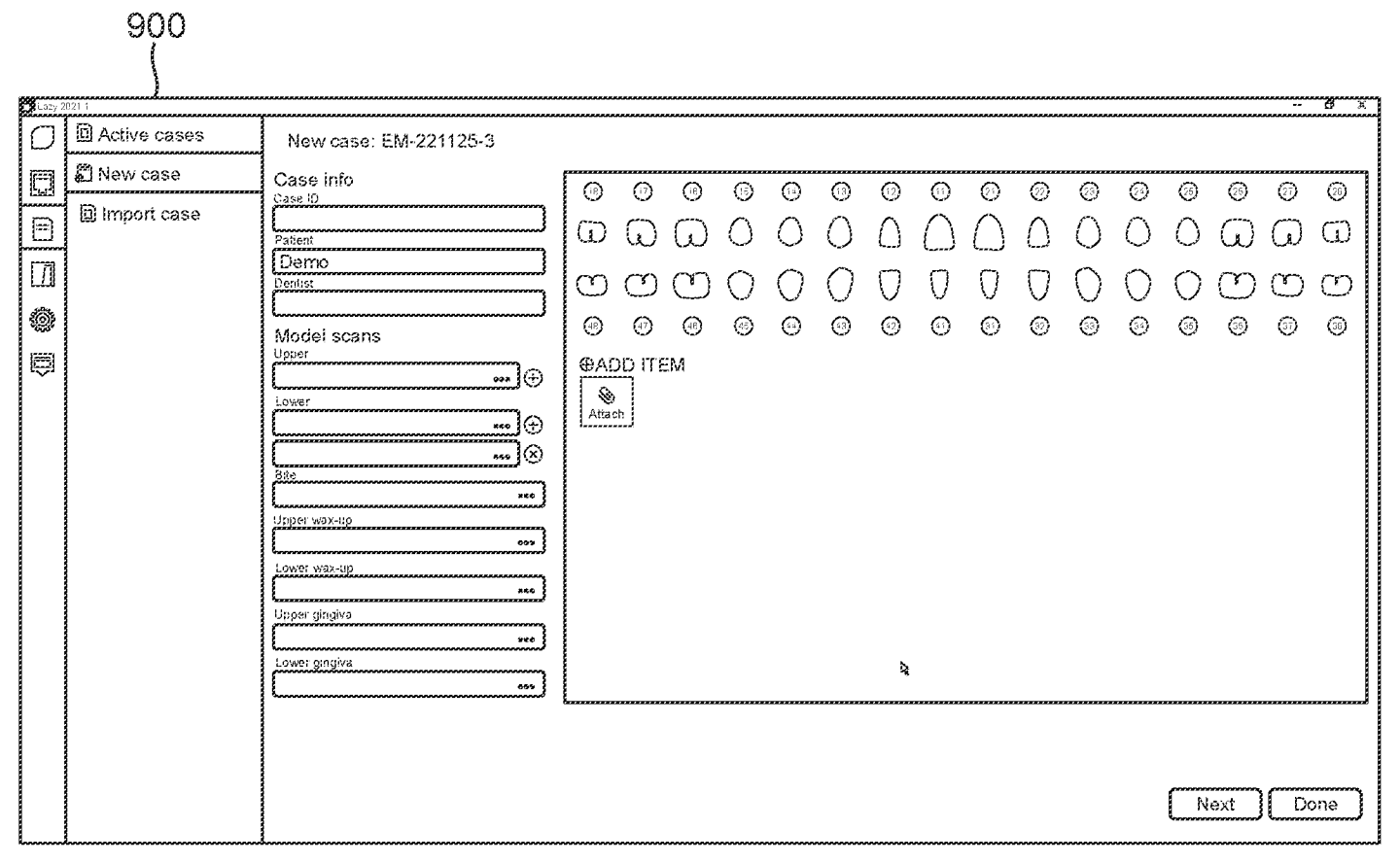
Figure 9C:
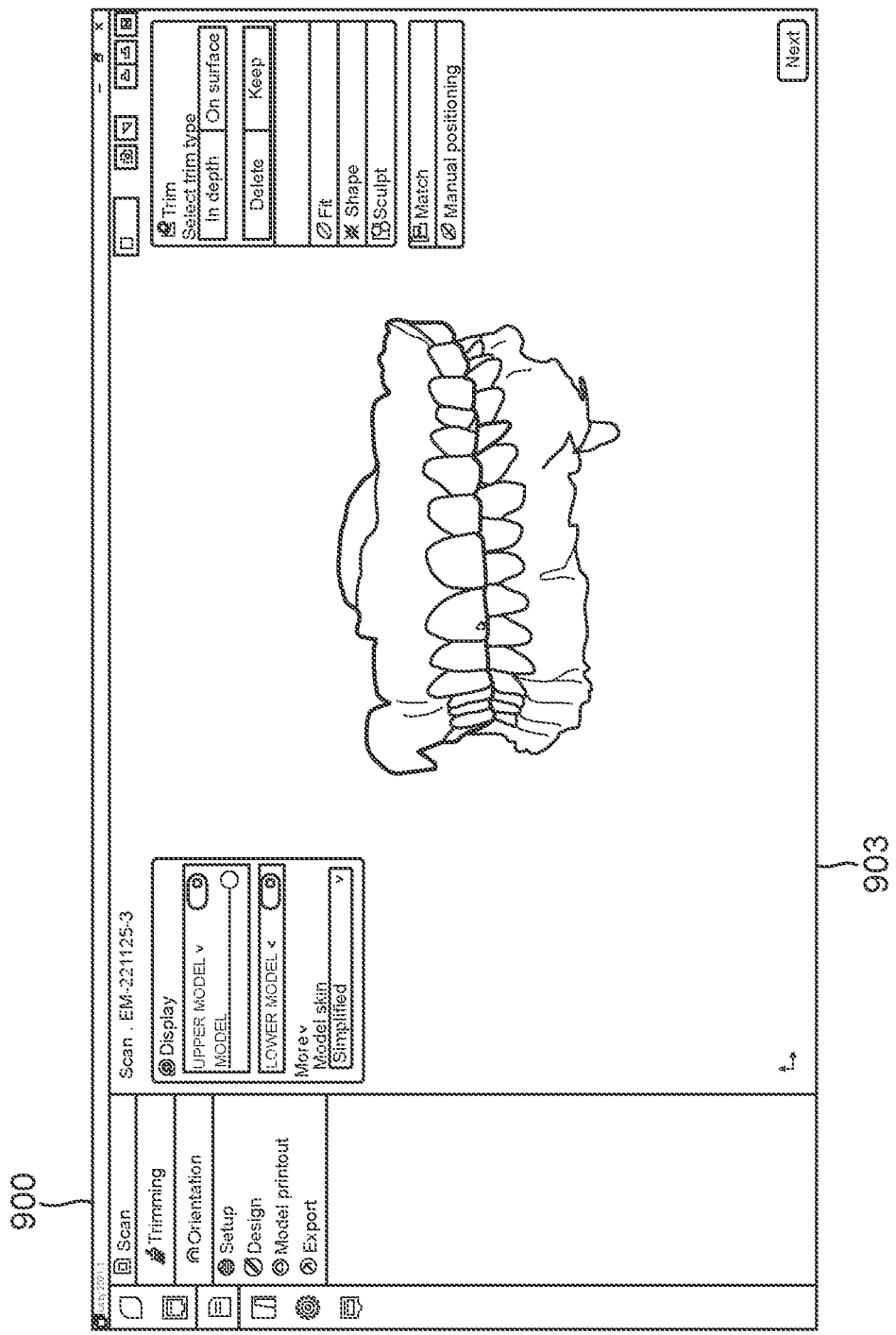
Figure 9D:
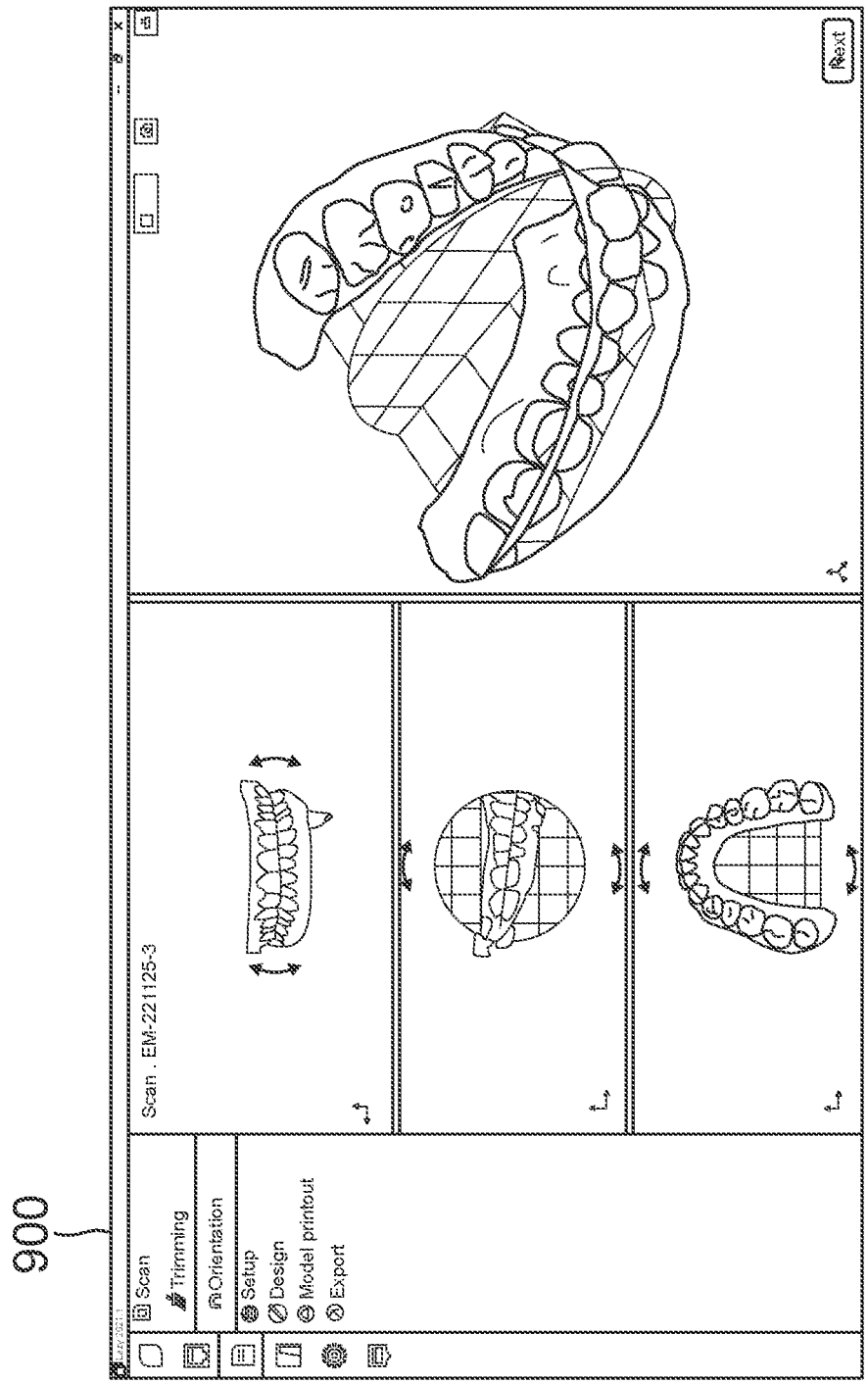
Figure 9E:
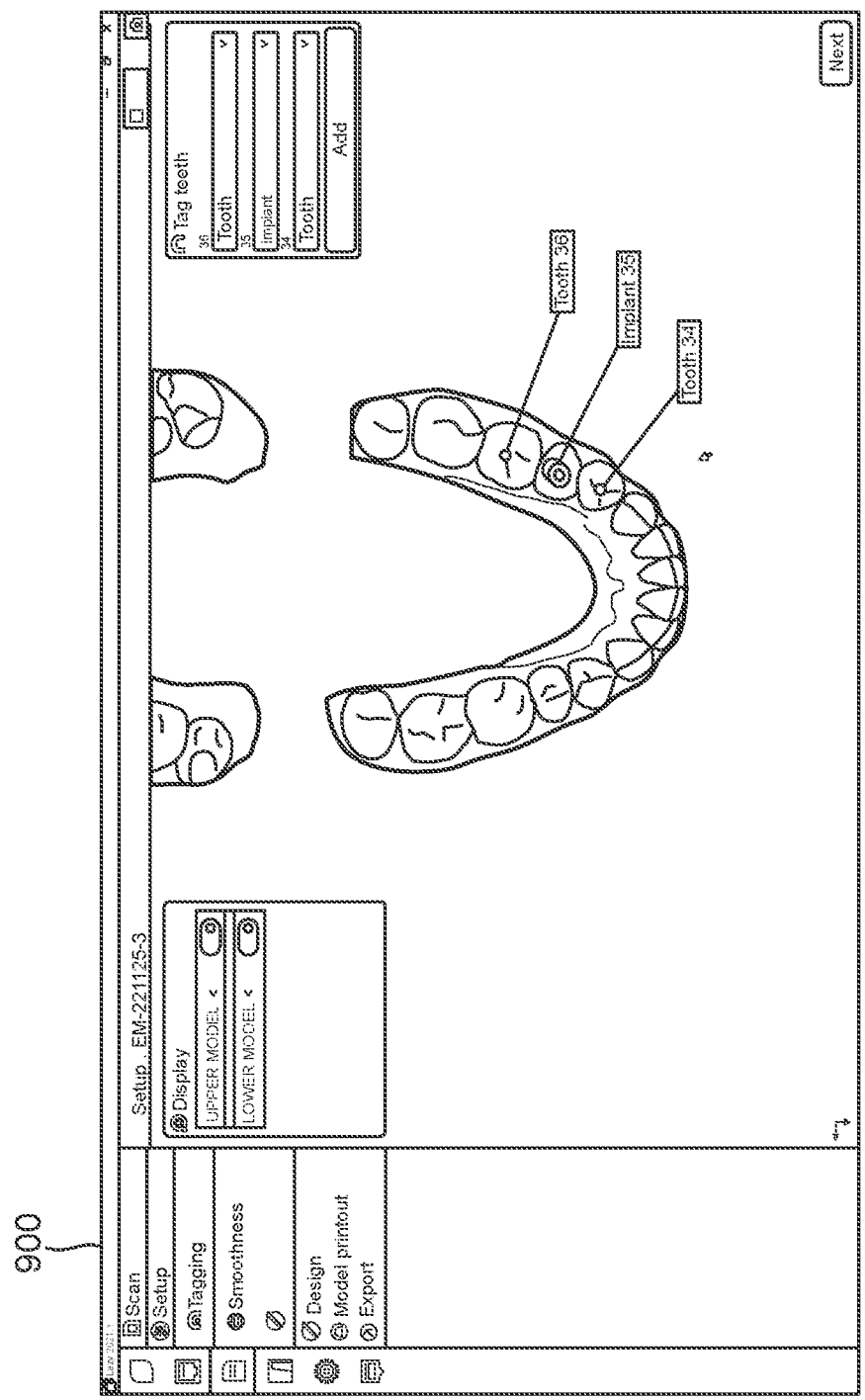
Figure 9F:
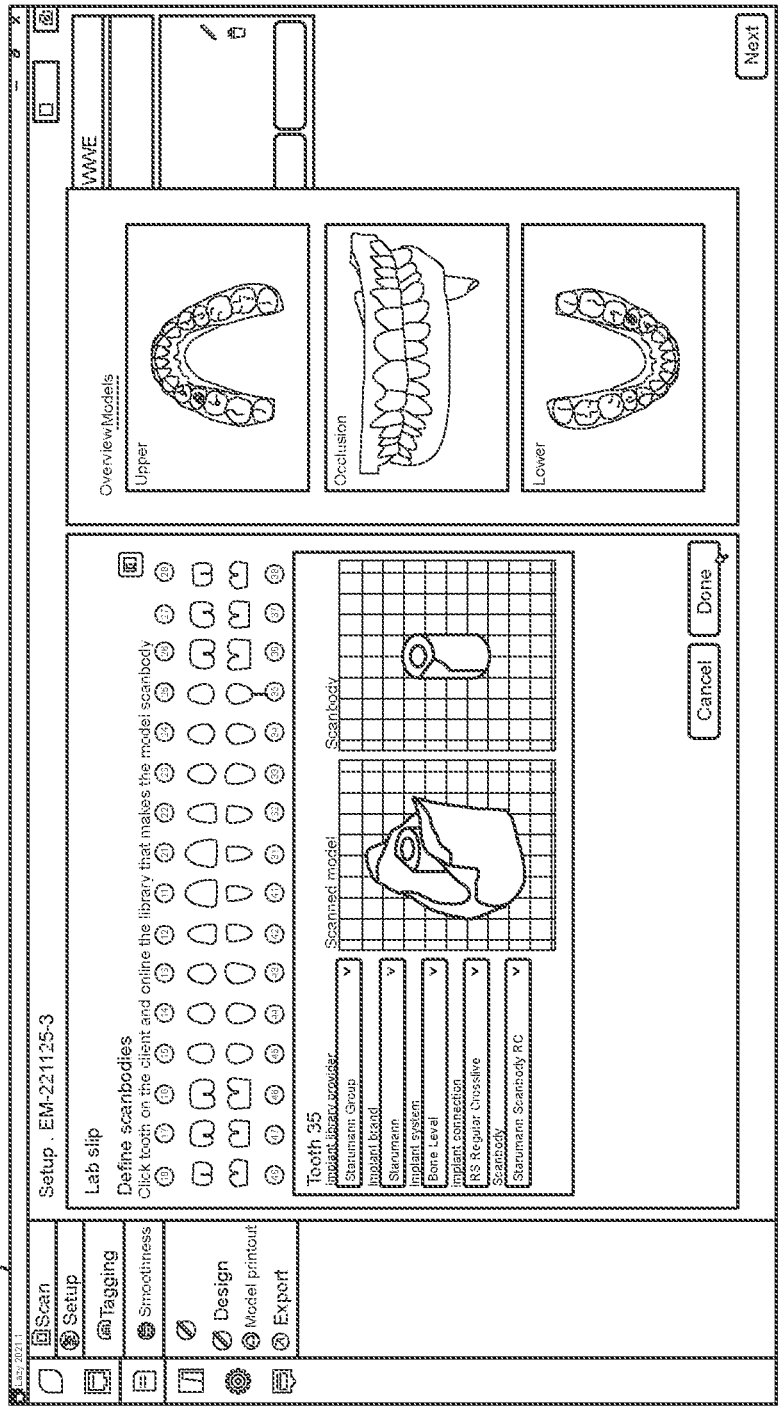
Figure 9G:
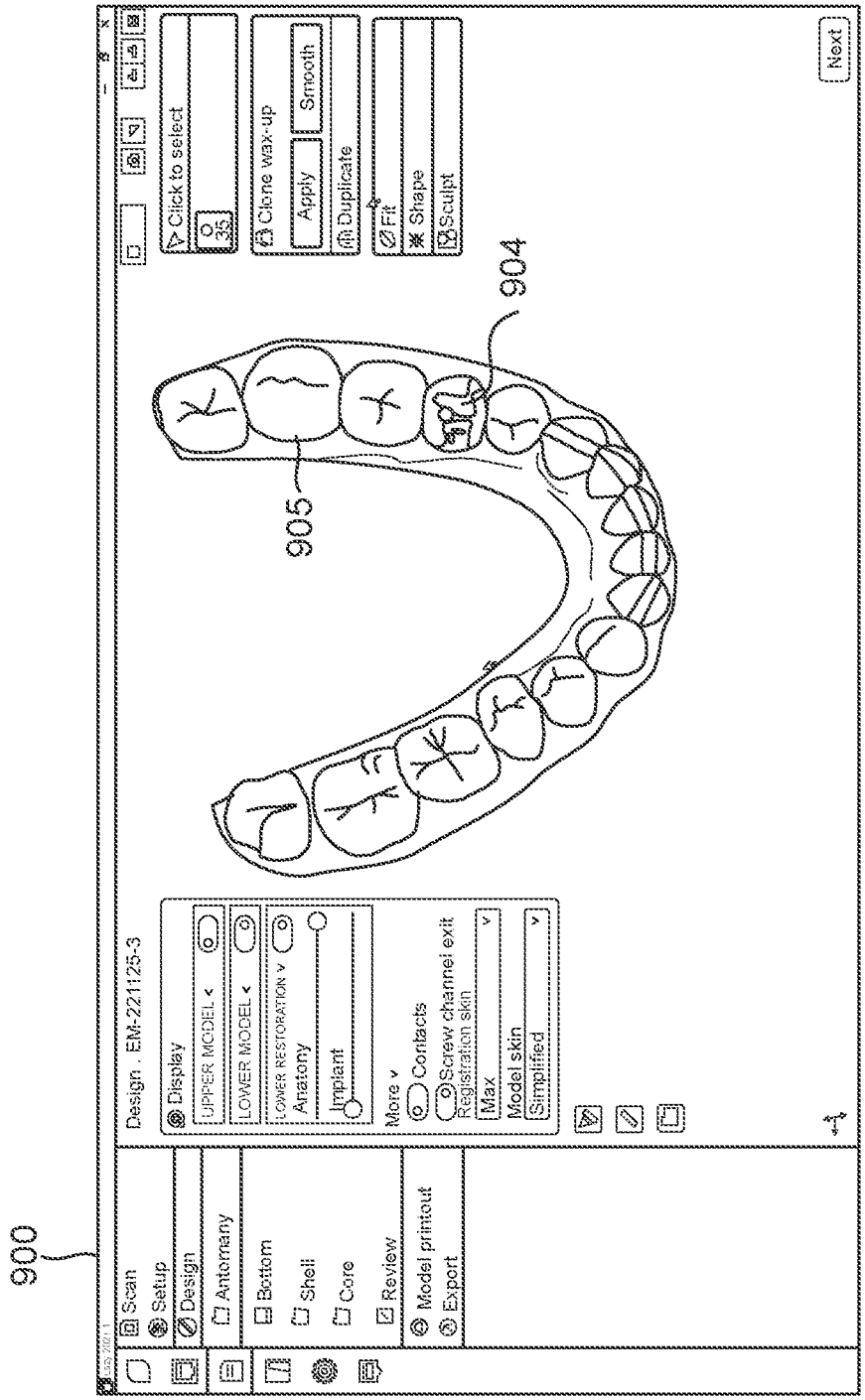
Figure 9H:
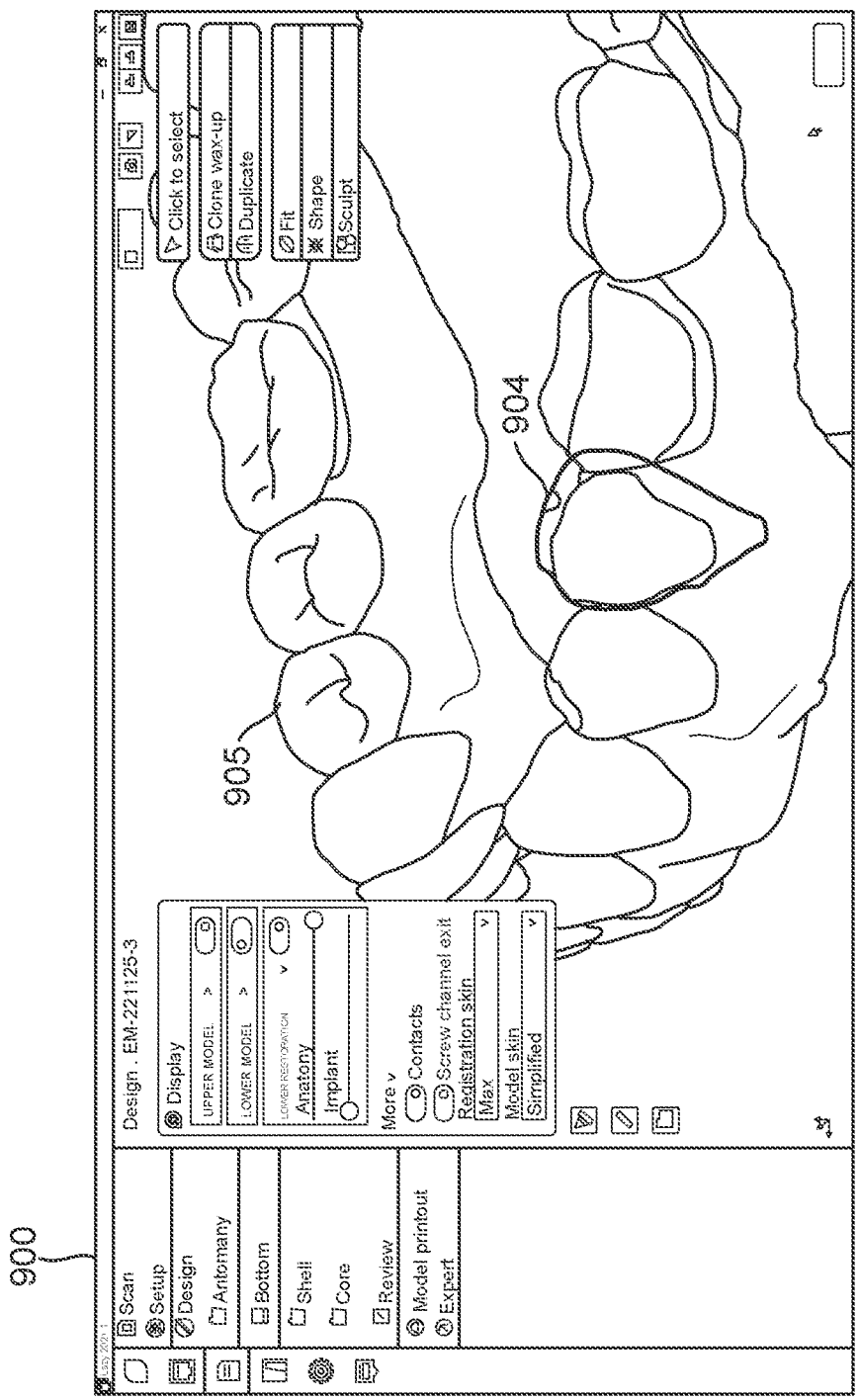
Figure 9I:
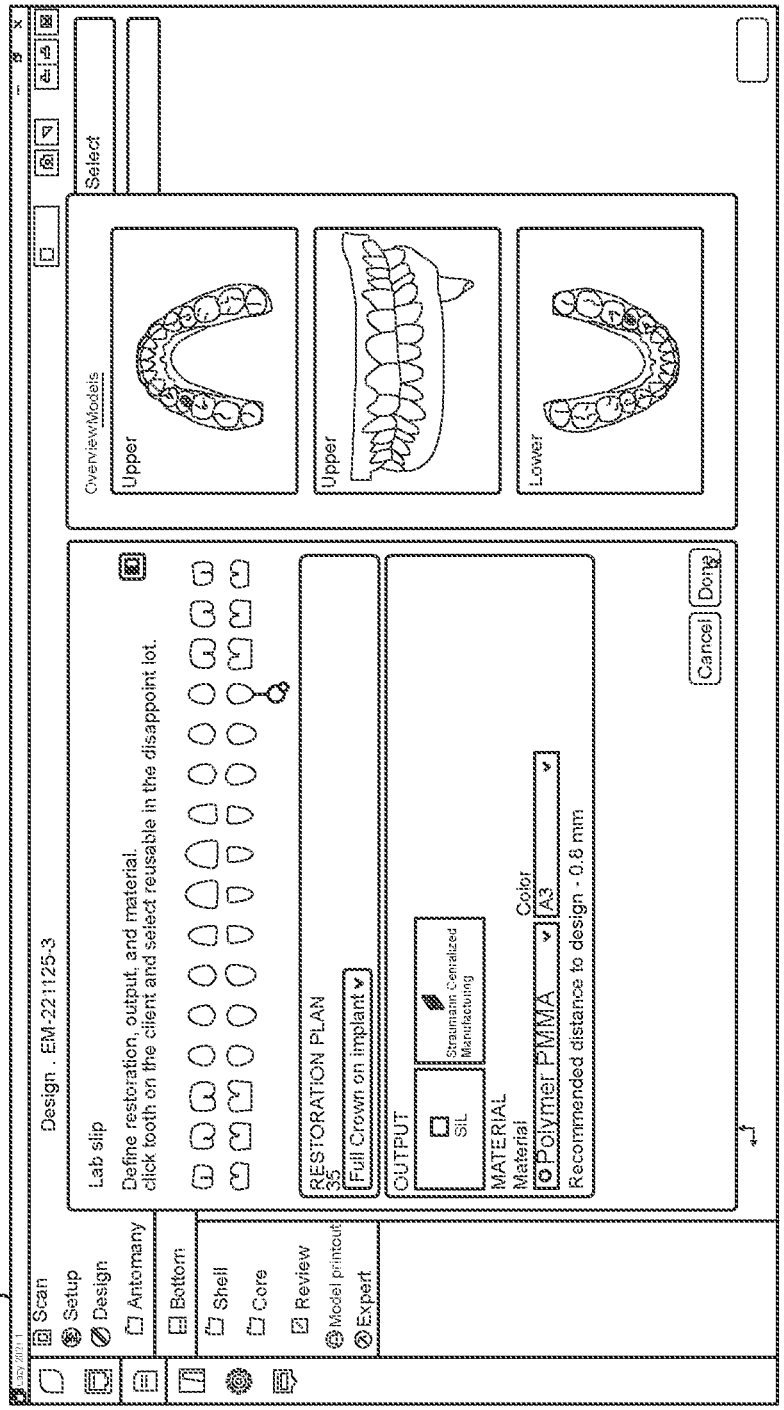
Figure 9J:
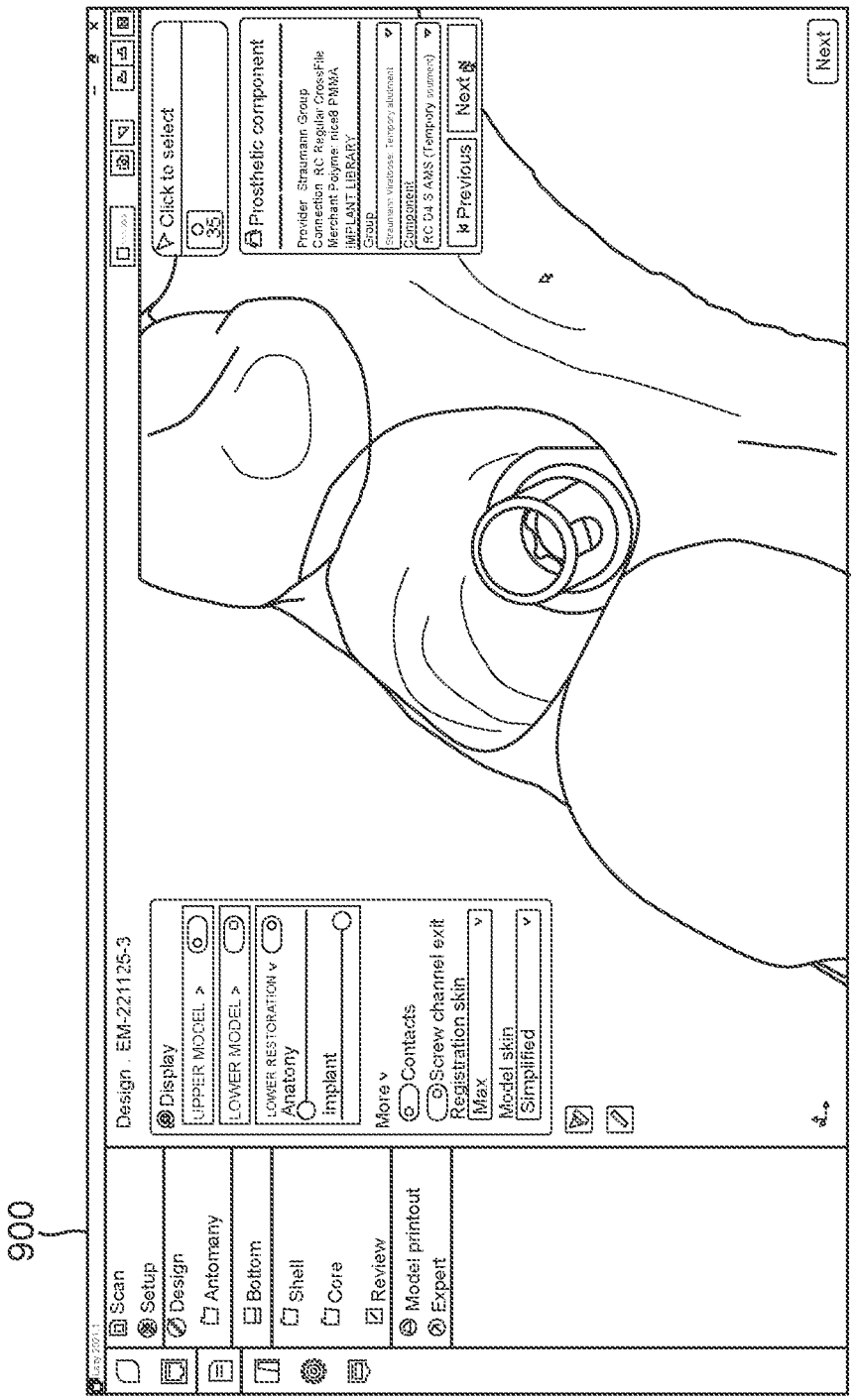
Figure 9K:
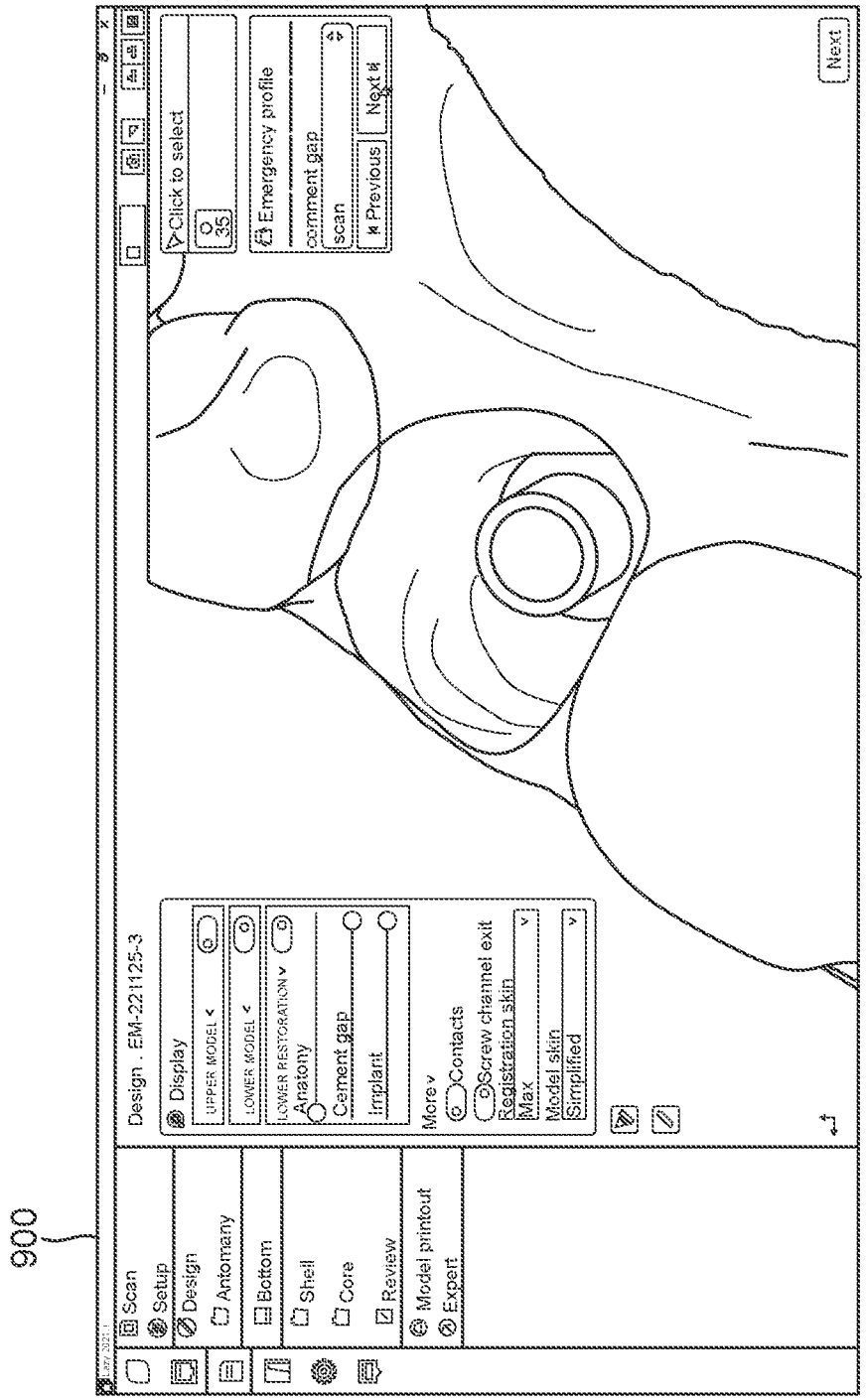
Figure 9L:
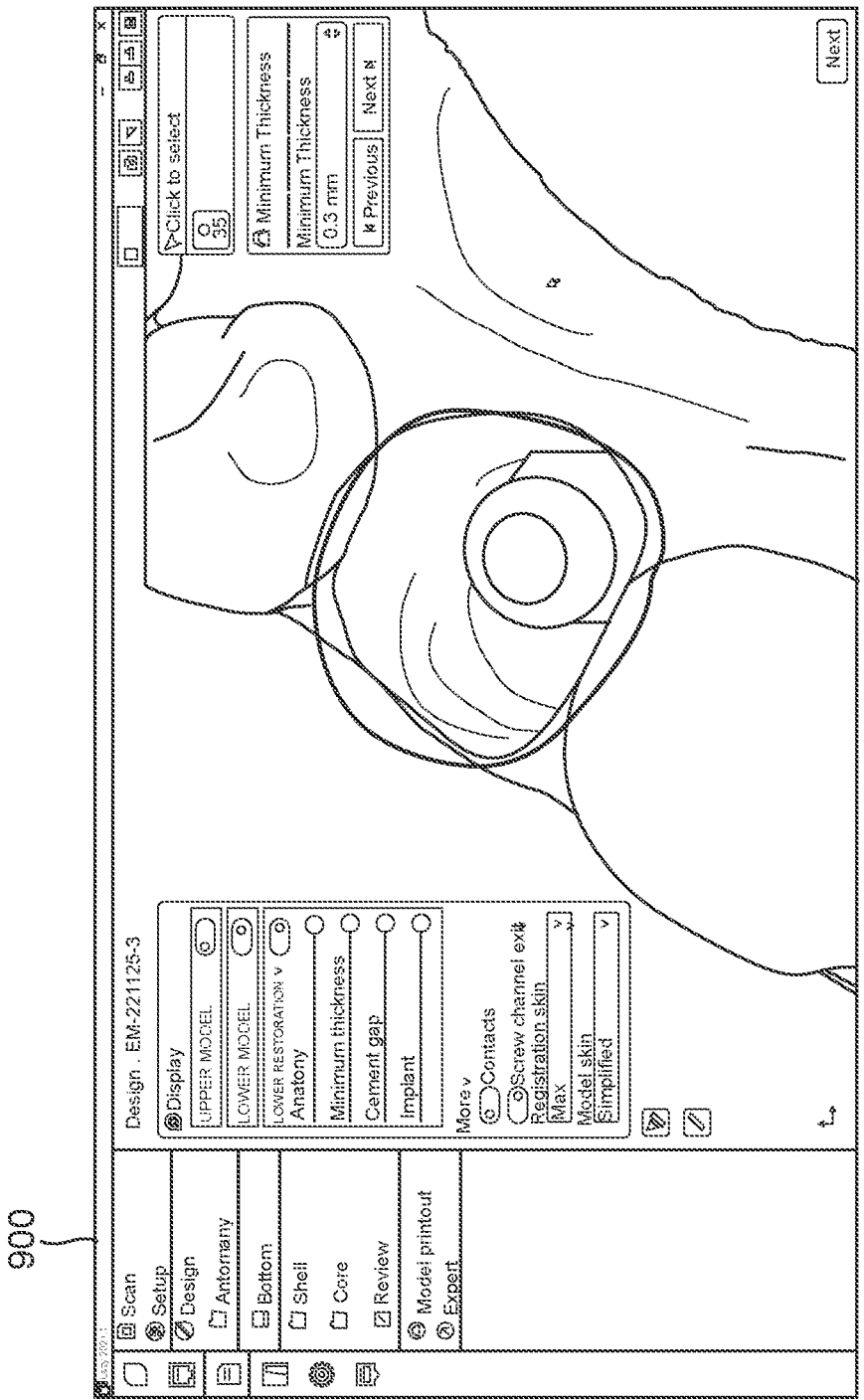
Figure 9M:
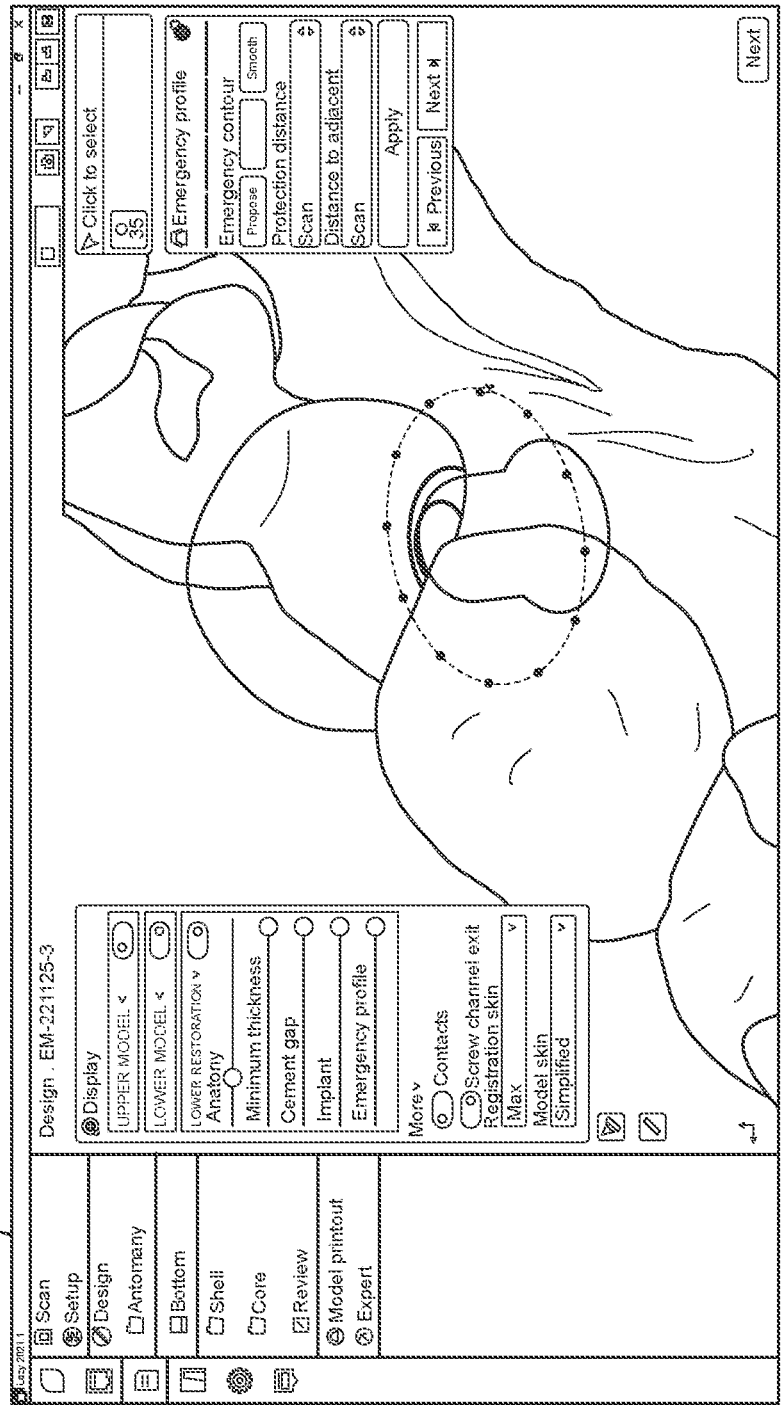
Figure 9N:
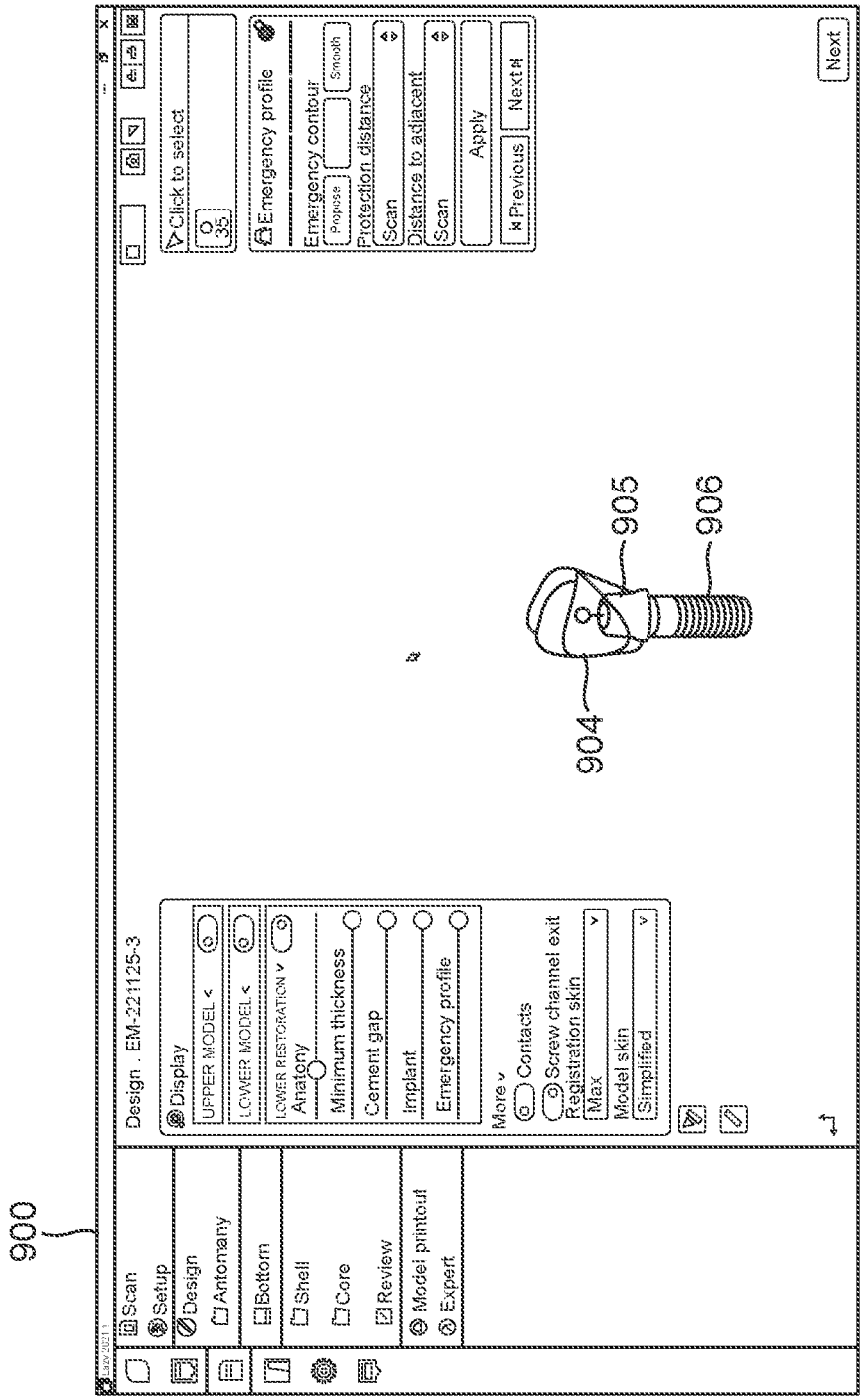
Figure 90:
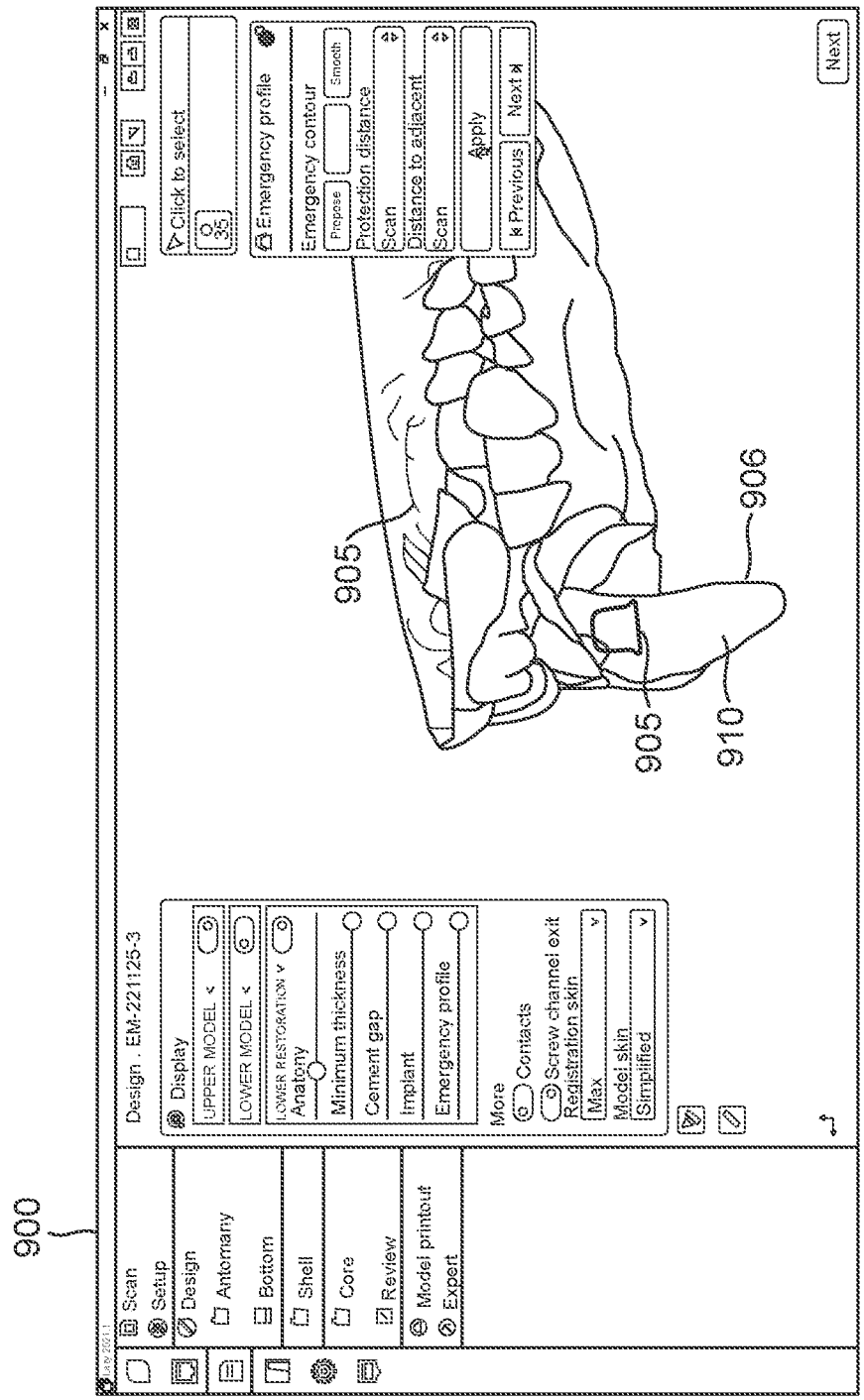
Figure 9P:
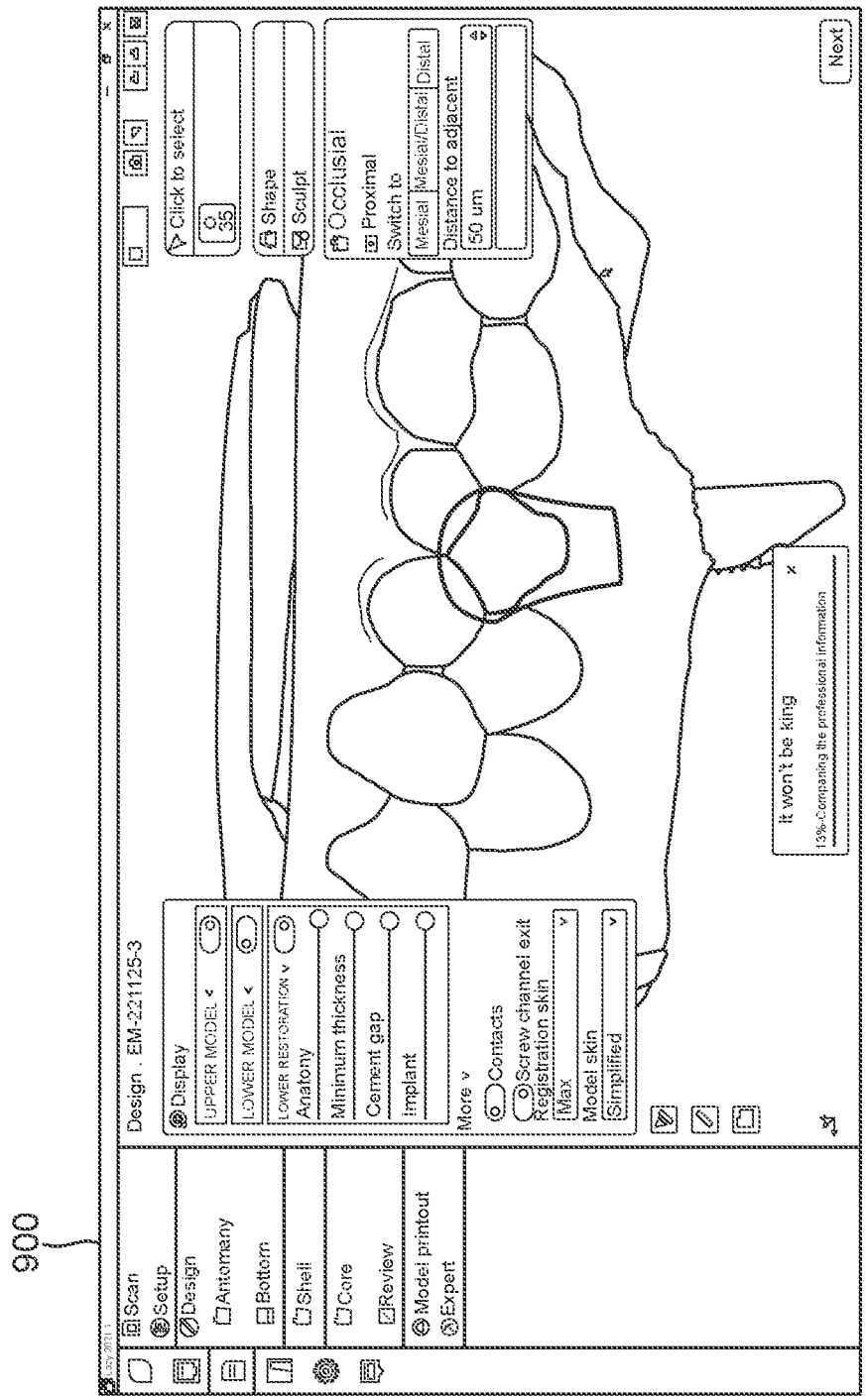
Figure 9Q:
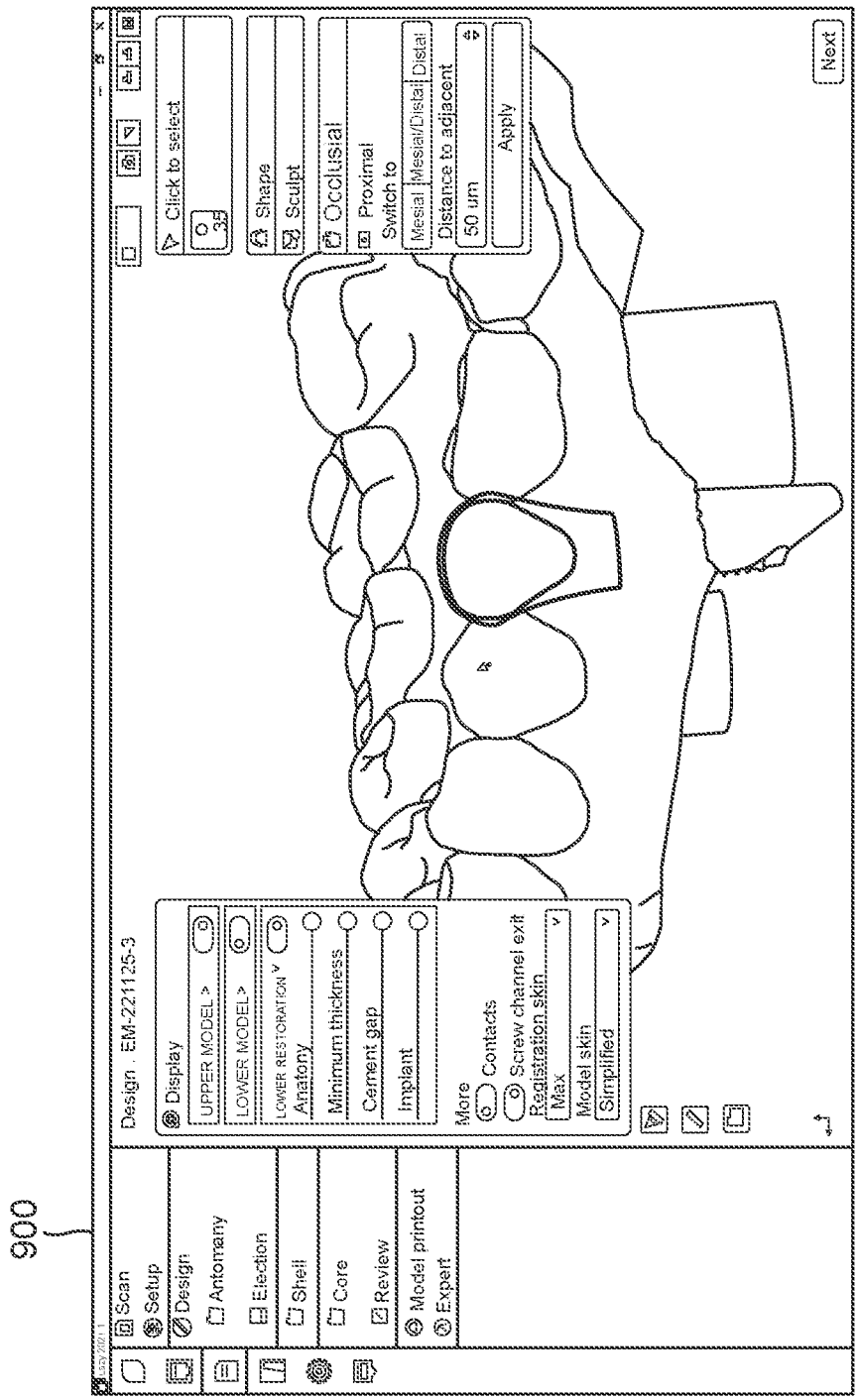
Figure 9R:
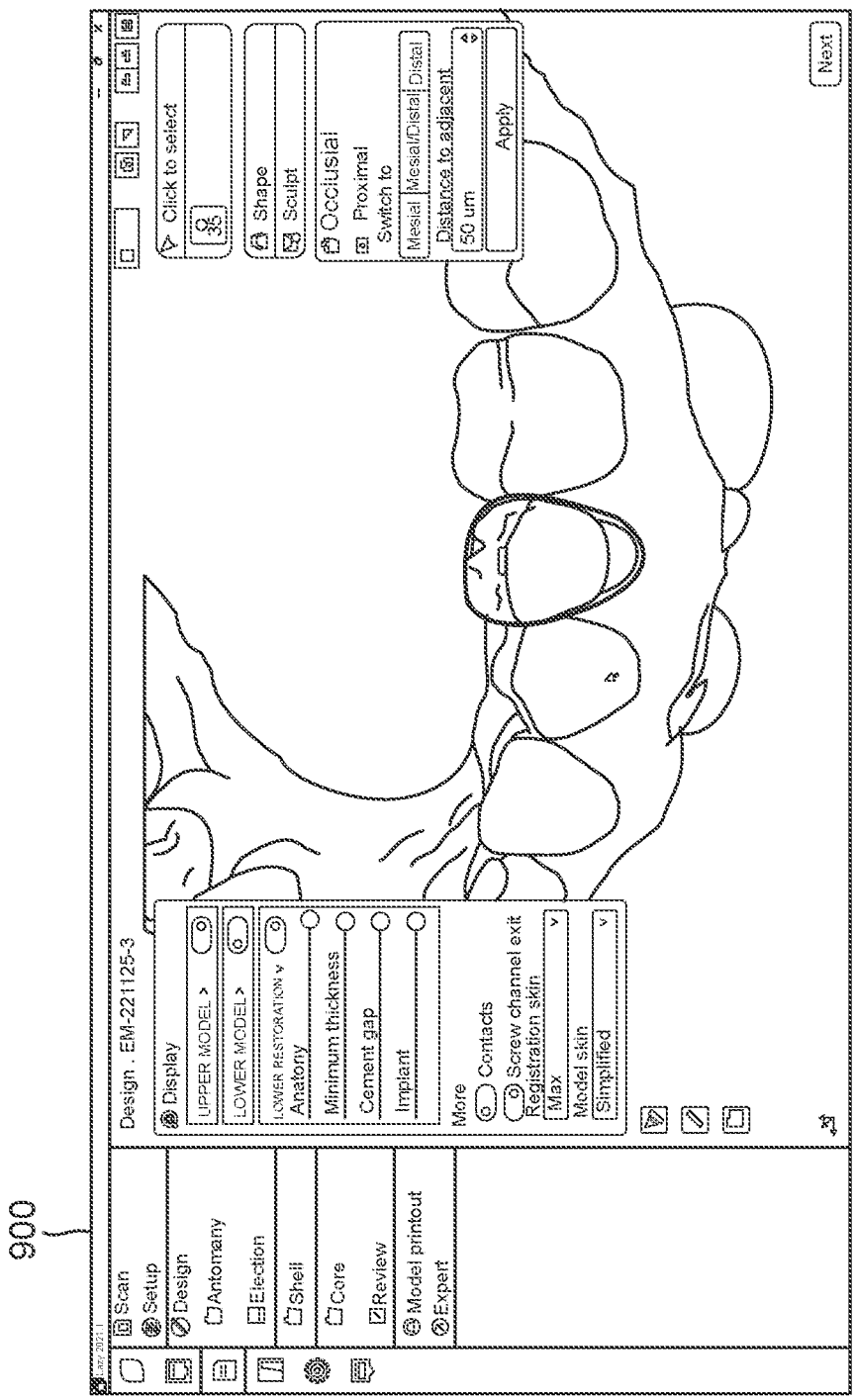

FIGS. 9A-9R depict a GUI display environment 900 for a prosthetic design application, such as a computer-aided design (CAD) or computer-aided manufacturing CAM tool. In an embodiment, the prosthetic design tool is an application 215*d* that operates in a system such as 200 previously described in FIG. 2.

FIG. 9A is a GUI display environment 900 displayed on an electronic display 209 and having user input controls and display areas as discussed hereinafter. To design a prosthetic, a user begins a new case by clicking on control 901 (FIG. 9A), inputting case information (for example into text boxes Case ID, patient ID, and Dentist ID to be associated with the new case), and selecting and loading 3D models generated from patient scan data into memory for use by the application 215*b*. In the example, a tooth crown is to be designed. The user inputs the file names for the virtual tooth extraction files (in this case as the lower teeth model input) and the extracted tooth file (as the Lower wax-up) and loads the files into the system (for example by clicking on the Save button (FIG. 9B). The application displays the 3D model from the selected Virtual Tooth Extraction file(s) in a view pane 903 (FIG. 9C). If needed, the application provides controls in environment 900 for cleaning the scan (for example, to fill in holes where the scan data is incomplete, smooth scan lines, remove noise, etc.). Following, the application may provide tools to adjust the orientation of the model(s) to the occlusion plane if necessary (FIG. 9D).

Prior to proceeding with the design, the user tags the teeth positions in the displayed model to indicate to the application 215 the position(s) of the tooth or teeth for which a prosthetic is to be designed, and which teeth are adjacent to tooth/teeth for which the prosthetic is to be designed (see FIG. 9E). Next, in FIG. 9F, the user selects the platform (implant manufacturer, implant type and connection), and scan body. These selections should match the implant and scan bodies selected in the dental implant planning application and which the virtual tooth extraction files were generated based on.

Once the setup is complete, the user can proceed to designing the prosthetic. In FIG. 6J, the surface scan crown segment from the 3D model was exported as an individual segment in a matching 3D coordinate system as the virtual tooth extraction model. Because the surface scan crown model was generated from an optical scan of the patient's original tooth (before actual extraction of the real tooth), the surface scan crown segment may be used as a digital wax-up model without having to again scan the patient's mouth. Since surface scan crown segment was exported as an individual segment matched to the same 3D coordinate system as the virtual tooth extraction model, the surface scan crown segment of the virtually extracted tooth can be mounted into the view pane with the virtual tooth extraction model and can be used directly by the application 215*d* as the upper portion of the prosthetic crown. By importing the surface scan crown segment file as the wax-up file (FIG. 9B), the designer can select a Clone wax-up control (FIG. 9G) to instruct the prosthetic design application 215*d* to clone the wax-up model in the wax-up model file to serve as the prosthetic crown surface. Once the Clone Wax-Up tool clones the wax-up model as the prosthetic, the user can then perform fine adjustment tuning of the prosthetic shape, via fitting, shaping and sculpting controls available in the GUI display environment 900. The environment 900 also includes controls to rotate and change the view of the model displayed in the view pane 903*a* so that the user can view the prosthetic 904 from all angles. For example, in FIG. 9H, the model 905 is rotated so that the prosthetic 904 can be viewed from the buccal side. This allows the designer to make adjustments to the prosthetic by viewing the prosthetic in situ within the virtual tooth extraction model 905.

Once the visible surfaces of the crown are designed based on the extracted surface scan crown segment obtained during the tooth extraction process, the user may then design the bottom of the prosthetic. The application may provide controls for the designer to input restoration specifications (see FIG. 9I), such as material type, color, as well as whether what should be output (e.g., output an STL file, output an order placement (which can be a direct communication to a remote manufacturing facility).

Figure 9S:
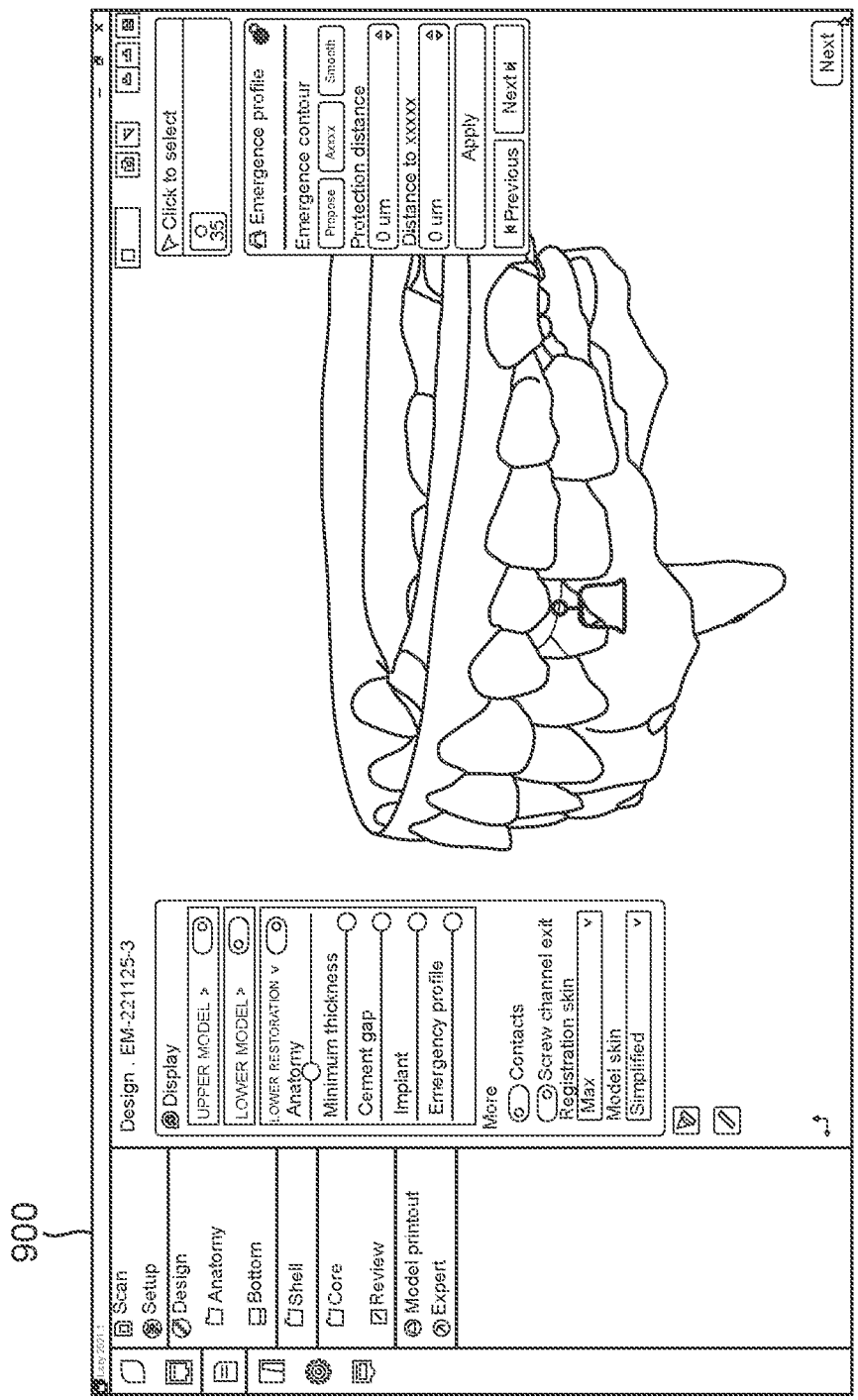
Figure 9T:
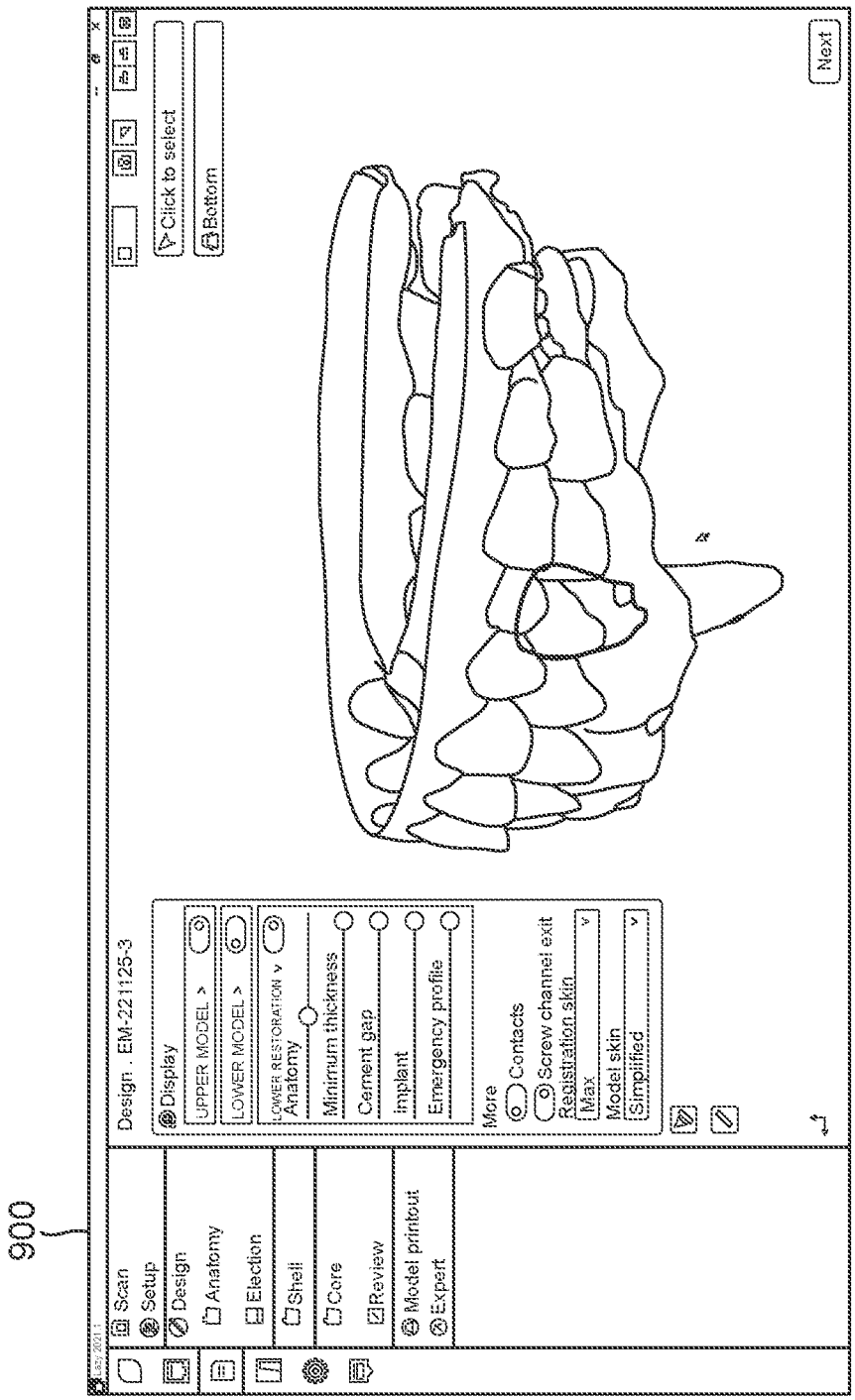

In FIG. 9J, the virtual tooth extraction model 905 is displayed in the view pane 903*a*. Since the example case in FIGS. 9A through 9T is a new case for design of a prosthetic design for an implant, and the virtual tooth extraction model 905 was exported with the implant placed in the model (for example using the process described in connection with FIGS. 7A through 7J), the virtual tooth extraction model 905 includes a virtual implant post. In this example, a temporary abutment is selected and automatically virtually connected to the implant post and displayed as shown. The user can then select the thickness of the cement gap (FIG. 9K), set the thickness of the material (FIG. 9L), and display the prosthetic 904 within the model 905, which includes the socket contours (or "emergence profile") (FIG. 9M). The user can also then turn off display of the model 905 to display only the prosthetic (FIG. 9N).

FIG. 9O shows the model 905 turned back on for display (see the on/off buttons for display of various models in FIG. 9O), and rotated to get a good side external view of the socket 910. With the anatomy transparency level set low (in order to view the implant post and abutment inside of the socket 910, it becomes clear that one can design an anatomically correct prosthetic 904 that conforms to the patient's oral anatomy by using the socket contours to guide the design of the lower crown portion of the prosthetic to fit against the contours of the inside of the socket 910. In this regard, the prosthetic design application provides controls to adjust the shape and fit of the lower portion of the crown.

Once the bottom of the crown prosthetic is shaped to conform to the contours of the socket 910, the designer can move on to specifying the shell of the prosthetic. The application may automatically calculate the proximal distance information between the prosthetic surfaces and the teeth on either side of the prosthetic (when it is virtually attached to the virtual implant post 906) (FIG. 9P) and generate a shell surface (viewed from the buccal side in FIG. 9Q and looking down at the occlusal plane in FIG. 9R). FIG.

9S shows the final prosthetic design within the model with both the upper and lower jaws with the anatomy model partially set to transparent in order to partially see the implant post 906, abutment, and prosthetic crown. The user can easily check the placement and shape of the prosthetic through visual inspection of the model. FIG. 9S. FIG. 9T shows the same model and orientation as in FIG. 9S, but with the anatomy at full opacity. The workflow will continue though the usual steps before sending the crown to production.

Upon completion of the prosthetic design, the design files may be exported and used to manufacture the design. In an embodiment, the exported design files may be sent to a manufacturing facility or a remote manufacturing service. In an embodiment, the exported prosthetic design files may be used to generate 3D printer instructions for submission to a 3D printer that is responsive to such instruction to 3D print the prosthetic.

The above-described aspects and embodiments of the present disclosure provide multiple advantages in virtual socket visualization, anatomical treatment planning and anatomical prosthetic design. According to one advantage, anatomical treatment professionals and prosthetic designers can plan treatment and design anatomically accurate prosthetics based on an accurate 3-dimensional model of socket that is the site of treatment planning and prosthetic design and which models a patient's specific socket anatomy.

The model may be generated prior to extraction of the anatomical object from the patient which allows accurate treatment planning and design of the prosthetic prior to, or concurrently (i.e., in parallel) with, the actual surgical extraction of the anatomical object from the patient. This means that the patient may visit the treatment professional for as few as a single visit. During as few as one or two office visits, the patient's anatomical area of interest including the anatomical object targeted for extraction may be scanned. The scan data may be imported into a digital treatment planning tool that includes a virtual socket model generation tool and/or virtual object extraction tool, each of which generates a virtual socket model that is included in the display of a virtual anatomical model of the anatomical area of interest of the patient (i.e., the area that includes the target extraction object and adjacent anatomical objects or features).

With the virtual socket model included in the displayed virtual anatomical model, the treatment professional can more accurately virtually place an implant or other treatment body in the virtual socket model, design and print 3-D printable surgical guides, and export the virtual anatomical model the virtual socket model for use in a separate prosthetic design software tool to design the anatomically accurate prosthetic. If the treatment professional has access to immediate prosthetic manufacture equipment, the prosthetic can be manufactured while the patient is still in the office. Otherwise, the prosthetic can be sent to a lab for manufacture and the patient can return to the office when the anatomical area surrounding the implant has healed sufficiently to attach the prosthetic to the implant.

What is claimed is:

1. A computer implemented method for automatically generating, by one or more computer processors, a 3-dimensional model for use in a virtual extraction of a targeted extraction object of a patient, the targeted extraction object comprising an object in a patient's anatomy, the method based on each of a surface scan of an anatomical region of the patient's oral cavity and a volumetric density scan of the anatomical region, the anatomical region including at least the targeted extraction object, the method comprising:

receiving a first dataset of labeled surface scan segments, each surface scan segment comprising a 3-dimensional (3D) surface model of a corresponding object recognized and segmented from surface scan data of the surface scan, and each surface scan segment having an associated label identifying the surface scan segment;

receiving a second dataset of labeled volumetric density scan segments, each volumetric density scan segment comprising a 3-dimensional (3D) volumetric density model of a boundary surface of a corresponding object recognized and segmented from volumetric density scan data of the volumetric density scan, and each volumetric density scan segment having an associated label identifying the volumetric density scan segment;

cross-mounting in a common 3D coordinate system, labeled surface scan segments from the first dataset to labeled volumetric density scan segments from the second dataset;

receiving identification of the targeted extraction object;

identifying the 3D volumetric density model associated with the volumetric density scan segment label which corresponds to the identified targeted extraction object;

identifying the 3D surface model associated with the surface scan segment label which corresponds to the identified targeted extraction object;

generating a third dataset comprising a model comprising:
a 3D model of a socket being an equivalent of the identified 3D volumetric density model less portions of the identified 3D volumetric density model co-represented in the identified 3D surface model;
at least a portion of the identified 3D volumetric density model co-represented in the identified 3D surface model and/or at least a portion of the identified 3D surface model co-represented in the identified 3D volumetric density model;
at least a portion of the identified 3D volumetric density model less portions of the identified 3D volumetric density model co-represented in the identified 3D surface model; and/or
at least a subset of the first dataset less portions of the identified 3D surface model co-represented in the identified 3D volumetric density model.

2. The method of claim 1, the generation step comprising:
determining portions of the identified 3D volumetric density model not co-represented in the identified 3D surface model; and
storing, in a computer-readable data storage component, the determined portions of the identified 3D volumetric density model as the 3D model of the socket.

3. The method of claim 1, the generation step comprising:
determining portions of the identified 3D volumetric density model co-represented in the identified 3D surface model;
determining a difference between the determined co-represented portions and the identified 3D volumetric density model by removing the determined co-represented portions from the identified 3D volumetric density model; and
storing, in a computer-readable data storage component the determined difference as the 3D model of the socket.

4. The method (100) of claim 1, the generation step comprising:
generating a fourth dataset by removing portions of the identified 3D surface model co-represented in the identified 3D volumetric density model from a copy of at least a subset of the first dataset; and storing, in a computer-readable data storage component, the fourth dataset.

5. The method of any one of claim 4, comprising generating a seventh dataset from the first, second, third and/or fourth dataset or the identified 3D surface model and/or the identified 3D volumetric density model in which a void in a surface defined by the dataset or model, respectively, is augmented by filling the void with generated surface information.

6. The method of claim 5, including generating the generated surface information by interpolation of the boundaries of the void and/or based on standard anatomical modeling.

7. The method of claim 5, comprising storing the third, fourth and/or seventh dataset and/or merged or cross-mounted versions thereof in a computer-readable data storage component.

8. The method of claim 5, wherein the third, fourth and/or seventh dataset and/or merged or cross-mounted versions thereof are used in a virtual extraction procedure of a targeted extraction object of a patient.

9. The method of claim 5, wherein the third, fourth and/or seventh dataset and/or merged or cross-mounted versions thereof are used in a prosthetic design CAD/CAM software tool to generate a prosthetic design which anatomically represents the targeted extraction object of a patient, the use being before, during, and/or during a single office visit as, an actual extraction procedure of the targeted extraction object is performed on the patient.

10. The method of claim 1, wherein labeled surface scan segments from the first dataset are cross-mounted to correspondingly labeled volumetric density scan segments from the second dataset.

11. The method of claim 1, wherein the cross-mounting the first dataset of labeled surface scan segments to the second dataset of labeled volumetric density scan segments includes generating a fifth dataset of labeled segments, each segment comprising a combined 3-dimensional (3D) model representing an anatomical object.

12. The method of claim 11, comprising generating a seventh dataset from the first, second, third and/or fifth dataset or the identified 3D surface model and/or the identified 3D volumetric density model in which a void in a surface defined by the dataset or model, respectively, is augmented by filling the void with generated surface information.

13. The method of claim 12, including generating the generated surface information by interpolation of the boundaries of the void and/or based on standard anatomical modeling.

14. The method of claim 12, comprising storing the third, fifth and/or seventh dataset and/or merged or cross-mounted versions thereof, in a computer-readable data storage component.

15. The method of claim 12, wherein the third, fifth and/or seventh dataset and/or merged or cross-mounted versions thereof are used in a virtual extraction procedure of a targeted extraction object of a patient.

16. The method of claim 12, wherein the third, fifth and/or seventh dataset and/or merged or cross-mounted versions thereof are used in a prosthetic design CAD/CAM software tool to generate a prosthetic design which anatomically represents the targeted extraction object of a patient, the use being before, during, and/or during a single office visit as, an actual extraction procedure of the targeted extraction object is performed on the patient.

17. The method of claim 1, comprising:
determining a boundary of the identified 3D surface model and generating a cut-line therefrom; and
projecting the cut-line onto the identified 3D volumetric density model.

18. The method of claim 17, comprising generating a sixth dataset comprising the identified 3D surface model and/or the identified 3D volumetric density model on the side of the cut-line that includes substantially all portions of the identified 3D volumetric density model that are co-represented in the identified 3D surface model.

19. The method of claim 18, comprising generating a seventh dataset from the first, second, third and/or sixth dataset or the identified 3D surface model and/or the identified 3D volumetric density model in which a void in a surface defined by the dataset or model, respectively, is augmented by filling the void with generated surface information.

20. The method of claim 19, including generating the generated surface information by interpolation of the boundaries of the void and/or based on standard anatomical modeling.

21. The method of claim 19, comprising storing the third, sixth and/or seventh dataset and/or merged or cross-mounted versions thereof, in a computer-readable data storage component.

22. The method of claim 19, wherein the third, sixth and/or seventh dataset and/or merged or cross-mounted versions thereof are used in a virtual extraction procedure of a targeted extraction object of a patient.

23. The method of claim 19, wherein the third, sixth and/or seventh dataset and/or merged or cross-mounted versions thereof are used in a prosthetic design CAD/CAM software tool to generate a prosthetic design which anatomically represents the targeted extraction object of a patient, the use being before, during, and/or during a single office visit as, an actual extraction procedure of the targeted extraction object is performed on the patient.

24. The method of claim 1, comprising generating a seventh dataset from the first, second and/or, third, dataset or the identified 3D surface model and/or the identified 3D volumetric density model in which a void in a surface defined by the dataset or model, respectively, is augmented by filling the void with generated surface information.

25. The method of claim 24, including generating the generated surface information by interpolation of the boundaries of the void and/or based on standard anatomical modeling.

26. The method of claim 24, comprising storing any of the third dataset and/or merged or cross-mounted versions thereof, in a computer-readable data storage component.

27. The method of claim 24, wherein the third and/or seventh dataset are used and/or merged or cross-mounted versions thereof are used in a virtual extraction procedure of a targeted extraction object of a patient.

28. The method of claim 24, wherein the third, fourth, fifth, sixth and/or seventh dataset and/or merged or cross-mounted versions thereof are used in a prosthetic design CAD/CAM software tool to generate a prosthetic design which anatomically represents the targeted extraction object of a patient, the use being before, during, and/or during a single office visit as, an actual extraction procedure of the targeted extraction object is performed on the patient.

29. The method of claim 1, wherein the target extraction object is a tooth and the socket model comprises a 3-dimensional model of a patient's tooth socket which seats the target extraction object.

30. The method of claim 1, wherein the associated labels of each surface scan segment and/or each volumetric density scan segment identifies the surface scan segment or the volumetric density scan segment, respectively, as corresponding to a tooth, a portion of a tooth, a prosthetic tooth, a portion of gum tissue, a portion of bone, an implant, or another object or structure present in the patient's oral cavity and/or the anatomical region.

31. A system for automatically generating a 3-dimensional model for use in a virtual extraction of a targeted extraction object of a patient, the system comprising one or more computer processing units configured to load and execute computer-readable instructions which, when executed configure the one or more computer processing units to implement the method of claim 1.

32. A tangible computer readable medium including storing non-transitory computer readable instructions, which, when executed by one or more computer processing units, configure the one or more computer processing units to implement a method according to claim 1.

33. The method of claim 1, comprising storing the third dataset and/or merged or cross-mounted versions thereof in a computer-readable data storage component.

34. The method of claim 1, wherein the third dataset and/or merged or cross- mounted versions thereof are used in a virtual extraction procedure of a targeted extraction object of a patient.

35. The method of claim 1, wherein the third dataset and/or merged or cross- mounted versions thereof are used in a prosthetic design CAD/CAM software tool to generate a prosthetic design which anatomically represents the targeted extraction object of a patient, the use being before, during, and/or during a single office visit as, an actual extraction procedure of the targeted extraction object is performed on the patient.

\* \* \* \* \*